US011766468B2

(12) United States Patent
van der Meulen et al.

(10) Patent No.: US 11,766,468 B2
(45) Date of Patent: *Sep. 26, 2023

(54) METHOD OF TREATING PROSTATE CANCER WITH GNRH ANTAGONIST

(71) Applicant: Ferring B.V., Hoofddorp (NL)

(72) Inventors: Egbert A. van der Meulen, Dalby (SE); Laszlo Balazs Tanko, Basel (CH)

(73) Assignee: Ferring B.V., Hoofddorp (NL)

( * ) Notice: Subject to any disclaimer, the term of this patent is extended or adjusted under 35 U.S.C. 154(b) by 380 days.

This patent is subject to a terminal disclaimer.

(21) Appl. No.: 16/880,608

(22) Filed: May 21, 2020

(65) Prior Publication Data

US 2021/0128673 A1  May 6, 2021

Related U.S. Application Data

(63) Continuation of application No. 15/205,108, filed on Jul. 8, 2016, now Pat. No. 10,695,398, which is a continuation of application No. 13/458,330, filed on Apr. 27, 2012, now Pat. No. 9,415,085.

(51) Int. Cl.
*A61K 38/16* (2006.01)
*A61K 38/09* (2006.01)
*A61K 38/08* (2019.01)
*A61K 9/00* (2006.01)

(52) U.S. Cl.
CPC .......... *A61K 38/09* (2013.01); *A61K 9/0019* (2013.01); *A61K 38/08* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell |
| 5,506,207 A | 4/1996 | Rivier et al. |
| 5,516,887 A | 5/1996 | Deghenghi |
| 5,595,760 A | 1/1997 | Cherif-Cheikh |
| 5,821,230 A | 10/1998 | Jiang et al. |
| 5,860,957 A | 1/1999 | Jacobsen et al. |
| 5,863,549 A | 1/1999 | Taratino |
| 5,925,730 A | 7/1999 | Semple et al. |
| 6,214,798 B1 | 4/2001 | Semple et al. |
| 6,503,534 B1 | 1/2003 | Pellet et al. |
| 6,875,843 B2 | 4/2005 | Jacobson |
| 8,841,081 B2 | 9/2014 | Persson |
| 9,415,085 B2 | 8/2016 | Van Der Meulen et al. |
| 9,579,359 B2 | 2/2017 | Olesen et al. |
| 9,592,266 B2 | 3/2017 | Schwach et al. |
| 9,822,146 B2 | 11/2017 | Rasmusse et al. |
| 9,877,999 B2 | 1/2018 | Persson |
| 10,172,906 B2 | 1/2019 | Schwach et al. |
| 10,695,398 B2 | 6/2020 | Van Der Meulen et al. |
| 10,729,739 B2 | 8/2020 | Olesen et al. |
| 10,765,721 B2 | 9/2020 | Schwach et al. |
| 10,973,870 B2 | 4/2021 | Olesen et al. |
| 11,260,102 B2 | 3/2022 | Schwach et al. |
| 2002/0001588 A1 | 1/2002 | Sinha |
| 2003/0175736 A1 | 9/2003 | Chinnaiyan et al. |
| 2004/0038903 A1 | 2/2004 | Luck et al. |
| 2004/0138610 A1 | 7/2004 | Cormier et al. |
| 2005/0245455 A1 | 11/2005 | Luck et al. |
| 2005/0282731 A1 | 12/2005 | Bauer et al. |
| 2006/0135405 A1 | 6/2006 | Rischer et al. |
| 2007/0116729 A1 | 5/2007 | Palepu |
| 2007/0238647 A1 | 10/2007 | Bown et al. |
| 2008/0032935 A1 | 2/2008 | Engel et al. |
| 2009/0018085 A1 | 1/2009 | Luck et al. |
| 2009/0203622 A1 | 8/2009 | Persson |
| 2009/0203623 A1 | 8/2009 | Olesen et al. |
| 2009/0209939 A1 | 8/2009 | Verespej et al. |
| 2010/0221266 A1 | 9/2010 | Gregory et al. |
| 2010/0286603 A1 | 11/2010 | Winderstrom |
| 2010/0305042 A1 | 12/2010 | Olesen et al. |
| 2011/0039787 A1 | 2/2011 | Petri et al. |
| 2011/0053846 A1 | 3/2011 | Luck et al. |
| 2012/0172302 A1 | 7/2012 | Petri et al. |
| 2013/0018223 A1 | 1/2013 | Joseph |

(Continued)

FOREIGN PATENT DOCUMENTS

| | | |
|---|---|---|
| CN | 1411803 A | 4/2003 |
| CN | 102204889 | 5/2012 |

(Continued)

OTHER PUBLICATIONS

"Alkaline Phosphatase," GP Notebook (Sep. 12, 2011), http://gpnotebook.co.uk/simplepage.cfm?ID=-1932525548.

Agerso, et al., "The dosing solution influence on the pharmacokinetic of degarelix, a new GnRH antagonist, after s.c. administration to beagle dogs," European Journal of Pharmaceutical Sciences, vol. 20, pp. 335-340, 2003.

Albertsen et al., Reduced Risk of Cardiovascular (CV) Events and Death in Patients (PTS) Receiving Degarelix Compared with LHRH Agonists (2012).

Albertsen, et al. "Cardiovascular Morbidity Associated with Gonadotropin Releasing Hormone Agonist and an Antagonist," European Urology (2013), https://dx.doi.org/10.16/j.eururo.2013.10,032.

(Continued)

*Primary Examiner* — Michael D Pak
(74) *Attorney, Agent, or Firm* — Foley & Lardner LLP

(57) ABSTRACT

The invention provides methods and dosing regimens for safely and effectively treating androgen-dependent prostate cancer with a gonadotrophin releasing hormone (GnRH) antagonist without causing a testosterone spike and/or other side effect of GnRH agonist therapy such as a urinary tract infection, or an arthralgia-related or cardiovascular side effect. The present disclosure also provides for methods for treating prostate cancer in a patient with a history of at least one cardiovascular event, wherein administration of degarelix to the subject decreases the likelihood of developing or experiencing an additional cardiovascular event compared to treatment with a gonadotrophin releasing hormone (GnRH) agonist.

11 Claims, 10 Drawing Sheets

(56) References Cited

U.S. PATENT DOCUMENTS

| | | | |
|---|---|---|---|
| 2013/0029910 | A1 | 1/2013 | Meulen et al. |
| 2013/0281661 | A1 | 10/2013 | Rasmusse et al. |
| 2013/0281662 | A1 | 10/2013 | Kalita et al. |
| 2013/0295166 | A1 | 11/2013 | Grenier et al. |
| 2019/0167755 | A1 | 6/2019 | Persson |
| 2021/0138024 | A1 | 5/2021 | Schwach et al. |
| 2022/0031801 | A1 | 2/2022 | Olesen et al. |

FOREIGN PATENT DOCUMENTS

| | | |
|---|---|---|
| EP | 0 002 749 B1 | 10/1983 |
| EP | 0 556 034 A1 | 8/1993 |
| EP | 1 003 774 B1 | 5/2000 |
| EP | 1630169 | 8/2007 |
| EP | 1 967 202 A1 | 9/2008 |
| FR | 2 776 520 A | 10/1999 |
| WO | WO 97/34923 | 9/1997 |
| WO | WO 98/46634 | 10/1998 |
| WO | WO 99/26964 A1 | 6/1999 |
| WO | WO 2003/006049 A1 | 10/2003 |
| WO | WO 2007/130809 A2 | 11/2007 |
| WO | WO-2008/017664 A2 | 2/2008 |
| WO | WO 2008/135989 A1 | 11/2008 |
| WO | WO 2009/090189 A1 | 7/2009 |
| WO | WO 2009/101533 A1 | 8/2009 |
| WO | WO 2010/121835 | 4/2010 |
| WO | WO 2011/004260 A2 | 1/2011 |
| WO | WO 2012/013331 A2 | 2/2012 |
| WO | WO 2012/055905 | 5/2012 |

OTHER PUBLICATIONS

Amblard et al., "Methods and Protocols of Modern Solid Phase Peptide Synthesis," Mol. Biotechnol. 33: 239-254 (2006).

Andersson et al., "Large-Scale Synthesis of Peptides," Biopolymers (Peptide Science), pp. 227-250, 2000.

Austria_Codex Fachinformation 2006/2007.

Bak et al., "Physicochemical and Formulation Developability Assessment for Therapeutic Peptide Delivery—A Primer," the AAPS Journal, vol. 17, No. 1, pp. 144-155, Jan. 2015.

Bracarda et al., "Cancer of the Prostate," Crit. Rev. Oncology / Hematology 56: 379-396 (2005).

Behn, et al., "The obesity epidemic and its cardiovascular consequences," (2006) Curr. Opin. Cardiol. vol. 21, pp. 353-360.

Berges, et al., "Effect of a new leuprorelin formulation on testosterone levels in patients with advanced prostate cancer," (2006), Cur. Med. Res. Opin., vol. 22, No. 4, pp. 649-655.

Boccon-Gibod et al: "Optimising Hormone Therapy in Advanced Disease" European Urology Suplements, vol. 4, No. 8, Nov. 1, 2005 (Nov. 1, 2005), pp. 21-29, XP005112815 ISSN: 1569-9056.

Boccon-Gibod, et al., "Cyproterone Acetate Lead-In Prevents Initial Rise of Serum Testosterone Induced by Luteinizing Hormone-Releasing Hormone Analogs in the Treatment of Metastatic Carcinoma of the Prostate," (1986) Euro. Urol., vol. 12, pp. 400-402.

'Bone Specific Alkaline Phosphatase,' The University of Iowa (UIHC), Department of Pathology, Laboratory Services Handbook (Sep. 11, 2011), http://www.healthcare.uiowa.edu/path_handbook/handbook/test2238.html.

Boyle et al: "Treatment of hormone sensitive prostate cancer" European Journal of Cancer. Supplement, Pergamon, Oxford, GB, vol. 3, No. 3, Oct. 1, 2005 (Oct. 1, 2005), pp. 331-338, XP005130027 ISSN: 1359-6349.

Bray, "Large-Scale manufacture of peptide therapeutics by chemical synthesis," Nature Review, vol. 2, pp. 587-593, Jul. 2003.

Broqua et al., "Effects of the New GNRH Antagonist FE200486 one the Growth of the Androgen-Dependent Prostate Tumor Dunning R-3327H, 6th International Symposium on GnRH Analogues in Cancer and Human Reproduction," Geneva, Switzerland, Feb. 8, 2001.

Broqua, et al., "Pharmacological Profile of a New, Potent, and Long-Acting Gonadotropin-Releasing Hormone Antagonist: Degarelix," The Journal of Pharmacology and Experimental Therapeutics, vol. 301, pp. 95-102, 2002.

Cancer Trends Progress Report, 2001; 2003 Update; 2005 Update; 2007 Update; 2009/2010 Update, http://progressreport.cancer.gov. (last visited Jun. 1, 2012).

Cetrotide TM package insert (Aug. 11, 2000).

Chernecky, and Berger, "Laboratory Tests and Diagnostic Procedures," (2008) Fifth Edition, WB Saunders & Company, Philadelphia. ISBN-978-1-14160-3704-0.

ClinicalTrials.gov, View of NCT00728533 titled "Open-Label, Randomised Parallel-Group Study," Feb. 19, 2009.

Conn, P. M. "Gonadotropin-releasing hormone and its analogs," Ann. Rev. Med. (1994) 45:391-405.

Council of Europe, Strasbourg, "European Pharmacopoeia 6263" European Directorate for the Quality of Medicines & Healthcare (2007).

Council of Europe, Strasbourg, "European Pharmacopoeia6748" European Directorate for the Quality of Medicines & Healthcare (2007).

Crawford et al., "A Phase III Extension Trial With a 1-Arm Crossover From Leuprolide to Degarelix: Comparison of Gonadotropin-Releasing Hormone Agonist and Antagonist Effect of Prostate Cancer," 186 The Journal of Urology 889-897 (2011).

Crawford et al., "Long term tolerability and efficacy of degarelix: 5-year results from a phase III extension trial with a one-arm crossover from leuprolide to degarelix", Urologic Oncology, School of Medicine, University of Colorado Denver, pp. 1-18; Mar. 22, 2014.

Crawford et al., Degarelix Versus LHRH Agonists: Differential Skeletal Morbidity Outcomes from a Pooled Analysis of Six Comparative Randomised Clinical Trials (2012).

Damber et al., "Comparing Testosterone and PSA for Different Baseline Testosterone Concentrations During Initiation of Degarelix and Leuprolide Treatment," European Urology Supplements (2009) 8(4), 130, Abstr No. 39.

De la Rosette et al., "Efficacy and safety of androgen deprivation therapy after switching from monthly leuprolide to monthly degarelix in patients with prostate cancer," 65(5) International Journal of Clinical Practice 559-66 (2011).

De Pinieux, et al., "Clinical and Experimental Progression of a New Model of Human Prostate Cancer and Therapeutic Approach," American Journal of Pathology, vol. 159, No. 2, Aug. 2001, 753-764.

Debruyne, "Gonadotropin-Releasing Hormone Antagonist in the Management of Prostate Cancer," Med Reviews, LLC (2004), vol. 6, pp. S25-S32.

Debruyne, et al., "Abarelix for injectable suspension: first-in-class gonadotropin-releasing hormone antagonist for prostate cancer," (2006) Future Oncol., vol. 2, pp. 677-696.

Degarelix Study Group Tammela et al: "904Degarelix—a phase 11 multicenter, randomized dose-escalating study testing a novel gnrh receptor blocker in prostate cancer patients" Euorpean Urology Supplements, vol. 4, No. 3, Mar. 1, 2005 (Mar. 1, 2005), p. 228, XP005007365 ISSN: 1569-9056.

Demers et al., "Biochemical Markers and Skeletal Metastases," Cancer, vol. 88, pp. 2919-2926, Mar. 2, 2000.

Denis, et al., "Overview of Phase III Trials on Combined Androgen Treatment in Patients with Metastatic Prostate Cancer," (1993) Cancer, vol. 72, pp. 3888-3895.

Doehn Christian et al: "Drug evaluation: Degarelix—a potential new therapy for prostate cancer." IDRUGS: The Investigational Drugs Jounral Aug. 2006, vol. 9, No. 8, Aug. 2006 (Aug. 2006), pp. 565-572, XP009105353 ISSN: 1369-7056.

Eastman et al., "Serum Alkaline Phosphatase: Normal Values by Sex and Age," 23(9) Clinical Chemistry 1769-1770 (1977).

Etzioni, et al., "Cancer Surveillance Series: Interpreting Trends in Prostate Cancer—Part III: Quantifying the Link Between Population Prostate-Specific Antigen Testing and Recent Declines in Prostate Cancer Mortality," (1999) J. Natl. Canc. Inst., vol. 91, pp. 1033-1039.

(56) References Cited

OTHER PUBLICATIONS

European Patent Office Communication pursuant to Article 94(3) EPC dated Apr. 10, 2014, in corresponding Application No. 11 776 745.9 (5 pages).
European Search Report & Opinion, dated Oct. 2, 2012, EP Application No. 12168495.5.
FDA Drug Information Page—Plenaxis (abarelix for injectable suspension); http://www.fda.gov/cder/drug/infopage/planaxis/default.htm. (Feb. 2004).
FDA.gov, Label for Degarelix for injection (Dec. 24, 2008), available at www.accessdata.fda.gov/drugsatfda_docs/label/2008/022201lbl.pdf, last visited Jun. 4, 2013.
Ferlay, et al., "Estimates of the cancer incidence and mortality in Europe in 2006," Annals of Oncology, vol. 18, pp. 581-592 (2007).
Ferring BV, "GnRH Antagonists", Indian Granted Patent IN224650 based on PCT Application WO9846634, dated Oct. 22, 1998, pp. 1-43.
First Amended Complaint, *Ferring Pharmaceuticals v. Fresenius Kabi*, U.S. Delaware District Court, filed May 28, 2020.
Fleming, et al., "Post-therapy changes in PSA as an outcome measure in prostate cancer clinical Trials," (2006) Nature Clinical Practice Oncolology, vol. 3, No. 12, pp. 658-667.
Forbes, et al., "FDA'S Adverse Drug Reaction Drug Dictionary and Its Role in Post-Marketing Surveillance," (1986) Drug Inf. J., vol. 20, pp. 135-145.
Frampton et al., "Degarelix", ADIS International, Drugs, 69 (14): 1967-1976 (2009).
Fresenius Kabi's Initial Invalidity Contentions, *Ferring Pharmaceuticals v. Fresenius Kabi*, U.S. Delaware District Court, filed Sep. 18, 2020.
Garnero, "Markers of bone turnover in prostate cancer," Cancer Treatment Reviews, pp. 187-192: 27: 2001.
Garnick M et al: "217 Increase in the electrocardiographic QTC interval in men with prostate cancer undergoing androgen deprivation therapy: Results of three randomized controlled clinical studies", European Urology Supplements, vol. 3, No. 2, Feb. 1, 2004 (Feb. 1, 2004), p. 57, XP027186629, ISSN: 1569-9056.
Gerlinger, et al., "Recommendation for Confidence interval and sample size calculations for the Pearl Index," (2003) The European Journal of Contraception and Reproductive Health Care, vol. 8, pp. 87-92.
Gillum, T., "The Merck Regulatory Dictionary: A Pragmatically Develop Drug Effects Vocabulary," (1989) Drug Info. J., vol. 23, pp. 217-220.
Gittelman et al., "A 1-Year, Open Label, Randomized Phase II Doe Finding Study of Degarelix for the Treatment of Prostate Cancer in North America," The Journal of Urology, vol. 80, pp. 1986-1992, Nov. 2008.
Gittelman et al: "MP-08.21: A multicentre, randomised one year dose-finding study of degarelix, a gonadotrophin-releasing hormone (GnRH) receptor blocker in prostate caner patients" Urology, Belle Mead, NJ, US vol. 70 No. 3, Sep. 1, 2007 (Sep. 1, 2007) pp. 83-84, XP022248654 ISSN:0090-4295.
Gonzalez-Barcena et al., "Luteinizing Hormone-Releasing Hormone Antagonist Cetrorelix as Primary Single Therapy in Patients with Advanced Prostatic Cancer and Paraplegia Due to Metastatic Invasion of Spinal Cord," (1995), vol. 45, pp. 275-281.
Granfors, et al., "Combined Orchiectomy and External Radiotherapy Versus Radiotherapy Alone for Nonmetastatic Prostate Cancer With or Without Pelvic Lymph Node Involvement: A Prospective Randomized Study," J. Urol., (1998), 159:2030-34.
Hackman, et al., "Emerging Risk Factors for Atheroslerotic Vascular Disease," (2003), JAMA, vol. 290, pp. 932-940.
Hegele et al., "Biochemical Markers of Bone Turnover in Patients with Localized and Metastasized Prostate Cancer," Journal Compilation, vol. 99, pp. 330-334, Sep. 7, 2006.
Heidenreich et al., "Welche Mechanismen Liegen Der Besseren Kontrolle Des Psa-Progressionsfreien Uberlebens Von Degarelix Im Vergleich Mit Leuprorelin Zugrunde?", RWTH, Aache, Ferring Arzneimittel GmbH, Kiel, 4 pages.

Hellerstedt, et al., "The Current State of Hormonal Therapy for Prostate Cancer," CA A Cancer Journal for Clinicians, vol. 52, pp. 154-179 (2002).
Holdaway, et al. "Treatment of metastatic prostate carcinoma with the depot LRH analog Zoladex," The Prostate 12: 199-127 (1988).
Huggins et al., "Studies on Prostatic Cancer. I. The Effect of Castration, of Estrogen and of Androgen Injection on Serum Phosphatases in Metastatic Carcinoma of the Prostate," Cancer Res. (1941) 1:293-297.
Huggins et al., "I. The Effect of Castration, of Estrogen and of Androgen Injection on Serum Phosphatases in Metastatic Carcinoma of the Prostate," J. of Urol. (2002) 168:9-12.
Huirne J A et al: "Gonadotropin-releasing-hormone-receptor antagonists" Lancet The, Lancet Limited. London, GB, vol. 358, No. 9295, Nov. 24, 2001 (201-11-24), pp. 1793-1803, XP04805574 ISSN: 0140-6736.
International Search Report dated Sep. 12, 2002, in Application No. PCT/GB02/03116.
Isidro-Llobet et al., "Amino Acid-Protecting Groups," Chem. Rev, pp. 2455-2504, 2009.
Iversen et al., "Improved outcomes with degarelix monotherapy compared with luteinizing hormone-releasing hormone (LHRH) agonists plus antiandrogen in the treatment of men with advanced prostate cancer", 29th Congress of the Scandinavian Association of Urologiest, May 22, 2013, 2 pages.
Iversen et al: "MP-08.18" Urology, Belle Mead, NJ, US, vol. 68, Nov. 1, 2006 (Nov. 1, 2006), p. 102, XP05709326 ISSN 0090-4295.
Jadhav et al., "Semi-Mechanistic Pharmacodynamic Modeling for Degarelix, a Novel Gonadotrophin Releasing Hormone (GnRH) Blocker," J. of Pharmacokinetics and Pharmacodynamics, vol. 13, No. 5, Oct. 2006.
Jiang et al., "Betidamino Acid-Scan of the GNRH Antagonist Acyline," Journal of Medicinal Chemistry, American Chemical Society, Washington, US, vol. 40, 1997, pp. 3739-3748.
Jiang, et al., "GnRH Antagonists: A New Generation of Long Acting Analogues Incorporating p-Ureido-phenylalanies at Positions 5 and 6," (2001) J. Med. Chem., vol. 44, pp. 453-467.
Keating Nancy L et al: "Diabetes and cardiovascular disease during androgen deprivation therapy for prostate cancer." Journal of Clinical Oncology: Official Journal of the American Society of Clinical Oncology Sep. 20, 2006, vol. 24, No. 27, Sep. 20, 2006 (Sep. 20, 2006), pp. 4448-4456, XP002687918, ISSN: 1527-7755.
Kirk et al., "Immediate Versus deferred treatment for advanced prostatic cancer; initial results of the Medical Research Counsel trial.," British Journal of Urology, (1997) vol. 79, pp. 235-246.
Klotz, et al., "The efficacy and safety of degarelix: a 12-month, comparative, randomized, open-label, parallel-group phase III study in patients with prostate cancer," BJU International, 102, pp. 1531-1538, Nov. 21, 2008.
Lehmann, "Testing Statistical Hypotheses," (1986) Second Edition, John Wiley & Sons, New York, ISBN 0-471-84083-1.
Levine, et al., "Androgen-Deprivation Therapy in Prostate Cancer and Cardiovascular Risk," AHA/ACS/AUA Science Advisory, Circulation, pp. 833-840, 2010.
Lilja, et al., "Prostate-specific antigen and prostate cancer: prediction, detection and monitoring," (2008) Nature Reviews/Cancer, vol. 8, pp. 268-278.
Lukka, et al., "Maximal androgen blockade for the treatment of metastatic prostate cancer—a systematic review," Current Oncology, vol. 13, No. 3, pp. 81-93. (2006).
Lyseng-Williamson, Katherine A., "Degarelix: a guide to its use in advanced prostate cancer," 28(5) Drugs Ther. Perspect. 6-10 (2012).
Magnusson P. et al, "Differences of bone alkaline phosphatase isoforms in metastatic bone disease and discrepant effects of clodronate on different skeletal sites indicated by the location of pain," Clinical Chemistry (1998) 44(8):1621-1628.
Malkin, "Are techniques used for intramuscular injection based on research evidence?" Nursingtimes.net, Nursing Times; 104; 50/51, 48-51 Dec. 16, 2008.
Manning et al., "Stability of Protein Pharmaceuticals: An Update," Pharmaceutical Research, vol. 27, No. 4, pp. 544-575, Apr. 2010.

(56) References Cited

OTHER PUBLICATIONS

McNeil, et al., "On the Elicitation of Preferences for Alternative Therapies," (1982) N. Engl. J. Med., vol. 306, No. 21, pp. 1259-1262.
MedDRA website, http://www.meddramsso.com. (2009).
Messing, et al., "Immediate Hormonal Therapy Compared with Observation after Radical Prostatectomy and Pelvic Lyphadenectomy in Men with Node-Positive Prostate Cancer," (1999), N. Eng. J. Med., vol. 341, pp. 1781-1788.
Miller et al., Differential outcomes from an analysis of six comparative randomised clinical trials of degarelix versus luteinising hormone-releasing hormone (LHRH) agonists) (2012).
Miller et al., "Disease control-related outcomes from an analysis of six comparative randomised clinical trials of degarelix versus luteinising hormone-releasing hormone (LHRH) agonists," (2012).
Mongiat-Artus P et al: "Role of Luteinising Hormone Releasing Hormone (LHRH) Agonists and Hormonal Treatment in the Management of Prostate Cancer" European Urology Supplements, vol. 4, No. 5, Jul. 1, 205 (Jul. 1, 2005), pp. 4-13, XP004926296 ISSN: 1569-9056.
Mongiat-Artus, et al., "Abarelix: the first gonadotrophin-releasing hormone antagonist for the treatment of prostate cancer," (2004), Expert Opin. Pharmacother, vol. 5, pp. 2171-2179.
Montalbetti et al., "Amide bond formation and peptide coupling," Science Direct (Tetrahedron 2005), pp. 10827-10852.
Nalesnik J.G. et al, "Anemia in men with advanced prostate cancer: Incidence, etiology, and treatment," Reviews in Urology (2004) 6(1): 1-4.
National Cholesterol Education Program (NCEP) Guidelines for Interpretation of Lipid Values, (2001; updated 2004) XP-02729834.
NCEP ATP III Classification of Total Cholesterol, LDL-C, and HDL-C, XP-02729835 (2003 first publication; 2010).
Notice of Opposition against EP2249859 to Ferring B.V., filed Jan. 23, 2015.
Notice of Opposition against EP2505204 to Ferring B.V., filed Sep. 24, 2015.
Notice of Opposition against EP2650012 to Ferring B.V., filed Dec. 24, 2015.
Office Action (Final), dated Apr. 19, 2019) U.S. Appl. No. 15/405,552.
Office Action (final) dated Feb. 8, 2017, U.S. Appl. No. 14/747,218.
Office Action (final) dated Jan. 29, 2015, U.S. Appl. No. 12/155,897.
Office Action (final) dated Jan. 29, 2016, U.S. Appl. No. 12/901,270.
Office Action (final) dated Jan. 9, 2014, U.S. Appl. No. 12/829,467.
Office Action (final) dated Jul. 14, 2016, U.S. Appl. No. 14/454,825.
Office Action (final) dated Mar. 10, 2016, U.S. Appl. No. 14/139,922.
Office Action (final) dated Mar. 24, 2016, U.S. Appl. No. 13/458,330.
Office Action (final) dated Mar. 5, 2014, U.S. Appl. No. 12/155,897.
Office Action (final) dated Mar. 6, 2014, U.S. Appl. No. 12/901,270.
Office Action (final) dated Oct. 8, 2013, U.S. Appl. No. 13/381,762.
Office Action (final) dated Sep. 12, 2017, U.S. Appl. No. 12/901,270.
Office Action (final) dated Apr. 8, 2016, U.S. Appl. No. 14/403,775.
Office Action (Final) dated May 20, 2014, in co-pending U.S. Appl. No. 13/458,330.
Office Action (non-final) dated Apr. 7, 2017, U.S. Appl. No. 12/368,935.
Office Action (non-final) dated Feb. 19, 2016, U.S. Appl. No. 14/454,825.
Office Action (non-final) dated Jun. 16, 2016, U.S. Appl. No. 14/747,218.
Office Action (non-final) dated Jun. 30, 2015, U.S. Appl. No. 13/458,330.
Office Action (non-final) dated Jun. 5, 2015, U.S. Appl. No. 12/155,897.
Office Action (non-final) dated Jun. 4, 2015, U.S. Appl. No. 14/139,922.
Office Action (non-final) dated Jun. 5, 2015, U.S. Appl. No. 12/901,270.
Office Action (non-final) dated Sep. 3, 2015, U.S. Appl. No. 14/403,775.
Office Action dated Apr. 10, 2018, U.S. Appl. No. 12/901,270.
Office Action dated Dec. 19, 2017, U.S. Appl. No. 15/420,156.
Office Action dated Jul. 25, 2013, U.S. Appl. No. 12/829,467.
Office Action dated Jul. 26, 2013, U.S. Appl. No. 12/901,270.
Office Action dated Jun. 11, 2013, U.S. Appl. No. 13/381,762.
Office Action dated Jun. 28, 2018, U.S. Appl. No. 15/405,552.
Office Action dated Jun. 6, 2013, U.S. Appl. No. 12/774,113.
Office Action dated May 5, 2015, U.S. Appl. No. 13/881,751.
Office Action dated Nov. 1, 2018, in co-pending U.S. Appl. No. 12/901,270.
Office Action dated Sep. 11, 2013, in U.S. Appl. No. 12/771,199.
Office Action dated Sep. 3, 2013, in U.S. Appl. No. 13/458,330.
Office Action dated Apr. 2, 2012, in copending U.S. Appl. No. 12/368,935.
Office Action dated Aug. 27, 2014 in U.S. Appl. No. 13/881,744.
Office Action dated Dec. 3, 2013, in copending Appplication No. U.S. Appl. No. 12/368,713.
Office Action dated Jan. 31, 2013, in copending U.S. Appl. No. 12/901,270.
Office Action dated Jul. 8, 2016, U.S. Appl. No. 15/205,108.
Office Action dated Mar. 1, 2011, in copending U.S. Appl. No. 12/368,713.
Office Action dated Mar. 30, 2017, in copending U.S. Appl. No. 14/454,825.
Office Action dated Mar. 8, 2011, in copending U.S. Appl. No. 12/155,897.
Office Action dated Oct. 12, 2011, in U.S. Appl. No. 12/155,897.
Office Action dated Oct. 2, 2014, in copending U.S. Appl. No. 12/829,467.
Office Action dated Oct. 22, 2009, in co-pending U.S. Appl. No. 12/155,897.
Ozono, et al., "Efficacy and safety of a 3-month dosing regimen of degarelix in Japanese patients with prostate cancer: a phase II maintenance-dose-finding study," Jpn J Clin Oncol. (2017) 47(5): 438-446.
Paragraph IV Letter, filed by Fresenius Kabi against Ferring Pharmaceutical, Feb. 10, 2020.
People's Republic of China First Office Action dated Feb. 25, 2013 in corresponding Application No. 201080019696.2, 2 pages.
Persad, "Leuprorelin Acetate in Prostate Cancer: A European Update," (2002) Int. J. Clin. Pract., vol. 56, No. 5, pp. 389-396.
Princivalle et al. "Rapid Suppression of Plasma Testosterone Levels and Tumor Growth in the Dunning Rat Model Treated with Degarelix, a New Gonadotrophin-Releasing Hormone Antagonist," J. Pharmacol. Exp. Ther. 320(3):1113-1118 (2007).
Ramaswamy et al., "Serum Levels of Bone Alkaline Posphatase in Breast and Prostate Cancers with Bone Metastasis," Indian Journal of Clinical Biochemistry, pp. 110-113, 15(2), 2000.
Rivier, J. et al., "Gonadotropin-releasing hormone antagonists with Nw-Triazolylornithine, -lysine, or -p-aminophenvlalanine residues at positions 5 and 6." Journal of Medical Chemistry (1992) 35:4270-4278.
Romero-Corral, et al., "Association of bodyweight with total mortality and with cardiovascular events in coronary artery disease: a systematic review of cohort studies," (2006) Lancet, 368:666-678.
Saltzman, A., "Adverse Reaction Terminology Standardization: A Report on Schering-Plough's Use of the WHO Dictionary and the Formation of the WHO Adverse Reaction Terminology Users Group (WUG) Consortium," (1985) Drug Info. J., vol. 19, pp. 35-41.
Samant et al., "Novel analogues of degarelix incorporating hydroxy-, methoxy- and pegylated-urea moieties at positions 3, 5, 6 and the N-terminus," J. Med Chem. 49(12), pp. 3536-3543, 2006.
Sartor, O. "Eligard® 6: A new form of treatment for prostate cancer," European Urol. Supp. (2006) 5:905-910.
Schwach et al., "Biodegradable PLGA microparticles for sustained release of a new GnRH antagonist . . . ," European Journal of Pharmaceutics and Biopharmaceuticals, May 1, 2004, vol. 57, No. 3, pp. 441-446.
Schwach G. et al: "Biodegradable microparticles for sustained release of a new GnRH antagonist—part I: screening commercial PLGA and formulation technologies", European Journal of Pharmaceutics and Biopharmaceutics, Elsevier Science Publishers B.V., Amsterdam, NL, vol. 56, No. 3, Nov. 1, 2003, pp. 327-336.

(56) References Cited

OTHER PUBLICATIONS

Shahani et al., "Androgen deprivation therapy in prostate cancer and metabolic risk for atherosclerosis," J. Clin. Endocrinol. Metab. 93(6):2402-2049 (Jun. 2008).
SEER Program and the National Center for Health Statistics, <http://seer.cancer.gov/.> (2000; 2005).
Shamdas et al., Leukoerythroblastic anemia in metastatic prostate cancer, Cancer 71(11):3594-3600 (1993).
Sharma et al., "To scale or not to scale: the principles of does extrapolation," British Journal of Pharmacology, pp. 907-921, 2009.
Smith, M.R. et al., "Gonadotropin-Releasing Hormone Blockers and Cardiovascular Disease Risk: Analysis of Prospective Clinical Trials of Degarelix," 186 The Journal of Urology 1835-1842 (2011).
Sorbera et al., "Degarelix Acetate", GnRH Antagonist Prostate Cancer Therapy; Drugs of the Future 2006, vol. 31, No. 9, pp. 755-766.
Spilker, Bert, "Guide to Cinical Trials," (1991) Raven Press, Ltd., New York, ISBN 0-88167-767-1.
Spilker, Bert, "Quality of Life and Pharmacoeconomics in Clinical Trials," (1996) Lippincott—Raven Publishers, New York, ISBN 0-7817-0332-8.
Steinberg, et al., "Degarelix: A Gonadotropin-Releasing Hormone Antagonist for the Management of Prostate Cancer," Clinical Therapeutics, vol. 31, pp. 2312-2331, 2009.
Stephens, M.D.B., "The Detection of New Adverse Drug Reactions," (1988) Stockton Press, New York, ISBN 0-333-45417-0.
Tammela et al., "Degarelix—A Phase II Multicentre, Randomized Dose-escalating Study Testing a Novel GnRH Receptor Blocker in Prostate Cancer Patients," Eur. Urol. Supp. 4(3), p. 288, 2005.
Teal, et al., "Adverse Drug Experience Management: A Brief Review of the McNeil Pharmaceutical System," (1985) Drug Info. J., vol. 19, pp. 17-25.
The K-Zone, Biophysical data tables: standard man, Jul. 2004; printed Mar. 14, 2009 from www.kevinboone.com/biodat_stdman. html; 1 page.
Thompson, et al., "Sudden Death to Disease Flare With Luteinizing Hormone-Releasing Hormone Agonist Therapy for Carcinoma of the Prostate," J. Urol., (1990) vol. 144, pp. 1479-1480.
Tolis, G. et al, "Tumor growth inhibition in patients with prostatic carcinoma treated with luteinizing hormone-releasing hormone agonists", PNAS (1982) 79:1685-1662.
Tombal et al., "Determining the dose of degarelix for effective therapy of prostate cancer patients as investigated by the degarelix study groups," Annals of Oncology vol. 17 (Supplement 9), pp. ix144-ix157, ix150, 2006.
Tornøe et al., "Population Pharmacokinetic Modeling of a Subcutaneous Depot for GnRH Antagonist Degarelix," Pharmaceutical Research, vol. 21, No. 4, pp. 574-584, 2004.
Tsai Henry K et al: Androgen deprivation therapy for localized prostate cancer and the risk of cardiovascular mortality., Journal of the National Cancer Institute Oct. 17, 2007 LNKD-PUBMED:17925537, vol. 99, No. 20, Oct. 17, 2007 (Oct. 17, 2007), pp. 1516-1524, XP002687919, ISSN: 1460-2105.
Tucci, et al. "Prognostic significance of disordered calcium metabolism in hormone-refractory prostate cancer patients with metastatic bone disease", Prostate Cancer—and Prostatic Diseases (2009) 12:94-99.
Turner, et al., "The Processing of Adverse Reactoin Reports at FDA," (1986) Drug. Inf. J., vol. 20, pp. 147-150.
Van Kerrebroeck et al., "Desmopressin in the Treatment of Nocturia: A Double-Bind, Placebo-Controlled Study", European Urology, 52, (Jan. 16, 2007).
Van Poppel et al., "A One-Year, Multicentre, Randomised Study of Degarelix a Gonadatrophin-Releasing Hormone (GNRH) Receptor Blocker, in Prostate Cancer Patients," Eur Urol Suppl 2005:5(2):251.
Van Poppel et al., "Degarelix: A Novel Gonadotropin-Releasing Hormone (GnRH) Receptor Blocker-Results from a 1-yr, Multicentre, Randomised, Phase 2 Dosage-Finding Study in the Treatment of Prostate Cancer", European Urology No. 54, pp. 805-815 (2008).
Van Poppel H et al: "23 Long-Term Evaluation of Degarelix, a Gonadotrophin-Releasing Hormone (GNRH) Receptor Blocker, Investigated in a Multicentre Randomised Study in Prostate Cancer (CAP) Patients" European Urology Supplements, vol. 6, No. 2, Mar. 1, 2007 (Mar. 1, 2007), p. 28, XP022686644 ISSN: 1569-9056 [retrieved on Mar. 1, 2007].
Van Poppel, "Evaluation of degarelix in the management of prostate cancer," Cancer Management and Research, vol. 2, pp. 39-52, 2010.
Van Poppel et al., "Testosterone Surge: Rationale for Gonadotropin-Releasing Hormone Blockers," Urology 71(6):1001-06 (2008).
Versuchsbericht Zerfallzeit Ursprunglicher Dateiname:D13,Beigefugt als:Other-evidence-1 (Jul. 23, 2014).
Wiegel et al., "Neoadjuvant Androgen Deprivation Therapy for Prostate Volume Reduction, Lower Urinary Tract Symptom Relief and Quality of Life Improvement in Men with Intermediate- to High-risk Prostate Cancer: A Randomised Non-inferiority Trial of Degarelix versus Goserelin plus Bicalutamide", 2 pages.
Wilson, et al., "Leuprolide acetate: a drug of diverse clinical applications," Expert Opin. Investig. Drugs, (2007), vol. 16, pp. 1851-1863.
Wilson, et al., "Prediction of Coronary Heart Disease Using Risk Factor Categories," (1998) Circulation, 97:1837-47.
Wolff et al., "Cumulative analysis from six comparative randomised clinical trials of degarelix versus luteinising hormone-releasing hormone (LHRH) agonists: Better PSA-progressionfree survival confirmed in trials an everyday practice", Gerring Arzneimittel GmbH, Kiel, 2 pages.
Yannucci, et al., "The Effect of Androgen Deprivation Therapy on Fasting Serum Lipid and Glucose Parameters," (2006) J. Urol., vol. 176, pp. 520-525.
Ye, L. et. al., "Bone metastasis in prostate cancer: Molecular and cellular mechanisms (Review)," International Journal of Molecular Medicine (2007) 20 103-111.
A. Plantade et al., Locally advanced prostate cancer: definition prognosis and treatment, Bull. Cancer, 94 (7 Suppl.):F50-61, Jul. 2007 (Abstract).
Aldrich, Handbook of Fine Chemicals and Laboratory Equipment—2003—2004 US, Dimethylfo, 734.
Blagoeva et al., "Intramolecular Nucleophilic Attack on Carboxylate by Ureide Anion. General Acid-Base Catalysis of The Alkaline Cyclisation Of 2,3,3,5-Tetramethylhydantoic Acid" Journal Chemical Society Perkin Transactions II 745-751 (1984).
Boccon-Gibod et al., "Degarelix Compared to Leuprolide Depot 7.5 mg in a 12-Month Randomised, Open-Label, Parallel-Group Phase III Study in Prostate Cancer Patients," Eur. Urol. Suppl. 7:205 (2008).
Boccon-Gibod, "Global Update on defining and treating high-risk localized prostate cancer with leuprorelin: a European perspective" JU International, Suppl 1 :2-5, 2007.
Bubley, "Is the Flare Phenomenon Clinically Significant?" Urology 58:5-9 (2001).
C. Doehn et al., Drug evaluation: Degarelix—a potential new therapy for prostate cancer, IDrugs, 9(8):565-572, 2006.
Castells et al., "Synthesis of a Chemically Bound Chiral Silica Phase," Reactive Polymers 6:207-211 (1987).
FDA Guidance for Industry Q3B(R2) Impurities in New Drug Products, Rev 2 (Jul. 2006).
*Ferring Pharm. Inc. v. Fresenius Kabi USA, LLC*, Memorandum Opinion, 1:20-cv-00431-MN (D. Del. Dec. 12, 2022).
Final Office Action received in U.S. Appl. No. 17/710,905 dated Aug. 29, 2022.
Firmagon Package Insert (Dec. 2008).
Garnero, "Markers of bone turnover in prostate cancer," Cancer Treat. Rev., 27:187-192 (2001).
Gittelman et al., "Degarelix: A gonadotropin-releasing hormone receptor (GnRH) blocker, tested in two one-year multicenter, randomized, dose-finding studies in prostate cancer patents," J. Clin. Oncol. 24:14516 (2006).
Gotsman et al., "Tcell costimulation and coinhibition in atherosclerosis," Circulation Res 103:1220-1231 (2008).
Greiman et al., "Approach to Androgen Deprivation in the Prostate Cancer Patient with Pre-existing Cardiovascular Disease," Cur Urol Rep 18:41 (2017).

(56) References Cited

OTHER PUBLICATIONS

Iverson et al., "Determining the optimal initiation and maintenance dose of degarelix for hormone therapy of prostate cancer patients," Urology 68 (Supplement 5A) (2006).
Jensen, Peptide Synthesis and Applications, 1047 Methods in Molecular Biology (Jensen et al., eds.) (2013) (252 pgs).
Kaneti et al., "Thorpe-Ingold effects in cyclizations to five-membered and six-membered rings containing planar segments. The rearrangement of N(1)-alkylsubstituted dihydroorotic acids to hydantoinacetic acids in base," Org. Biomol. Chem. 2:1098-1103 (2004).
Klotz et al., "Disease Control Outcomes from Analysis of Pooled Individual Patient Data from Five Comparative Randomised Clinical Trials of Degarelix Versus Luteinizing Hormone-releasing Hormone Agonists," European Urology 66:1101-1108 (2014).
Koedjikov et al., "B-Ureido Acid and Dihydrouracils. Part 15. Effect Of Allylic Strain on Ring Opening Of 1,6-Disubstituted Dihydrouracils" Journal Chemical Society Perkin Transactions II 1077-1081 (1984).
Lee et al, "Prostate-Specific Antigen Doubling Time Predicts Clinical Outcome and Survival in Prostate Cancer Patients Treated with Combined Radiation and Hormone Therapy" Int J Radiation Oncology 63:456-462, 2005.
Lupron Depot Prescribing Information (2019).
M. Bolla et al., Improved Survival in Patients with Locally Advanced Prostate Cancer Treated with Radiotherapy And Goserelin, N. Eng. J. Med., 337(5)295-300 (1997).
Mason et al., "Neoadjuvant Androgen Deprivation Therapy for Prostate Volume Reduction, Lower Urinary Tract Symptom Relief and Quality of Life Improvement in Men with Intermediate- to High-risk Prostate Cancer: A Randomised Non-inferiority Trial of Degarelix versus Goserelin plus Bicalutamide", Clinical Oncology 25 (2013) 190-196.
Medline Encyclopedia: ALP.
Non-Final Office Action received in U.S. Appl. No. 17/710,889 dated Oct. 4, 2022.
Non-Final Office Action on U.S. Appl. No. 17/710,899 dated Aug. 18, 2022.
Price, Highlights from the 29th European Society for Medical Oncology Congress, Vienna, Austria Oct. 29 through Nov. 2, 2004—Update on the 36-Month Data from the Phase 111 Trial D9901 of Proveoge® Immunotherapy hi Prostate Cancer, Clin Prostate Cancer 3: 136-140 (Dec. 2004).
Proteins and Proteomics: A Laboratory Manual 1st Edition by Richard J. Simpson Publisher: Cold Spring Harbor Laboratory Pr; 1st edition (Dec. 1, 2002)—"Reversed-phase High-performance Liquid Chromatography" (284 pages).
Rahimy et al, "Suppression of Plasma Testosterone and Prostate Carcinoma Size by a Redox-Based, Brain-Targeted Estrogen Delivery System in the Rat" Prostate 23:79-90, 1993.
Sep. 26, 2022 PIV Letter (Redacted).
Ruczynski et al., "Problem of Aspartimide Formation in Fmoc-Based Solid-Phase Peptide Synthesis Using Dmab Group To Protect Side Chain Of Aspartic Acid" J. Peptide Sci. 14:335-341 (2008).
Shore et al., "Oral Relugolix for Androgen-Deprivation Therapy in Advanced Prostate Cancer," N Engl J Med 382:2187-96 (2020).
Studer et al, Using PSA to Guide Timing of Androgen Deprivation in Patients with T0-4 N0-2 M0 Prostate Cancer not Suitable for Local Curative Treatment (EORTC 30891) Eur Urol, 53, 941-949, 2008.
Szczepanska et al., "Efficient Method for the Concentration Determination of Fmoc Groups Incorporated in the Core-Shell Materials by Fmoc-Glycine," Molecules 25:3983 (2020).
Takeuchi et al., "Urinary pyridinoline and deoxypyridinoline as potential markers of bone metastasis in patients with prostate cancer," J. Urol. 156:1691-1695 (1996).
Tanriverdi et al., "Expression of Gonadotropin-Releasing Hormone Type-I (GnRH-I) and Type-II (GnRH-II) in human peripheral blood mononuclear cells (PBMCs) and regulation of B-Lymphoblastoid cell proliferation by GnRH-I and GnRH-II," Exp Clin Endocrinol Diabetes 112:587-594 (2004).
The Practical Guide, Identification, Evaluation, and Treatment of Overweight and Obesity in Adults, NHLBI Obesity Education Initiative, National Institutes of Health, Oct. 2000.
Tofteng et al., "Effect of Residual Water and Microwave Heating on the Half-Life of the Reagents and Reactive Intermediates in Peptide Synthesis" Journal of European Chemistry (2012).
U.S. Appl. No. 17/710,905, filed Mar. 31, 2022, Bo-Eric Persson.
U.S. Appl. No. 17/710,889, filed Mar. 31, 2022, Tine Kold Olesen.
U.S. Appl. No. 17/710,899, filed Mar. 31, 2022, Egbert A. Van der Meulen.
U.S. Appl. No. 17/829,134, filed May 31, 2022, Bo-Eric Persson.
Gittelman et al., "A 1-Year, Open Label, Randomized Phase II Dose Finding Study of Degarelix for the Treatment of Prostate Cancer in North America," J Urol, vol. 180, pp. 1986-1992 (Nov. 2008).
Non-Final Office Action dated Jun. 3, 2022, in U.S. Appl. No. 17/710,905.
Van Poppel et al., "Long-Term Evaluation of Degarelix, A gonadotrophin-Releasing Hormone (GNRH) Receptor Blocker, Investigated in a Multicentre Randomised Study in Prostate Cnacner (CAP) Patients," Eur Urol. Suppl. 6(2): 28, 2007.

METHOD OF TREATING PROSTATE CANCER WITH GNRH ANTAGONIST

CROSS-REFERENCE TO RELATED APPLICATIONS

This application is a continuation of application Ser. No. 15/205,108, filed Jul. 8, 2016, now U.S. Pat. No. 10,695,398, issued Jun. 30, 2020, which is a continuation of Ser. No. 13/458,330, filed Apr. 27, 2012, now U.S. Pat. No. 9,415,085, issued Aug. 16, 2016; the entire contents of all the referenced applications are incorporated herein by reference.

Prostate cancer is a leading cause of morbidity and mortality for men in the industrialized world. The American Cancer Society estimates that during 2007 about 218,890 new cases of prostate cancer will have been diagnosed in the United States alone. Prostate cancer is the second leading cause of cancer death in American men, behind only lung cancer. However, while about 1 man in 6 will be diagnosed with prostate cancer during his lifetime, only 1 man in 35 will actually die of it. The American Cancer Society estimates that 27,050 men in the United States will die of prostate cancer in 2007. Prostate cancer accounts for about 9% of cancer-related deaths in men.

While prostate cancer incidence rates rose dramatically in the late 1980s, much of this increase is thought to reflect improvements in detection and diagnosis through widespread use of prostate-specific antigen (PSA) testing. Indeed, the incidence of prostate cancer has been declining since the early 1990s, and mortality rates for prostate cancer have also declined since the early 1990s (see SEER Program and the National Center for Health Statistics (seer.cancer.gov). More than 9 out of 10 prostate cancers are found in the local and regional stages (local means it is still confined to the prostate; regional means it has spread from the prostate to nearby areas, but not to distant sites, such as bone). When compared to men of the same age and race who do not have cancer (relative survival), the 5-year relative survival rate for these men is nearly 100%, however the 5-year relative survival rate for men whose prostate cancers have already spread to distant parts of the body at the time of diagnosis is only about 32%. It is estimated that approximately $8 billion is spent on prostate cancer treatment each year in the United States alone (Cancer Trends Progress Report (progressreport.cancer.gov)).

The majority of prostate cancers are dependent on testosterone for growth, and the current medical management of advanced prostate cancer involves androgen deprivation, which may be achieved by bilateral orchiectomy or by administration of gonadotrophin releasing hormone (GnRH) receptor agonists. Removal of the testes (castration) was for many years the standard method of preventing the secretion of male hormones by the gonads as a means for reducing growth of prostate cancers. More recently, secretion of male hormones has been perturbed by chemical means by interfering with production of luteinizing hormone (LH), which regulates the synthesis of the androgens. Evidence from randomized studies strongly suggests that early endocrine therapy in non-metastatic, locally advanced disease with or without lymph node metastases is associated with a survival benefit (see Granfors et al. (1998) *J. Urol.* 159:2030-34; Messing et al. (1999) *N. Eng. J. Med.* 341:1781-88; and (1997) *Br. J. Urol.* 79:235-46).

Gonadotrophin releasing hormone (GnRH) is a natural hormone produced by the hypothalamus that interacts with a receptor in the pituitary to stimulate production of LH. To decrease LH production, agonists of the GnRH receptor (GnRH-R), such as leuprolide and goserelin, have been developed. Such GnRH agonists are generally analogs of GnRH, the decapeptide pyroGlu-His-Trp-Ser-Tyr-Gly-Leu-Arg-Pro-Gly-NH$_2$. For example, GnRH agonists having a D-isomer instead of Gly in the 6-position have greater binding affinity/strength to the receptor and greater biological potency than the native hormone; one example is the [D-Ala$^6$]-GnRH (described in U.S. Pat. No. 4,072,668) having the following formula: pGlu-His-Trp-Ser-Tyr-D-Ala-Leu-Arg-Pro-Gly-NH$_2$. Such GnRH-R agonists initially act to stimulate LH release and only after prolonged treatment act to desensitize GnRH-R such that LH is no longer produced. The initial stimulation of LH production by the agonist leads to an initial surge in the production of male sex hormones such that the initial response to agonist therapy is aggravation, rather than amelioration, of the patient's condition (e.g., tumor growth may increase). This phenomenon, known as the "testosterone surge" or "flare reaction," can last for as long as two to four weeks. Additionally, each successive administration of the agonist can cause an additional small LH surge (known as the "acute-on chronic" phenomenon) that can further worsen the condition. The testosterone surge stimulates prostate cancer and can lead to a worsening of current symptoms or appearance of new symptoms such as spinal cord compression, bone pain and urethral obstruction (Thompson et al. (1990) *J. Urol.* 140: 1479-80; Boccon-Gibod et al. (1986) *Eur. Urol.* 12: 400-402). One approach that has been taken to avoid this problem has been to combine administration of a GnRH-R agonist with an antiandrogen, such as flutamide, known as total androgen ablation therapy (AAT). Hormonal therapy with an GnRH-R agonist in combination with an antiandrogen has been used as a pre-treatment prior to radical prostatectomy known as adjuvant therapy. The use of antiandrogens, however, is associated with serious hepatic and gastrointestinal side effects.

Antagonists of the gonadotrophin releasing hormone receptor (GnRH-R) have been developed to overcome the "testosterone surge" or "flare reaction" associated with GnRH agonists. However, GnRH antagonist peptides are frequently associated with the occurrence of histamine-releasing activity. This histamine-releasing activity represents a serious obstacle to the clinical use of such antagonists because histamine release results in adverse side effects such as edema and itching.

The search for improved GnRH antagonists has resulted in the making of Antide, i.e. [Ac-D-2Nal$^1$, D-4ClPhe$^2$, D-3Pal$^3$, Lys(Nic)$^5$, D-Lys(Nic)$^6$, ILys$^8$, D-Ala$^{10}$]-GnRH; and Cetrorelix, i.e. [Ac-D-2Nal$^1$, D-4ClPhe$^2$, D-3Pal$^3$, D-Cit$^6$, D-Ala$^{10}$]-GnRH. U.S. Pat. No. 5,516,887 describes GnRH antagonists which are said to be more effective than Antide in suppressing plasma testosterone, e.g. [Ac-D-2Nal$^1$, D-4ClPhe$^2$, D-3Pal$^3$, D-N$^\varepsilon$-carbamoyl Lys$^6$, Ilys$^8$, D-Ala$^{10}$]-GnRH, which is referred to as Antarelix. Furthermore, U.S. Pat. No. 5,296,468 discloses the design and synthesis of a number of GnRH antagonists wherein the side chains of selected residues are reacted to create cyanoguanidino moieties, some of which subsequently spontaneously convert to a desired heterocycle, e.g. a 3-amino-1,2,4-triazole(atz). Such cyanoguanidino moieties are built upon the omega-amino group in an amino acid side chain, such as lysine, ornithine, 4-amino phenylalanine (4Aph) or an extended chain version thereof, such as 4-amino homophenylalanine (4Ahp). GnRH antagonists having such significantly modified or unnatural amino acids in the 5- and 6-positions exhibit good biological potency, and those built upon Aph are generally considered to be particularly potent.

One that is especially useful is Azaline B, i.e. [Ac-D-2NaI$^1$, D-4CIPhe$^2$, D-3PaI$^3$, 4Aph(atz)$^5$, D-4Aph(atz)$^6$, ILys$^8$, D-Ala$^{10}$]-GnRH. U.S. Pat. No. 5,506,207 discloses biopotent GnRH antagonists with acylated, amino-substituted phenylalanine side chains of residues in the 5- and 6-positions; one such decapeptide is Acyline, i.e. [Ac-D-2NaI$^1$, D-4CIPhe$^2$, D-3PaI$^3$, 4Aph(Ac)$^5$, D-4Aph(Ac)$^6$, ILys$^8$, D-Ala$^{10}$]-GnRH. Despite the attractive properties of this group of GnRH antagonists, the search has continued for still further improved GnRH antagonists, particularly those which exhibit long duration of biological action. It can frequently be important that a peptide analog should exhibit a long duration of activity with respect to LH secretion, a property which may be enhanced by the peptide's resistance to proteolytic enzyme degradation in the body for both short-term and long-term treatment indications. In addition, to facilitate administration of these compounds to mammals, particularly humans, without significant gelling, it is considered extremely advantageous for such GnRH antagonistic decapeptides to have high solubility in water at normal physiologic pH, i.e. about pH 5 to about pH 7.4.

While the use of both GnRH agonist and antagonists in androgen deprivation therapy to treat prostate cancer has yielded promising results, there are concerns about the relative safety of the available drugs. For example, the GnRH abarelix was found to carry a risk of serious allergic reactions, including anaphylaxis with hypotension and syncope, and was also found to lose efficacy over the course of treatment in some cases. Indeed, Abarelix™ (Plenaxis™ in the U.S.) was eventually approved, but only for patients with advanced prostate cancer, and was eventually withdrawn from the market in 2005 for commercial reasons apparently related to these problems. Furthermore, while prostate cancer-specific mortality has been decreasing, there has been little overall effect on mortality in this group, suggesting the possibility of an increased risk of death from nonprostate cancer related causes. In particular, it has been suggested that certain androgen deprivation therapies could adversely affect cardiovascular health (see Yannucci et al. (2006) *J. Urology* 176:520-525; and Etzioni et al. (1999) *J. Natl. Canc. Inst.* 91:1033).

Androgen deprivation therapy (ADT) induced by GnRH agonists is gaining increased use in not only metastatic but also in locally advanced prostate cancer (PCa) patients. (see Gilbert et al. (2011) *Urol. Oncol.* 29:647-53; and Shahinian et al. (2005) *Cancer* 103:1615-1624.) With increasing experience with the use of agonists in earlier stage disease, concerns have emerged about the relative importance of a variety of adverse effects, including osteoporosis, diabetes, and as discussed above, certain cardiovascular (CV) events. (Saylor et al. (2010) *J. Natl. Compr. Canc. Netw.* 8:211-23.) While the increased risk of diabetes and osteoporosis (both driven by androgen deprivation) is a consistent finding across different studies and forms of ADT (Taylor et al (2009) *Cancer* 115:2388-99), the increased risk of CV events posed by GnRH agonists is still a subject of debate, even after addition of this safety issue to the label of these drugs. Variation in study designs including differences in study populations, differences in the reference group, the number and type of CV events analyzed, and the follow-up time are likely contributors to the apparent controversies (Alibhai et al. (2009) *J. Clin. Oncol.* 27:3452-8; Razzak (2012) *Nat. Rev. Urol.* 9:61; Levine et al. (2010) *Circulation* 121:833-40; and Van Poppel et al. (2011) 3:49-55). Another limitation of obtaining clarity has been the lack of a plausible hypothesis concerning the mechanism of action driving the rise of CV complications. Nevertheless, there are some preliminary observations suggesting that advanced age and history of CV events increase the probability of capturing the CV harm of GnRH agonists (Keating et al. (2006) *J. Clin. Oncol.* 24:4448-56; Keating et al. (2009) *J. Natl. Cancer Inst.* 1-8; Saigal et al. (2007) *Cancer* 110:1493-500; Hayes et al. (2010) *BJU Int.* 106:979-85; and Nanda et al. (2009) *JAMA* 302:866-73).

The fact that GnRH agonists remain by far the most extensively used form of medical ADT explains why there is a tendency to use GnRH agonists and ADT as synonyms. Only few investigators have raised the notion that the CV harm of GnRH agonists could also be mediated by triggering of GnRH receptors instead of the effects of testosterone deprivation (Dong et al. (2011) *J. Neuroendocrinol* 23:456-63). This line of thinking comes from reports suggesting that stand-alone antiandrogens do not seem to confer CV harm (Keating et al. (2009) *J. Natl. Cancer Inst.* 1-8 and Robinson et al. (2012) *Int. J. Cancer* 130:478-87). Degarelix, a GnRH antagonist opens a unique possibility to obtain further insights into the role of GnRH receptors. A previous analysis on 1704 degarelix-treated PCa patients participating in clinical trials, demonstrated comparable CV event rates before and after treatment initiation (Smith et al. (2011) *J. Urol.* 186:1835-42), suggesting no CV harm. However, ultimate answers to whether the CV safety profile of antagonist is distinct from agonists can only come from direct comparison of these classes in randomized clinical trials.

Accordingly, new therapeutic regiments for prostate cancer are needed that are free of both the adverse consequences of the GnRH agonist testosterone spike, as well as the undesirable side effects of available GnRH antagonist therapies. It is also beneficial to conduct a direct comparison of antagonists and agonists in randomized clinical trials to determine whether the cardiovascular safety profile of antagonist is distinct from agonists.

SUMMARY OF THE INVENTION

Applicants have found that a relatively low dose of degarelix GnRH antagonist, delivered about once every 28 days (e.g., monthly), can safely and rapidly suppress testosterone levels to therapeutic levels in prostate cancer patients, without causing a testosterone spike and with an appreciably diminished risk of causing an undesirable side effect associated with androgen deprivation therapy such as a cardiac disorder, arthralgia, and/or a urinary tract infection.

In one aspect, the invention provides a method of treating prostate cancer in a subject with a reduced likelihood of causing a testosterone spike or other side effect of a gonadotrophin releasing hormone (GnRH) agonist therapy. The method includes administering an initial dose of about 240 mg of degarelix to the subject; and administering a maintenance dose of about 80 mg of degarelix to the subject once every approximately 28 days thereafter, and thereby treating prostate cancer in the subject with a reduced likelihood of causing a testosterone spike or other GnRH agonist side effect.

In a further aspect, the invention provides a method of treating prostate cancer in a subject with a reduced likelihood of causing a testosterone spike or other side effect of a gonadotrophin releasing hormone (GnRH) agonist therapy. The method includes administering an initial dose of 160-320 mg of degarelix to the subject; and administering a maintenance dose of 60-160 mg of degarelix to the subject once every 20-36 days thereafter, and thereby treating prostate cancer in the subject with a reduced likelihood of causing a testosterone spike or other GnRH agonist side effect.

In certain embodiments of these methods of the invention, the maintenance dose is administered monthly. In further embodiments, the treated subject has a decreased likelihood of developing or experiencing an undesirable side effect during treatment compared to treatment with the gonadotrophin releasing hormone (GnRH) agonist leuprolide. In particular embodiments, the treated subject has a decreased likelihood of developing or experiencing a cardiovascular side effect such as a myocardial infarction, chest pain, a cardiac murmur or a vascular side effect (e.g., deep vein thrombosis (DVT)) during treatment compared to treatment with the gonadotrophin releasing hormone (GnRH) agonist leuprolide. In further embodiments, the methods provide the treated subject with a decreased likelihood of developing a side effect selected from the group consisting of a cardiac arrhythmia, a coronary artery disorder, and a cardiac disorder. In particularly useful embodiments, the treated subject has a body mass index (BMI) of less than 30 kg/m$^2$, particularly a BMI of less than 25 kg/m$^2$. In further useful embodiments the treated subject has a cholesterol level of greater than or equal to 4 mmol/L (155 mg/dL).

In further embodiments, the methods of the invention are used to treat a subject who is at risk for cardiovascular disease. In particularly useful embodiments, the methods of the invention further include the step of identifying a prostate cancer subject who is also at risk for cardiovascular disease for treatment by the method.

In still further embodiments, the treated subject has a decreased likelihood of developing or experiencing an increase in arthralgia and/or musculoskeletal stiffness during treatment compared to treatment with the gonadotrophin releasing hormone (GnRH) agonist leuprolide. In particularly useful embodiments thereof, the treated subject has locally advanced prostate cancer and/or is less than 65 years old.

In further embodiments, the treated subject has a decreased likelihood of developing a musculoskeletal disorder and/or a connective tissue disorder during treatment compared to treatment with the gonadotrophin releasing hormone (GnRH) agonist leuprolide. In particular embodiments, the musculoskeletal disorder and/or a connective tissue disorder is arthralgia. In other embodiments, the musculoskeletal disorder and/or a connective tissue disorder is musculoskeletal stiffness.

In still further embodiments of these methods of the invention, the treated subject has a decreased likelihood of developing noninfective cystitis during treatment compared to treatment with the gonadotrophin releasing hormone (GnRH) agonist leuprolide.

In another embodiment, the treated subject has a decreased likelihood of developing a urinary or renal system disorder compared to treatment with the gonadotrophin releasing hormone (GnRH) agonist leuprolide. In certain embodiments, the urinary or renal system disorder is a urinary tract infection. In particularly useful embodiments thereof, the treated subject has locally advanced prostate cancer. In another embodiment, the urinary or renal system disorder is an increase in urinary retention. In still another embodiment, the urinary or renal system disorder is a noninfective cystitis.

In still other embodiments, the treated subject has a decreased likelihood of developing erectile dysfunction during treatment compared to treatment with the gonadotrophin releasing hormone (GnRH) agonist leuprolide. In other embodiments, the treated subject has a decreased likelihood of decreased libido during treatment compared to treatment with the gonadotrophin releasing hormone (GnRH) agonist leuprolide.

In particular embodiments of the above methods of the invention, the treated subject has at least about a 95% likelihood of maintaining a therapeutically low serum testosterone level of less than or equal to 0.5 ng/mL by day 28 of treatment. In certain embodiments, the treated subject has at least about a 95% likelihood of maintaining a therapeutically low serum testosterone level of less than or equal to 0.5 ng/mL from day 28 through day 364 of treatment. In still further embodiments, the treated subject has at least about a 30% decrease in prostate specific antigen (PSA) by day 14 of treatment. In particular embodiments, the treated subject has at least about a 50% decrease in prostate specific antigen (PSA) by day 14 of treatment. In further embodiments, the treated subject has at least about a 60% decrease in prostate specific antigen (PSA) by day 28 of treatment. In still further embodiments, the treated subject has at least about a 75% decrease in prostate specific antigen (PSA) by day 28 of treatment.

In further embodiments of the method of the invention, the treated subject has at least about an 80% (e.g., a 95%) likelihood of maintaining a low prostate specific antigen (PSA) level of less than about 5 ng/mL during treatment.

In further embodiments of the method of the invention, the treated subject has locally advanced prostate cancer and has at least about a 40% decrease in PSA by day 14 of treatment.

In still further embodiments, the treated subject has metastatic prostate cancer and has at least about a 60% decrease in PSA by day 14 of treatment.

In particular embodiments of the above methods of the invention, the treated subject has a body mass index of less than 30 kg/m$^2$ (especially less than 25 kg/m$^2$).

In another aspect, the invention provides methods of treating prostate cancer in a subject at risk for a cardiovascular disease or disorder by administering a therapeutically effective dose of degarelix to the subject with prostate cancer who is at risk for a cardiovascular disease or disorder. In particular embodiments, the therapeutically effective dose includes an initial starting dose of 160 to 320 mg of degarelix, and a monthly maintenance dose of 60 to 160 mg of degarelix. In further embodiments, the therapeutically effective dose of degarelix includes a maintenance dose of about 80 mg of degarelix once every approximately 28 days of treatment. In certain embodiments thereof, the therapeutically effective dose of degarelix further includes a single initial dose of about 240 mg of degarelix at the start of treatment.

In particular embodiments, the subject treated has been identified to be at risk of a specific cardiovascular disease or disorder such as cardiac murmur, atrioventricular blockage, and/or myocardial ischemia.

In further embodiments, the treated subject possesses an indicator of increased risk for cardiovascular disease, e.g. high blood pressure, high low-density lipoprotein cholesterol, low high-density lipoprotein cholesterol, high serum glucose and/or a habitual smoking habit. In particular embodiments, the treated subject has high blood pressure of greater than or equal to 130 over 85 mm Hg. In further embodiments, the treated subject smokes cigarettes daily. In still further embodiments, the treated subject has an elevated level of low-density lipoprotein cholesterol of greater than or equal to about 160 mg/dl. In further embodiments, the treated subject has a low level of high-density lipoprotein cholesterol of less than 35 mg/dl. In other embodiments, the treated subject has an elevated fasting glucose level of greater than about 120 mg/dL.

In still other particularly useful embodiments, the treated subject possesses an indicator of increased risk for cardiovascular disease such as high serum C-reactive protein (CRP), high serum homocysteine, high serum fibrinogen, and/or high serum lipoprotein(a) (Lp(a)). In particular embodiments, the treated subject has an elevated level of C-reactive protein of greater than 3 mg/dL. In other embodiments, the treated subject has an elevated level of serum homocysteine of greater than 30 μmol/L. In further embodiments, the treated subject has an elevated level of serum fibrinogen of greater than 7.0 g/L. In still further embodiments, the treated subject has an elevated level of serum Lp(a) of greater than 30 mg/dL.

In certain embodiments, the treated subject has a body mass index of less than 30 kg/m$^2$ (particularly less than 25 kg/m$^2$).

In further embodiments, the treated subject has a decreased likelihood, compared to treatment with the gonadotrophin releasing hormone (GnRH) agonist leuprolide, of developing a cardiovascular side effect such as cardiac arrhythmia, coronary artery disorder, and/or a cardiac disorder. In particular embodiments thereof, the treated subject has a body mass index (BMI) of less than 30 kg/m$^2$ (especially less than 25 kg/m$^2$). In other embodiments, the treated subject has a cholesterol level of greater than or equal to 4 mmol/L (155 mg/dL).

In still another aspect, the invention provides a method of treating prostate cancer in a subject at risk for a cardiovascular disease or disorder by first identifying a suitable subject with prostate cancer that is also at risk for a cardiovascular disease or disorder. The suitable subject with cardiovascular disease risk is then administered an initial dose of about 240 mg of degarelix, followed by a maintenance dose of about 80 mg of degarelix once every approximately 28 days thereafter, thereby treating prostate cancer in the subject at risk for a cardiovascular disease or disorder. In certain embodiments, the maintenance dose of degarelix is administered monthly.

In a further aspect, the invention provides a method of treating prostate cancer in a subject at risk for a cardiovascular disease or disorder by first identifying a suitable subject with prostate cancer and at risk for a cardiovascular disease or disorder. The suitable subject with cardiovascular disease risk is then administered an initial dose of 160-320 mg of degarelix, followed by a maintenance dose of 60-160 mg of degarelix delivered once every approximately 28 days thereafter, thereby treating prostate cancer in the subject at risk for a cardiovascular disease or disorder with a reduced likelihood of causing a testosterone spike or other GnRH agonist side-effect. In certain embodiments, the maintenance dose of degarelix is administered monthly. In particular embodiments of this aspect, the treated subject has a body mass index of less than 30 kg/m$^2$ (particularly a BMI of less than 25 kg/m$^2$). In further embodiments, the treated subject is at risk of a cardiovascular disease or disorder, such as a cardiac murmur, an atrioventricular blockage, and/or myocardial ischemia. In still other embodiments, the treated subject possesses an indicator of increased risk for cardiovascular disease. In further particular embodiments, the treated subject possesses an indicator of increased risk for cardiovascular disease, e.g. high blood pressure, high low-density lipoprotein cholesterol, low high-density lipoprotein cholesterol, high serum glucose and/or a habitual smoking habit. In particular embodiments, the treated subject has high blood pressure of greater than or equal to 130 over 85 mm Hg. In further embodiments, the treated subject smokes cigarettes daily. In still further embodiments, the treated subject has an elevated level of low-density lipoprotein cholesterol of greater than or equal to about 160 mg/dL. In further embodiments, the treated subject has a low level of high-density lipoprotein cholesterol of less than 35 mg/dl. In other embodiments, the treated subject has an elevated fasting glucose level of greater than about 120 mg/dL.

In still other embodiments, the treated subject possesses an indicator of increased risk for cardiovascular disease such as high serum C-reactive protein (CRP), high serum homocysteine, high serum fibrinogen, and/or high serum lipoprotein(a) (Lp(a)). In particular embodiments, the treated subject has an elevated level of C-reactive protein of greater than 3 mg/dL. In other embodiments, the treated subject has an elevated level of serum homocysteine of greater than 30 μmol/L. In further embodiments, the treated subject has an elevated level of serum fibrinogen of greater than 7.0 g/L. In still further embodiments, the treated subject has an elevated level of serum Lp(a) of greater than 30 mg/dL. In other embodiments, the treated subject has a decreased likelihood, when compared to treatment with the gonadotrophin releasing hormone (GnRH) agonist leuprolide, of developing a cardiovascular side effect such as a cardiac arrhythmia, a coronary artery disorder, and/or a cardiac disorder. In certain embodiments thereof, the treated subject has a body mass index of less than 30 kg/m$^2$ (particularly less than 25 kg/m$^2$).

In yet another aspect, the invention provides a method of treating prostate cancer in a preferred subject by identifying a subject with prostate cancer having a body mass index of less than about 25 kg/m$^2$. The preferred subject thus identified is administered a single initial dose of 160-320 mg of degarelix, followed by monthly doses of 60-160 mg of degarelix administered once every 20-36 days thereafter. In certain embodiments, the treated subject has a decreased likelihood, when compared to treatment with the gonadotrophin releasing hormone (GnRH) agonist leuprolide, of developing a cardiovascular side effect such as a cardiac arrhythmia, a coronary artery disorder, and/or a cardiac disorder. In particular embodiments, the initial dose of degarelix is about 240 mg, and the maintenance dose of degarelix is about 80 mg administered monthly. In further particular embodiments, the preferred subject has a cholesterol level of greater than or equal to 4 mmol/L (155 mg/dL).

In further embodiments, the methods of treatment of the invention may be with, or associated with, a reduced incidence or likelihood of one or more of cardiovascular and/or vascular side effects (for example with reduced incidence and/or likelihood of one or more of myocardial infarction, chest pain, chest pain development, cardiac murmur, cardiac murmur development, myocardial ischemia, atrioventricular blockage, deep vein thrombosis (DVT), cardiac arrhythmia, coronary artery disorder, and/or cardiac disorder), musculoskeletal disorder (for example arthralgia and/or musculoskeletal stiffness), connective tissue disorder, urinary and/or renal system disorder.

In an additional embodiment, the present disclosure provides a method of treating prostate cancer in a subject who has had at least one cardiovascular event, wherein administration of degarelix to the subject decreases the likelihood of developing or experiencing an additional cardiovascular event compared to treatment with a gonadotrophin releasing hormone (GnRH) agonist.

DETAILED DESCRIPTION OF THE INVENTION

Figure 1:
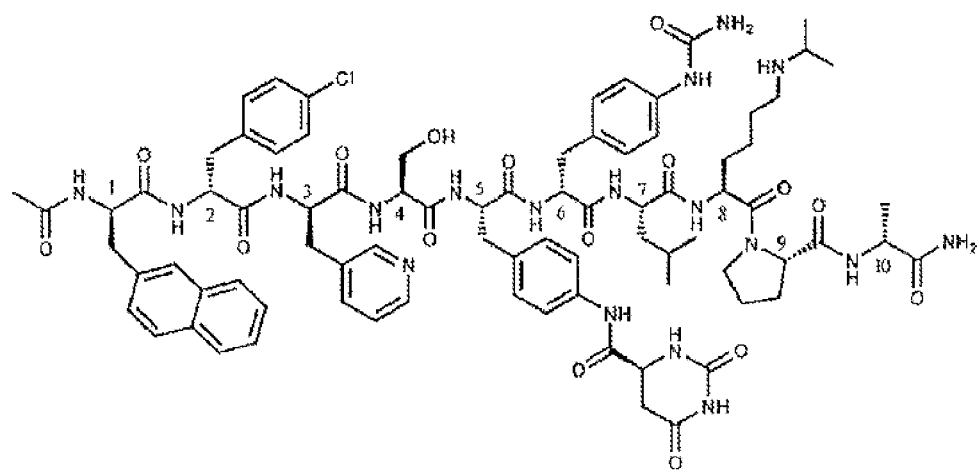
FIG. 1 is a depiction of the chemical structure of degarelix.

Particular aspects of the invention are described in greater detail below. The patent and scientific literature referred to herein are hereby incorporated by reference.

General

In general, the invention provides methods of treating prostate cancer with degarelix GnRH antagonist using a dosing regimen that results in optimal efficacy, and reduced serious side-effects, particularly in certain patient subgroups, compared to other androgen deprivation therapies, particularly GnRH agonist therapies such as leuprolide.

The relative efficacy and safety (including adverse side effects) of the GnRH agonist therapy leuprolide (also leuprorelin or LUPRON) is known in the art (see e.g., Persad (2002) *Int. J. Clin. Pract.* 56:389-96; Wilson et al. (2007) *Expert Opin. Invest. Drugs* 16:1851-63; and Berges et al. (2006) *Curr. Med. Res. Opin.* 22:649-55). In addition, the relative efficacy and safety of the GnRH antagonist therapy abarelix (PLENAXIS) has also been reported (see, e.g., Mongiat-Artus et al. (2004) *Expert Opin. Pharmacother.* 5:2171-9; and Debruyne et al. (2006) *Future Oncol.* 2:677-96). A review of the basic methods for conducting and analyzing the type of controlled clinical studies described herein, including analyses of safety, efficacy and selective advantages to certain patient subpopulations, is available (see Spilker (1991) *Guide to Clinical Trials* Raven Press, New York; and Spilker (1996) *Quality of Life and Pharmacoeconomics in Clinical Trials* Lippincott—Raven Publishers New York).

Definitions

The singular forms "a," "an," and "the" include plural reference unless the context clearly dictates otherwise.

As used herein, the term "ADR" refers to an adverse drug reaction, and the term "AE" refers to an "adverse event."

The terms "approximately" and "about" mean to be nearly the same as a referenced number or value. As used herein, the terms "approximately" and "about" should be generally understood to encompass ±10% a specified amount, frequency or value.

The term "agonist" as used herein, is meant to refer to an agent that mimics or up-regulates (e.g., potentiates or supplements) the bioactivity of a protein. An agonist can be a wild-type protein or derivative thereof having at least one bioactivity of the wild-type protein.

"Antagonist" as used herein is meant to refer to an agent that down-regulates (e.g., suppresses or inhibits) at least one bioactivity of a protein.

As used herein, the term "arthralgia" refers to pain in one or more joints, which may occur as a symptom of injury, infection, illnesses—in particular arthritis—or an allergic reaction to medication. In distinguishing the term "arthralgia" from the term "arthritis" it should be noted that "arthralgia" specifically refers to non-inflammatory conditions, and the term "arthritis" should be used when the condition is an inflammatory condition.

The term "body mass index" (BMI) refers to a statistical measure of the weight of a person scaled according to height, which is an approximating measure of the relative percentages of fat and muscle mass in the human body. BMI is defined as the individual's body weight divided by the square of their height, and the formulas used in medicine produce a unit of measure of $kg/m^2$.

The term "CI" refers to a statistical confidence interval and the term "HR" refers to hazard rate(s).

The term "CV" refers to a cardiovascular.

The term "cardiovascular" as used herein refers to conditions involving the heart and/or blood vessels.

The term "cardiac arrhythmia" as used herein is any of a group of conditions in which the electrical activity of the heart is irregular or is faster or slower than normal.

As used herein, the terms "coronary artery disorder" or "coronary artery disease" refers to a condition (such as sclerosis or thrombosis) that reduces the blood flow through the coronary arteries to the heart muscle.

The term "cardiac disorder" as used herein refers to any of a number of abnormal organic conditions affecting the heart including coronary heart disease, heart attack, cardiovascular disease, pulmonary heart disease and high blood pressure.

The term "deep-vein thrombosis" (also known as deep-venous thrombosis or DVT) is the formation of a blood clot ("thrombus") in a deep vein. Deep-vein thrombosis commonly affects the leg veins, such as the femoral vein or the popliteal vein or the deep veins of the pelvis. Occasionally the veins of the arm are affected (known as Paget-Schrötter disease). Thrombophlebitis is the more general class of pathologies of this kind. There is a significant risk of the thrombus embolizing and traveling to the lungs causing a pulmonary embolism.

The term "ECG" refers to an electrocardiogram.

The term "MedDRA" refers to the Medical dictionary for regulatory activities.

The term "myocardial infarction" refers to an infarction of the myocardium that results typically from coronary occlusion, which may be marked by sudden chest pain, shortness of breath, nausea, and loss of consciousness, and sometimes death. An "infarction" refers to the process of forming an infarct, which is an area of necrosis in a tissue or organ resulting from obstruction of the local circulation by a thrombus or embolus.

"Male sexual dysfunction" includes impotence, loss of libido, and erectile dysfunction. "Erectile dysfunction" is a disorder involving the failure of a male mammal to achieve erection, ejaculation, or both.

The term "prostate cancer" refers to any cancer of the prostate gland in which cells of the prostate mutate and begin to multiply out of control. The term "prostate cancer" includes early stage, localized, cancer of the prostate gland; later stage, locally advanced cancer of the prostate gland; and later stage metastatic cancer of the prostate gland (in which the cancer cells spread (metastasize) from the prostate to other parts of the body, especially the bones and lymph nodes).

The term "prostate-specific antigen" or "PSA" refers to a protein produced by the cells of the prostate gland that is present in small quantities in the serum of normal men, but is often elevated in the presence of prostate cancer and in other prostate disorders. A blood test to measure PSA is the most effective test currently available for the early detection of prostate cancer. Higher than normal levels of PSA are associated with both localized and metastatic prostate cancer (CaP).

The term "PD" refers to pharmacodynamic, and the term "PK" refers to pharmacokinetic.

The term "PT" refers to a preferred term.

The term "SAE" refers to a serious adverse event".

The term "SD" refers to standard deviation.

The term "SOC" refers to a system organ class.

The term "SUSAR" refers to a suspected, unexpected serious adverse reaction.

A "subject" or "patient" is a male mammal, more preferably a human male. Non-human male mammals include, but are not limited to, farm animals, sport animals, and pets.

A "urinary tract infection" (UTI) is a bacterial infection that affects any part of the urinary tract, which is the tract through which urine passes and includes the renal tubules and renal pelvis of the kidney, the ureters, the bladder, and the urethra. The most common type of UTI is a bladder infection which is also often called cystitis. Another kind of UTI is a kidney infection, known as pyelonephritis, which is a more serious condition.

Degarelix and Related Pharmaceutical Formulations

Degarelix is a potent GnRH antagonist that is an analog of the GnRH decapeptide (pGlu-His-Trp-Ser-Tyr-Gly-Leu-Arg-Pro-Gly—NH$_2$) incorporating p-ureido-phenylalanines at positions 5 and 6 (Jiang et al. (2001) *J. Med. Chem.* 44:453-67). It is indicated for treatment of patients with prostate cancer in whom androgen deprivation is warranted (including patients with rising PSA levels after having already undergone prostatectomy or radiotherapy).

Degarelix is a selective GnRH receptor antagonist (blocker) that competitively and reversibly binds to the pituitary GnRH receptors, thereby rapidly reducing the release of gonadotrophins and consequently testosterone (T). Prostate cancer is sensitive to testosterone deprivation, a mainstay principle in the treatment of hormone-sensitive prostate cancer. Unlike GnRH agonists, GnRH receptor blockers do not induce a luteinizing hormone (LH) surge with subsequent testosterone surge/tumor stimulation and potential symptomatic flare after the initiation of treatment.

Degarelix is available as a powder for injectable formulation and a solvent for reconstitution of the powder. The powder for injectable formulation is a lyophilisate containing degarelix and mannitol, and the solvent consists of water for injection provided in 6 mL vials.

The active ingredient degarelix is a synthetic linear decapeptide amide containing seven unnatural amino acids, five of which are D-amino acids. The drug substance is an acetate salt, but the active moiety of the substance is degarelix as the free base. The acetate salt of degarelix is a white to off-white amorphous powder of low density as obtained after lyophilisation. The chemical name is D-Alaninamide, N-acetyl-3-(2-naphthalenyl)-D-alanyl-4-chloro-D-phenylalanyl-3-(3-pyridinyl)-D-alanyl-L-seryl-4-[[[(4S)-hexahydro-2,6-dioxo-4-pyrimidinyl]carbonyl]amino]-L phenylalanyl-4-[(aminocarbonyl)amino]-D-phenylalanyl-L leucyl-N6-(1-methylethyl)-L-lysyl-L-prolyl. It has an empirical formula of $C_{82}H_{103}N_{18}O_{16}Cl$ and a molecular weight of 1,632.3 Da.

The chemical structure is of degarelix is shown in FIG. 1 and may also be represented by the formula:

Ac-D-NaI-D-Cpa-D-PaI-Ser-Aph(Hor)-D-Aph(Cbm)-Leu-Lys(iPr)—Pro-D-Ala-NH$_2$

Degarelix is one member of a family of GnRH antagonists, described in further detail in U.S. Pat. No. 5,925,730 and EP 1003774 that carry modifications in positions 5 and 6 and have potent GnRH receptor binding activity as well as the particularly advantageous property of long duration of bioactivity. Related GnRH antagonists are known in the art and described, e.g., in U.S. Pat. Nos. 5,821,230 and 6,214,798.

Administration and Dosing

A preferred dosing regimen for treating adult males with prostate cancer is a single 240 mg starting dose of degarelix administered as two subcutaneous injections of 120 mg; and followed by monthly maintenance doses of 80 mg of degarelix administered as a single subcutaneous injection beginning approximately one month after the initial starting dose.

Degarelix may be formulated for administration subcutaneously, as opposed to intravenously, generally in the abdominal region, as described in further detail below. As with other drugs administered by subcutaneous injection, the injection site may vary periodically to adapt the treatment to injection site discomfort. In general, injections should be given in areas where the patient will not be exposed to pressure, e.g. not close to waistband or belt and not close to the ribs.

Administration of degarelix by subcutaneous or intramuscular injection works well, but daily injections are generally not acceptable and so a depot formulation of degarelix may be utilized as describe in further detail in WO 03/006049 and U.S. Pub. Nos. 20050245455 and 20040038903.

Briefly, subcutaneous administration of degarelix may be conducted using a depot technology in which the peptide is released from a biodegradable polymer matrix over a period of (typically) one to three months. Degarelix and related GnRH antagonist peptides as described in WO 03/006049 and U.S. Pub. Nos. 2005/0245455 and 2004/0038903, have a high affinity for the GnRH receptor and are much more soluble in water than other GnRH analogues. Degarelix and these related GnRH antagonists are capable of forming a gel after subcutaneous injection, and this gel can act as a depot from which the peptide is released over a period of weeks or even months.

A key variable for formation of an effective degarelix depot is the concentration of the solution in combination with the amount of substance administered per se. The concentration of the must be within a functional range. If the formulation is too dilute then no depot is formed and the long duration of action is lost, regardless of the amount of drug substance given. If the formulation is too concentrated then gel formation will occur before the drug can be administered. Effective depot-forming formulations of degarelix generally have a concentration of not less than 5 mg/mL degarelix, e.g. 5 to 40 mg/mL of degarelix. Accordingly, the dosing regimen for degarelix may be administered as an initial, starting dose of 240 mg administered as 6 mL of about 40 mg/mL (e.g., 2 injections of about 3 mL (e.g., 3.2 mL)) degarelix formulation, followed by monthly maintenance doses of 80 mg administered as a single injection of 4 mL of about 20 mg/mL degarelix formulation. Alternatively, monthly maintenance doses of 160 mg may be utilized, e.g. by administering 4 mL of about 40 mg/mL degarelix every month.

Thus, degarelix may be provided as a powder for reconstitution (with a solvent) as a solution for injection (e.g. subcutaneous injection, e.g. to form a depot as described above). The powder may be provided as a lyophilisate containing degarelix (e.g. as acetate) and mannitol. A suitable solvent is water (e.g., water for injection, or WFI). For example, degarelix may be provided in a vial containing 120 mg degarelix (acetate) for reconstitution with about 3 mL WFI (e.g., 3.2 mL) such that each mL of solution contains about 40 mg degarelix. In another example, degarelix may be provided in a vial containing 80 mg degarelix (acetate). After reconstitution with about 4 mL WFI each mL solution contains about 20 mg degarelix.

The reconstituted formulation should be a clear liquid, free of undissolved matter. A single dose of 240 mg degarelix, followed by a monthly maintenance dose of 80 mg, rapidly causes a decrease in the concentrations of the luteinizing hormone (LH), follicle stimulating hormone (FSH) and subsequently testosterone. The plasma concentration of dihydrotestosterone (DHT) decreases in a similar manner to testosterone.

Degarelix is effective in achieving and maintaining testosterone suppression well below medical castration level of 0.5 ng/mL. As described below in further detail, maintenance monthly dosing of 80 mg resulted in sustained testosterone suppression in 97% of patients for at least one year and median testosterone levels after one year of treatment were 0.087 ng/mL.

The relevant pharmacokinetic parameters for degarelix evaluated in prostate cancer patients are summarized in Table 1, below. Median degarelix trough concentrations in the maintenance phase with 80 mg at a concentration of 20 mg/mL was 10.9 ng/mL.

TABLE 1

| Declarelix pharmacokinetic parameters after subcutaneous administration of 240 mg at a concentration of 40 mg/mL | |
|---|---|
| Pharmacokinetic parameter | degarelix 240 mg |
| Cmax (ng/mL) | 53.4 |
| Tmax (days) | 1.4 |
| T½ (days) | 43 |
| AUC (day · ng/mL) | 1240 |

Following subcutaneous administration of 240 mg degarelix (6 mL at a concentration of about 40 mg/mL) to prostate cancer patients, degarelix is eliminated in a biphasic fashion, with a median terminal half-life of approximately 43 days. The long half-life after subcutaneous administration is a consequence of a very slow release of degarelix from the depot formed at the injection site(s). The pharmacokinetic behavior of the drug is strongly influenced by its concentration in the injection formulation.

The resulting distribution volume in healthy elderly men is approximately 1 L/kg. Plasma protein binding is estimated to be approximately 90%.

Degarelix is subject to common peptidic degradation during the passage of the hepato-biliary system and is mainly excreted as peptide fragments in the feces. No significant metabolites were detected in plasma samples after subcutaneous administration. In vitro studies have shown that degarelix is not a substrate for the human CYP450 system. Therefore, clinically significant pharmacokinetic interactions with other drugs are unlikely to occur.

In healthy men, approximately 20% of a given dose of degarelix was renally excreted, suggesting that approximately 80% is excreted via the hepato-biliary system in humans. The clearance in healthy elderly men is 35-50 mL/hr/kg.

Adverse Events (Side Effects)

Degarelix has been found to be generally well tolerated in clinical trials. The most commonly observed adverse reactions during degarelix therapy were due to the expected physiological effects of testosterone suppression, mainly hot flushes and increased weight, and injection site related adverse events, mainly injection site pain and injection site erythema.

In the confirmatory active-controlled clinical trial comparing degarelix subcutaneous (s.c.) with leuprolide intramuscular (i.m.) for 12 months of treatment of patients with prostate cancer, the most frequently reported side effects were adverse events occurring at the injection site including pain (28%), erythema (17%), swelling (6%), induration (4%) and nodule (3%). These adverse events were mostly transient, of mild to moderate intensity and occurred primarily with the starting dose and led to very few discontinuations (<1%). The majority of injection site adverse events did not require any treatment. Of the reported events 20% were ameliorated by the patients receiving treatment with over the counter (OTC) remedies such as analgesics or cold packs. In addition, there were a number of other frequent adverse events including weight increase, fatigue, chills, hot flush, hypertension, back pain, arthralgia, and urinary tract infection, as summarized in Table 2 below.

TABLE 2

Comparison of Most Frequent Adverse Events for degarelix versus leuprolide Treatment

| | degarelix 240/80 mg (s.c.) N = 207 % | leuprolide 7.5 mg (i.m.) N = 201 % |
|---|---|---|
| Percentage of subjects with adverse events | 79 | 78 |
| Body as a whole | | |
| Injection site adverse events** | 35 | <1 |
| Weight increase* | 9 | 12 |
| Fatigue | 3 | 6 |
| Chills | 5 | 0 |
| Cardiovascular system | | |
| Hot flush* | 26 | 21 |
| Hypertension | 6 | 4 |
| Musculoskeletal system | | |
| Back pain | 6 | 8 |
| Arthralgia | 5 | 9 |
| Urogenital system | | |
| Urinary tract infection | 5 | 9 |
| Digestive system | | |
| Constipation | 5 | 5 |

There was no evidence of any clinically significant changes in liver function. Few elevations of the liver enzymes were seen, and these changes were generally mild and transient. Safety data from all clinical trials with degarelix in the treatment of prostate cancer, including patients receiving other dosing regimens, were pooled. The following adverse reactions, not already listed, were reported to be drug-related by the investigator in ≥1% of patients: erectile dysfunction, gynaecomastia, hyperhidrosis, testicular atrophy, and diarrhea.

Decreased bone density has been reported in the medical literature in men who have had orchiectomy or who have been treated with a GnRH agonist. It can be anticipated that long periods of medical castration in men will have effects on bone density.

Advantages of the degarelix therapeutic dosing regimen for the treatment of prostate cancer include a diminished likelihood of occurrence and/or diminished severity of symptoms of adverse reactions, adverse events or side effects to other organs or tissues. An extensive panel of potential adverse events related to drug therapies has been described.

An adverse reaction dictionary allows investigators to identify the same adverse reaction with the same term and to identify different adverse reactions with different terms. A standard dictionary may be used, however specialized pharmaceutical dictionaries have been develop to define adverse reaction terms and their synonyms (see Gillum (1989) "The Merck regulatory dictionary: A pragmatically developed drug effects vocabulary" Drug Info. J. 23:217-220). The World Health Organization (WHO) Adverse Reaction Terminology is also available for delimiting the meanings of drug-induced side effects (see, e.g., Saltzman (1985) "Adverse reaction terminology standardization" Drug Info. J. 19:35-41). The Coding Symbols for a Thesaurus of Adverse Reaction Terms (COSTART) system is also known in the art (see, e.g., NcNeil et al. (1982) N. Engl. J. Med. 306:1259-62; and Teal and Dimmig (1985) "Adverse drug experience management" Drug Info. J. 19:17-25). These lists are often divided by body system and certain terms are annotated with alternative classifications.

COSTART provides a basis for vocabulary control of adverse reaction reports that emanate from a variety of sources. COSTART is organized primarily by anatomy. It has a hierarchical arrangement of terms, from the broadest (body-system categories) to the narrowest (specific preferred terms or even special search categories). The COSTART dictionary is used and maintained by the Center for Drugs and Biologics at the Food and Drug Administration (FDA) for marketed medicine surveillance and has been endorsed by many senior managers in the various reviewing sections. There are four indexes in COSTART: index A, comprising three lists including a body-system search categories, and a special search categories (e.g., neoplasia).

The WHO terminology system of adverse reactions is relatively short. A code number is assigned to each of these terms. This provides the advantage that the same code is retained when the term is translated into different languages. The WHO system uses a hierarchy of "preferred terms" to describe adverse reactions. Other commonly used terms are called "included terms," which are listed with their preferred terms.

The FDA and many pharmaceutical companies have gone through an evolution of systems in how they obtain, collect, process, and define adverse reactions. The medicine dictionary that has been used by the FDA ("The Center for Drugs and Biologics Ingredient Dictionary") is known in the art and its use in adverse event categorization has been addressed (see, e.g., Forbes et al. (1986) Drug Info. J. 20:135-45; and Turner et al. (1986) Drug Info. J. 20:147-50).

Certain advantages and disadvantages of COSTART, SNOMED and WHO Adverse Reaction Terminology are reviewed by Stephens ("The Detection of New Adverse Drug Reactions" pp. 18-124, Stockton Press, New York).

The MedDRA Medical dictionary for regulatory activities is a particularly useful source for definitions of adverse events relating to drug trials. MedDRA utilizes pragmatic, medically valid terminology with an emphasis on ease of use for data entry, retrieval, analysis, and display, as well as a suitable balance between sensitivity and specificity within the regulatory environment. It was developed by the International Conference on Harmonisation (ICH) and is owned by the International Federation of Pharmaceutical Manufacturers and Associations (IFPMA) acting as trustee for the ICH steering committee, and is readily available commercially (see, e.g., the MedDRA website at www.meddramsso.com). The MedDRA Maintenance and Support Services Organization (MSSO) holds a contract with the International Federation of Pharmaceutical Manufacturers Associations (IFPMA) to maintain and support the implementation of the terminology. MedDRA terminology applies to all phases of drug development, excluding animal toxicology, and has been utilized in the examples that follow.

As described in further detail below, a number of other adverse reactions including cardiovascular anomalies (e.g., cardiac arrhythmias, coronary artery disorders and cardiac disorders), arthralgia, and urinary tract infection unexpectedly occur at a lower frequency than prior art androgen depletion therapies such as the GnRH antagonist leuprolide.

Cardiovascular Disease

The invention includes methods for treating individuals with prostate cancer who are at risk for developing a cardiovascular disease, as well as methods of treating otherwise normal prostate cancer patients with a decreased likelihood of developing a cardiovascular side effect. This aspect of the invention is particularly significant, in light of recent findings suggesting the possibility of an increased risk of death from nonprostate cancer causes, particularly relating to adverse effects on cardiovascular health, in patients being treated with prior art androgen deprivation therapies (see Yannucci et al. (2006) *J. Urol.* 176:520-5).

The indicia of risk for developing cardiovascular disease have been investigated extensively and are known in the art (see, e.g., Wilson et al. (1998) *Circulation* 97:1837-47; Hackam (2003) *JAMA* 290:932-940). These cardiovascular risk factors include: high blood pressure (particularly greater than or equal to 130 over 85 mm Hg); high levels of low-density lipoprotein cholesterol (particularly greater than or equal to 160 mg/dL); low levels of high-density lipoprotein cholesterol (particularly less than 35 mg/dL); high levels of serum glucose (particularly levels of fasting glucose levels greater than about 120 mg/dL); high serum levels of C-reactive protein (CRP) (particularly levels greater than 3 mg/dL); high serum levels of homocysteine (particularly levels greater than 30 μmol/L); high serum levels of serum fibrinogen (particularly levels greater than 7.0 g/L); and high serum levels of lipoprotein(a) (Lp(a)) (particularly levels of greater than 30 mg/dL). In addition, habitual smoking has been shown to be associated with an increased risk for cardiovascular disease.

Furthermore, the association of overall body weight, body mass index (BMI) and the presence of indicators of "metabolic syndrome" with risk for cardiovascular disease have been reported (see e.g., Behn and Ur (2006) *Curr. Opin. Cardiol.* 21:353-60; and Romero-Corral et al. (2006) *The Lancet* 368:666-78).

The present disclosure further provides for methods for treating prostate cancer in a subject with a history of at least one cardiovascular event, wherein administration of degarelix to the subject decreases the likelihood of developing or experiences an additional cardiovascular event compared to treatment with a gonadotrophin releasing hormone (GnRH) agonist.

This present disclosure is further illustrated by the examples that follow, which should not be construed as limiting.

EXAMPLES

Example 1: Clinical Study of Degarelix for the Treatment of Prostate Cancer

In this example, an open-label, multi-center, randomized, parallel-group study was conducted to investigate the efficacy and safety of degarelix one month dosing regimens. Patients in two degarelix treatment groups received a degarelix starting dose of 240 mg at a concentration of 40 mg/mL followed by either of two different once-a-month dosing regimens, 160 mg (40 mg/mL) and 80 mg (20 mg/mL). These degarelix dosing regimens were compared to LUPRON DEPOT™ at 7.5 mg in patients with prostate cancer requiring androgen ablation therapy.

The study also investigated whether degarelix is safe and effective with respect to achieving and maintaining testosterone suppression to castrate levels, evaluated as the proportion of patients with testosterone suppression 0.5 ng/mL during 12 months of treatment, and compared serum levels of testosterone and prostate-specific antigen (PSA) using a degarelix dosing regimen versus leuprolide 7.5 mg during the first 28 days of treatment. The study further compared the safety and tolerability using a degarelix dosing regimen compared to treatment with leuprolide 7.5 mg, and, further, compared testosterone, luteinizing hormone (LH), follicle-stimulating hormone (FSH), and PSA response with a degarelix dosing regimen compared to leuprolide 7.5 mg. The study further compared patient reported outcomes (quality of life factors and hot flushes) using a degarelix dosing regimen as compared to leuprolide 7.5 mg during treatment. Finally, the study evaluated the pharmacokinetics of the degarelix dosing regimens investigated.

Study Design

A total of 620 patients were randomized 1:1:1 to one of three treatment groups. Of these, 610 patients were administered Investigational Medicinal Product (IMP). Ten randomized patients withdrew from the study before dosing.

Patients in two treatment groups received a degarelix starting dose of 240 mg at a concentration of 40 mg/mL (240@40) on Day 0 administered as two equivalent subcutaneous (s.c.) injections of 120 mg each. Thereafter, patients received 12 additional single s.c. degarelix doses of either 80 mg at a concentration of 20 mg/mL (80@20: degarelix 240/80 mg group) or 160 mg at a concentration of 40 mg/mL (160@40: degarelix 240/160 mg group) administered s.c. every 28 days. In the third treatment group, patients received active treatment with leuprolide 7.5 mg on Day 0 and every 28 days administered as a single intramuscular (i.m.) injection. For patients receiving treatment with leuprolide 7.5 mg, bicalutamide could be given as clinical flare protection at the Investigator's discretion.

Patients were stratified according to geographic region (Central and Eastern Europe, Western Europe and The Americas) and body weight (<90 kg and ≥90 kg).

Deqarelix 240/160 mg Group

This group received an initial dose of 240 mg at a concentration of 40 mg/mL (240@40) on Day 0. This starting dose was administered as two equivalent subcutaneous (s.c.) injections of 120 mg each. The group then received 12 maintenance doses of 160 mg at a concentration of 40 mg/mL (160@40) as single s.c doses of degarelix every 28 days.

Degarelix 240/80 mg Group

This group also received an initial dose of 240 mg at a concentration of 40 mg/mL (240@40) on Day 0. This starting dose was administered as two equivalent s.c. injections of 120 mg each. The group then received 12 maintenance doses of 80 mg at a concentration of 20 mg/mL (80@20) as single s.c doses of degarelix every 28 days.

Leuprolide 7.5 mg Group

This group received the reference therapy leuprolide 7.5 mg. This treatment was administered as a single intramuscular (i.m.) injection, once every 28 days starting at Day 0.

TABLE 3

Treatment Methodology

| Treatment Group | Starting Dose | Maintenance Doses |
|---|---|---|
| Degarelix 240/160 mg | 240@40 (as 2 doses on Day 0) | 160@40 (as 12 single doses, one every 28 days) |
| Degarelix 240/80 mg | 240@40 (as 2 doses on Day 0) | 80@20 (as 12 single doses, one every 28 days) |
| Leuprolide 7.5 mg | 7.5 mg administered at Day 0 and every 28 days via single intramuscular injection. Bicalutamide was given at the Investigator's discretion. | |

Patients were monitored on an ongoing basis and visited the clinic at monthly intervals up to one year. Patients were observed clinically for at least 1 hour after each administration of study drug. Patients who completed the study and met appropriate criteria were offered the opportunity to receive long-term treatment and support in an extension study.

A total of 807 patients were screened and 620 patients were randomized 1:1:1 into three treatment groups, degarelix 240/160 mg, degarelix 240/80 mg and leuprolide 7.5 mg. Of the 620 patients randomized, 610 patients actually received study medication including 202, 207 and 201 patients in the degarelix 240/160 mg, degarelix 240/80 mg and leuprolide 7.5 mg treatment groups, respectively. A total of 504 patients completed the study.

Diagnosis and Criteria for Study Inclusion

Males aged 18 years and over with histologically confirmed (Gleason graded) adenocarcinoma of the prostate (all stages), in whom androgen ablation treatment was indicated (except for neoadjuvant hormonal therapy) were eligible to participate. Signed informed consent was obtained before any study-related activity occurred. Patients were to have a baseline testosterone level >1.5 ng/mL and a PSA level of ≥2 ng/mL at the time of screening. Patients with rising PSA after having undergone prostatectomy or radiotherapy with curative intent could be included in the study. Patients were required to have an ECOG score of ≤2 and a life expectancy of at least 12 months. Previous or present hormonal management of prostate cancer (surgical castration or other hormonal manipulation, e.g. GnRH agonists, GnRH antagonists, antiandrogens, or estrogens) resulted in exclusion from the study. However, in patients having undergone prostatectomy or radiotherapy with curative intention, neoadjuvant hormonal treatment was accepted for a maximum duration of 6 months provided that this treatment had been terminated for at least 6 months prior to the screening visit. Concurrent treatment with a 5-α-reductase inhibitor also resulted in exclusion from the study. Patients who were candidates for a curative therapy (i.e. radical prostatectomy or radiotherapy) were excluded. Patients with histories of severe hypersensitivity reactions or clinically significant disorders (other than prostate cancer) that might affect the conclusion of the study as judged by the Investigator were not eligible to enter into the study. Patients with a marked baseline prolongation of QT/QTcF interval (>450 msec), had used concomitant medications that may prolong QT/QTcF interval or who had a history of additional risk factors for Torsade de Pointes ventricular arrhythmias were excluded. Patients who had elevated serum ALT or total bilirubin levels above upper level of normal range at the screening visit or who had known or suspected hepatic, symptomatic biliary disease were also excluded. Patients were also excluded if they had a known hypersensitivity to any component of the investigational products. In addition, patients with any form of cancer within the last five years, with the exception of prostate cancer and surgically removed basal or squamous cell carcinoma of the skin, were excluded from the study. Patients who had a mental incapacity or language barriers precluding adequate understanding or co-operation were also ineligible to participate in the study. No other investigational drug was to be administered within 28 days preceding the screening visit.

Duration of Treatment

Patients in the degarelix treatment groups received a starting dose of 240@40 on Day 0 and 12 maintenance doses of 160@40 (degarelix 240/160 mg group) or 80@20 (degarelix 240/80 mg group) every 28 days. Administration of investigational medicinal products took place on Day 0, Day 28 (±2 days) and every 28 day (±7 days) thereafter until the end of study visit; day 364 (±7 days). Patients who completed the study and met appropriate criteria were offered the opportunity to receive long-term treatment and support in an extension study.

Patients in the reference therapy group received treatment with leuprolide 7.5 mg on Day 0 and every 28 days thereafter for 12 maintenance doses. Patients who completed the study received thirteen doses in total. Patients who completed the study and met appropriate criteria were offered a switch to degarelix treatment in a continuing study. These patients were randomized to degarelix treatment 240/80 mg or 240/160 mg. On Day 0 of the study, patients previously treated with leuprolide 7.5 mg in study CS21 received a 240 mg (40 mg/mL) degarelix starting dose followed by monthly maintenance doses of either 80 mg (20 mg/mL) or 160 mg (40 mg/mL).

Patients in the comparator group were treated with leuprolide 7.5 mg pre-filled, dual-chamber syringe for intramuscular (i.m.) injection. Patients received leuprolide 7.5 mg on Day 0 and every 28 days subsequently, administered as a single i.m. injection. At the investigator's discretion, bicalutamide could be given as clinical flare protection.

Criteria for Evaluation of Efficacy

The primary efficacy endpoint was the probability of testosterone levels remaining ≤0.5 ng/mL from day 28 through day 364.

The secondary efficacy endpoints were: the proportion of patients with testosterone surge during the first 2 weeks of treatment; the proportion of patients with testosterone level ≤0.5 ng/mL at day 3; the percentage change in PSA from baseline to day 28; the probability of testosterone ≤0.5 ng/mL from day 56 through day 364; the levels of serum testosterone, LH, FSH and PSA over time through the study; the time to PSA failure, defined as two consecutive increases of 50%, and at least 5 ng/mL as compared to nadir; degarelix concentration over the first month and trough levels at day 308 and 336; the frequency and size of testosterone increases at day 255 and/or 259 compared to the testosterone level at day 252; the quality of life on days 0, 28, 84, 168 and end of study visit; the frequency and intensity of hot flushes experienced (scored daily from study start until end of study visit. In addition, two further secondary endpoints were added: the probability of sufficient testosterone response from day 28 through day 364 (a patient was considered to have insufficient testosterone response if he had one testosterone value >1.0 ng/mL or two consecutive testosterone values >0.5 ng/mL at day 28 onwards); and the percentage change in PSA from baseline to Day 14.

Criteria for Evaluation of Safety

The safety variables for this study were assessed on the following: the frequency and severity of adverse events (AEs); the presence of clinically significant changes in laboratory parameters (clinical chemistry, hematology and urinalysis); changes in electrocardiograms (ECGs) and vital signs; changes detected by physical examination; and body weight.

An adverse event (AE) was defined as any untoward medical occurrence in a patient or clinical investigation subject administered an investigational medical product (IMP) and which did not necessarily have a causal relationship with the study treatment. An AE was therefore any unfavorable or unintended sign (including an abnormal laboratory finding), symptom or disease temporally associated with the use of the product, whether or not related to the IMP.

This definition also included accidental injuries and reasons for changes in medication (drug and/or dose), any medical, nursing or pharmacy consultation, or admission to hospital or surgical operations. It also included AEs commonly observed and AEs anticipated based on the pharmacological effect of the IMP. Any clinically significant injection site reaction of a severity requiring active management (i.e. change in dose, discontinuation of study drug, more frequent follow-up or treatment of the injection site) was also considered to be an AE and was to be reported on the AE log. This definition was the minimum requirement for reporting of an AE related to injection site reactions. There may have been situations where there was no active follow-up but the reaction was still considered to be an AE.

An adverse drug reaction (ADR) was defined as an AE evaluated by the investigator as being probably or possibly related to treatment with the IMP.

An unexpected AE was defined as an AE not identified in nature, severity, or frequency in the section "undesirable effects" in the sponsor's current investigator's summary or in the leuprolide 7.5 mg package insert.

AEs could be volunteered spontaneously by the patient, or in response to general questioning about their well-being by the investigator, or as a result of changes in systemic and local tolerability, laboratory parameters or physical examinations. All AEs were recorded. The nature of each event, time and date of onset, duration, intensity, seriousness criteria, an assessment of its cause and relationship to the study medication, the need for specific therapy and its outcome were described. The action taken because of an AE was classified according to medicinal product (no change, discontinued, other change [specified]). All medications used to treat the AE were recorded in the concomitant medication log.

All patients experiencing AEs, whether considered associated with the use of the study medication or not, were to be followed until the AE resolved, stabilized or the patient's participation in the study ended (i.e. until end of study visit was completed for that patient).

Any AE assessed by the investigator as serious, severe and/or possibly or probably related to the investigational product was to be followed until it had resolved or until the medical condition of the patient was stable and all relevant follow-up information had been reported to Ferring Pharmaceuticals NS. In addition, any AE related to liver function test (LFT) was to be followed by the investigator. The outcome of an AE was classified as recovered, recovered with sequelae, not yet recovered or death.

All AEs, however minor, were documented whether or not the investigator considered the event to be related to IMP. If an AE worsened in intensity and the patient did not recover between observations, a single AE with the highest intensity was recorded. The AE reporting period was from the time the patient signed the informed consent until the end of study visit. AEs requiring therapy were treated with recognized standards of medical care to protect the health and well being of the patient. Appropriate resuscitation equipment and medicines were available to ensure the best possible treatment of an emergency situation.

AEs were graded according to the National Cancer Institute (NCI) Common Terminology Criteria for Adverse Events (CTCAE). In accordance with the CTCAE criteria, AEs were rated on a five-point scale corresponding to mild, moderate, severe, life-threatening or disabling and death. For those AEs not described in the CTCAE, a separate five-point rating scale was used for rating of the intensity of AEs as follows below:

Grade 1 AEs: Mild—Minor; no specific medical intervention; asymptomatic laboratory findings only, radiographic findings only; marginal clinical relevance.

Grade 2 AEs: Moderate—minimal intervention to local intervention, or non-invasive intervention.

Grade 3: Severe—significant symptoms, requiring hospitalization or invasive intervention; transfusion; elective interventional radiological procedure; therapeutic endoscopy or operation.

Grade 4: Life-threatening or disabling—complicated by acute, life-threatening metabolic or cardiovascular complications such as circulatory failure, haemorrhage, sepsis; life-threatening physiologic consequences; need for intensive care or emergent invasive procedure; emergent interventional radiological procedure, therapeutic endoscopy or operation.

Grade 5: Death.

Furthermore, a four-point scale was used for rating the causal relationship of the AE to the investigational product as follows.

Probable—clear-cut temporal association with improvement on cessation of test drug or reduction in dose; reappears upon re-challenge; follows a known pattern of response to test drug.

Possible—follows a reasonable temporal sequence from administration; may have been produced by the patient's clinical state or by environmental factors or other therapies administered.

Unlikely—does not follow a reasonable temporal sequence from administration. May have been produced by the subject's clinical state or by environmental factors or other therapies administered.

Unrelated—clearly and incontrovertibly due to extraneous causes, and does not meet criteria listed under unlikely, possible or probable.

Serious adverse events (SAEs) were defined as any untoward medical occurrence that at any dose resulted in death, was life-threatening, required in-patient hospitalization or prolongation of existing hospitalization, resulted in persistent or significant disability/incapacity, was an important medical event or resulted in a congenital anomaly/birth defect.

The death of a patient enrolled in this study was not considered an event per se, but rather an outcome. Any event resulting in a fatal outcome was fully documented and reported, including death, which occurred within the four weeks after treatment end, and regardless of the causality relationship to the IMP.

The term 'life-threatening' in the definition of SAEs referred to an event in which the patient was at immediate risk of death at the time of the event. It did not refer to an event, which might have caused death, if it had been more severe.

Laboratory parameters (Table 4) were recorded at screening and during the study. Details of methodology and equipment used, and the normal ranges for the various parameters are known in the art.

TABLE 4

| Laboratory Parameters | | |
|---|---|---|
| Haematology | Clinical chemistry | Urinalysis |
| Haematocrit | Albumin | Haemoglobin |
| Haemoglobin | Alkaline | Glucose |
| Mean cell | phosphatase | Ketones |
| haemoglobin | Alanine | White blood |
| concentration | aminotransferase | cells |

TABLE 4-continued

Laboratory Parameters

| Haematology | Clinical chemistry | Urinalysis |
|---|---|---|
| (MCHC) Mean cell volume (MCV) Platelet count Reticulocytes Red blood cell count (RBC) White blood cell count (WBC) with differential count (basophils, eosinophils, lymphocytes, monocytes, neutrophils | (ALT) Aspartate aminotransferase (AST) Bicarbonate Calcium Cholesterol Creatinine Gamma-glutamyltransferase (Gamma-GT) Potassium Sodium Total bilirubin Urea/Blood urea nitrogen (BUN) Uric Acid | Leucocytes pH Protein Casts, granular Casts, hyaline Casts, red blood cells Casts, waxy White blood cell casts Bacteria Cholesterol Cystine crystals Leucine crystals Tyrosine crystals |

In addition, blood samples taken pre-dose at day 0, day 168 and at the end of study visit were assessed for the presence of anti-degarelix antibodies.

Clinically significant laboratory abnormalities suggesting a disease or organ toxicity and of a severity requiring active management (i.e. change of dose, discontinuation of drug, more frequent follow-up or a diagnostic investigation) were to be reported as AEs.

Blood pressures and pulse were measured at Screening, before dosing at each dosing visit, and at the end of study visit. Diastolic and systolic blood pressure and pulse were measured after resting for five minutes in a sitting position. Patients were observed clinically for at least 1 hour after each administration of investigational medical product (IMP) to observe for any immediate onset hypersensitivity reaction. During the observation period, diastolic and systolic blood pressure and pulse were measured at 5, 10, 30 and 60 minutes after dosing.

A 12-lead electrocardiogram (ECG) was performed by site personnel at screening, day 0, day 3, every 12 weeks (84 days) after day 0 and at the end of study visit. ECGs were performed before dosing, if a dosing visit was scheduled. The ECGs were acquired digitally and the measurements were performed as known in the art. The ECG measurements included heart beat, PR, QRS intervals, QT and QTc, T and U wave.

Each patient also underwent a physical examination at screening, day 0, every 12 weeks thereafter and at the end of study visit. Any clinically significant abnormal findings observed at screening were recorded. Any clinically significant abnormal findings observed thereafter were recorded as AEs.

Body weight was measured at screening and the end of study visit. Height (without shoes) was measured at screening. Body mass index (BMI) is defined as the individual's body weight divided by the square of their height. The formulas universally used in medicine produce a unit of measure of kg/m2. Body mass index may be accurately calculated using any of the formulas below.

Statistical Methods

All statistical analyses were performed, and summary statistics calculated, using statistical analysis software SAS™ version 9 or higher. The populations for analysis were:

The intention-to-treat (ITT) analysis set included all randomized patients who received at least one dose of investigational medicinal product (IMP).

The per protocol (PP analysis set) comprised all the ITT analysis set without any major protocol violations The safety population was identical to the ITT analysis set, and therefore all safety analyses were performed on the ITT analysis set.

The primary efficacy endpoint was analyzed for both the ITT and PP analysis sets, with the ITT analysis set considered primary. The primary efficacy endpoint was analyzed using the Kaplan Meier method. For each of the three treatment groups, testosterone response rates with 95% confidence interval (CI) were calculated by log-log transformation of survivor function. Differences between the degarelix treatment groups and leuprolide 7.5 mg were assessed using a 97.5% CI calculated by normal approximation using pooled standard error.

To assess the efficacy of degarelix, two hypotheses were tested:

(1) The FDA criterion was to determine whether the lower bound of the 95% confidence interval (CI) for the cumulative probability of testosterone ≤0.5 ng/mL from Day 28 to Day 364 was no lower than 90%.

(2) The EMEA criterion was to determine whether degarelix was non-inferior to leuprolide 7.5 mg with respect to the cumulative probability of testosterone ≤0.5 ng/mL from Day 28 to Day 364. The non-inferiority limit for the difference between treatments (degarelix versus leuprolide 7.5 mg) was −10 percentage points.

All secondary efficacy endpoints were analyzed for both the ITT and PP analysis sets, unless otherwise stated. The proportion of patients with testosterone surge during the first 2 weeks of treatment was analyzed using Fisher's exact test. Fisher's exact test was also used to analyze the proportion of patients with testosterone level ≤0.5 ng/mL at day 3. The percentage change in PSA from baseline to day 28 endpoint was analyzed by a Wilcoxon test. For both Fisher's exact test and the Wilcoxon test, separate data presentations were made by treatment group, geographic region, weight strata (<90 kg, ≥90 kg) and for the leuprolide 7.5 mg subgroup.

The secondary endpoints; probability of testosterone ≤0.5 ng/mL from Day 56 through Day 364, time to PSA failure and probability of sufficient testosterone response from Day 28 through Day 364 were analyzed by the Kaplan-Meier method.

Efficacy Results

The primary objective of this study was to demonstrate the effectiveness of degarelix in achieving and maintaining testosterone suppression to castrate levels, evaluated as the proportion of patients with testosterone suppression ≤0.5 ng/mL during 12 months of treatment.

Figure 2:
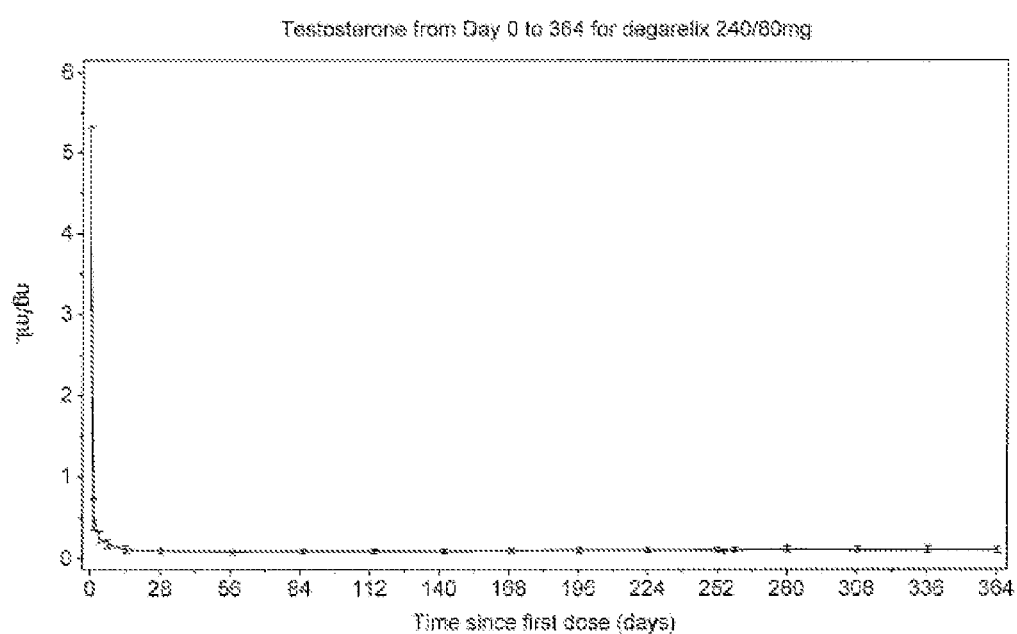
FIG. 2 is a graphical representation of the effect of degarelix 240 mg/80 mg dosing on plasma testosterone from day 0 to day 364 of treatment.

The results show that degarelix delivered at the 240/80 mg dosing regimen produced a rapid and effective suppression in testosterone levels, which remained low throughout the 364 day period of treatment (FIG. 2).

Kaplan-Meier estimates of the probabilities of testosterone ≤0.5 ng/mL from day 28 to day 364 were 98.3%, 97.2% and 96.4% for the degarelix 240/160 mg, degarelix 240/80 mg and leuprolide 7.5 mg groups, respectively. For all three treatment groups the lower bound of the 95% CI was above the pre-specified 90% threshold. Treatment with degarelix was demonstrated to be non-inferior to leuprolide 7.5 mg therapy with respect to the probability of testosterone ≤0.5 ng/mL from day 28 to day 364. For both degarelix treatment groups, the entire 97.5% CI for the difference in probability compared with the leuprolide 7.5 mg group was greater than the non-inferiority limit of −10 percentage points. Thus the study fulfilled the FDA and EMEA criteria for efficacy.

The robustness of the results for the primary efficacy endpoint was supported by an observed cases analysis, which produced similar estimates of the overall proportion of patients with testosterone ≤0.5 ng/mL from day 28 to day 364 for the degarelix 240/160 mg, degarelix 240/80 mg and leuprolide 7.5 mg groups of 98.2%, 97.0% and 96.0%, respectively. The findings of the primary analysis were further supported by a secondary efficacy analysis of the probability of testosterone ≤0.5 ng/mL from day 56 to day 364.

Figure 3:
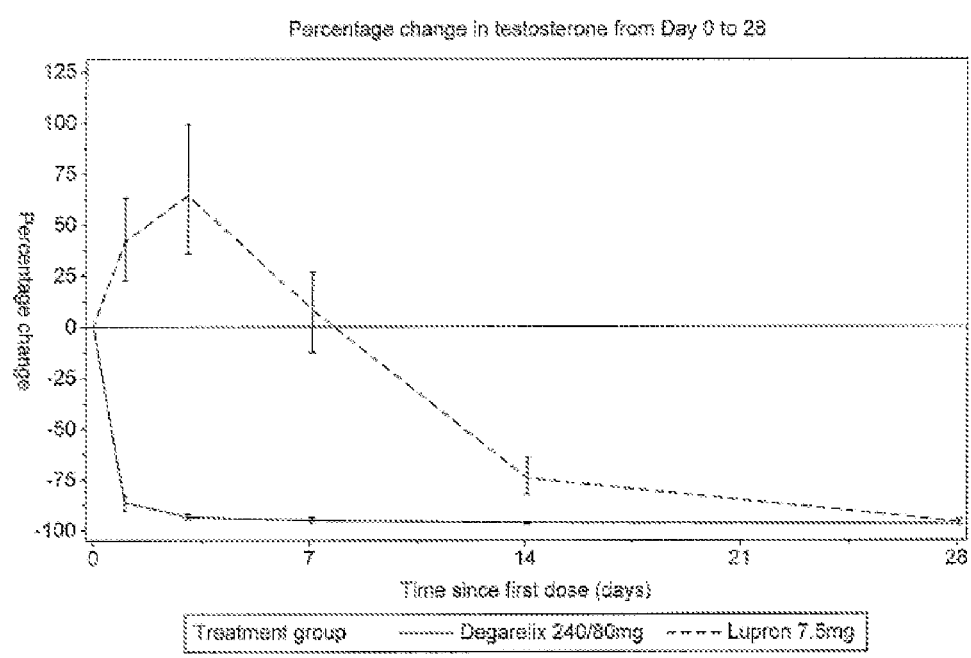
FIG. 3 is a graphical representation comparing the effect of degarelix 240 mg/80 mg dosing with the effect of Lupron 7.5 mg dosing on the percentage change in plasma testosterone from day 0 to day 28 of treatment.

As expected, a significantly higher proportion of patients in the leuprolide 7.5 mg group (80.1%) had a testosterone surge (increase ≥15% from baseline) during the first two weeks of treatment compared with the pooled degarelix groups (0.2%: one patient) (p<0.0001, Fisher's exact test). The patient treated with degarelix can be considered to be an artifact as this patient had low testosterone at baseline (0.0065 ng/mL) thus a surge from such a low baseline value was not remarkable. Conversely, 96% of patients receiving degarelix exhibited testosterone suppression on day 3 compared with no patients in the leuprolide 7.5 mg group (p<0.0001, Fisher's exact test). As shown in FIG. 3, the degarelix 240/80 mg dosing regimen rapidly and efficiently suppressed testosterone levels, while Lupron 7.5 mg acted much more gradually and only after an initial testosterone surge.

Figure 4:
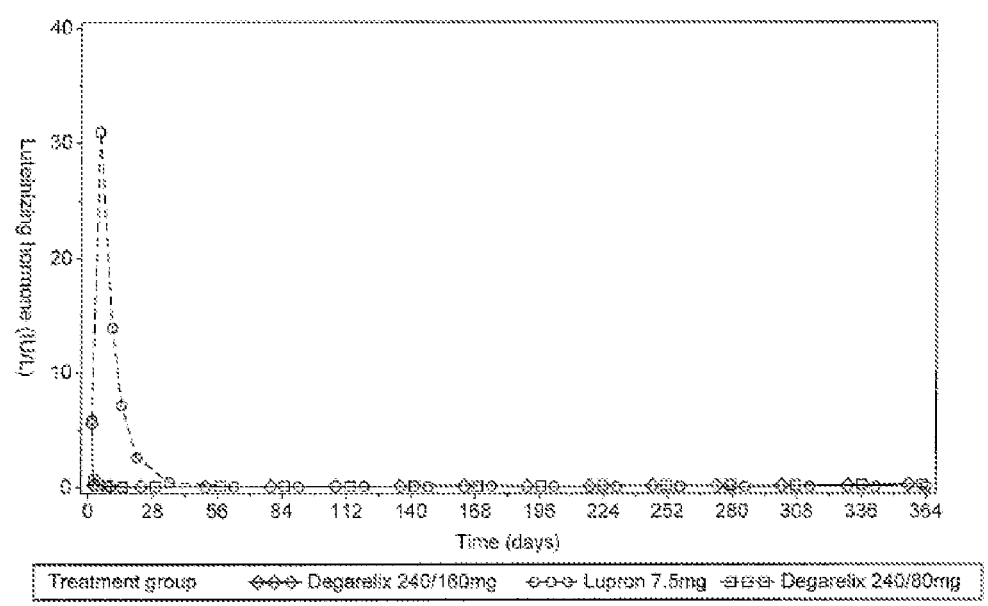
FIG. 4 is a graphical representation comparing the effect of degarelix 240 mg/160 mg and degarelix 240 mg/80 mg dosing with the effect of Lupron 7.5 mg dosing on the median levels of luteinizing hormone (LH) over time from day 0 to day 364 of treatment.

The profiles for serum levels of LH over time were similar to those observed for testosterone. Following administration of degarelix, median LH levels for the ITT analysis set decreased rapidly and were <0.7 IU/L on day 1, a decrease of approximately 88% from baseline. For both degarelix treatment groups median LH levels remained suppressed until the end of the study on day 364. In contrast, a surge in median LH levels was observed for patients in the leuprolide 7.5 mg group, which peaked at 31.0 IU/L on day 1 (>400% increase from baseline) before decreasing exponentially to 0.035 IU/L by day 56 and remaining at this level until day 364 (see FIG. 4).

Figure 5:
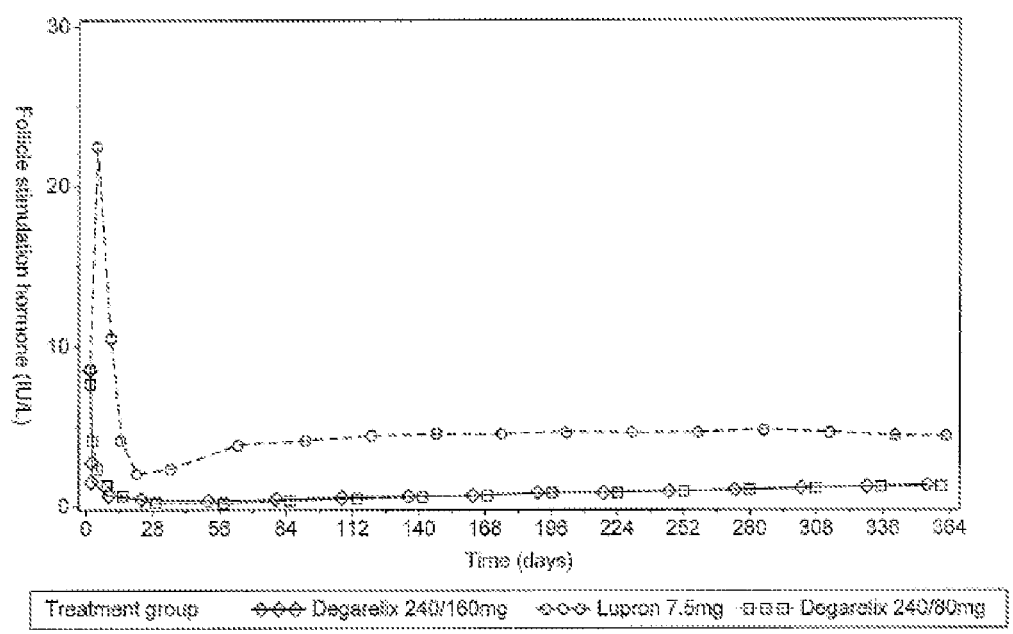
FIG. 5 is a graphical representation comparing the effect of degarelix 240 mg/160 mg and degarelix 240 mg/80 mg dosing with the effect of Lupron 7.5 mg dosing on the median levels of follicle stimulating hormone (FSH) over time from day 0 to day 364 of treatment.

A rapid decrease in FSH levels was also observed in patients treated with degarelix. Administration of degarelix resulted in a reduction in median FSH levels to ≤1.5 IU/L by day 7, a >80% decrease from baseline. For both degarelix treatment groups median FSH levels remained suppressed until the end of the study on day 364. For patients in the leuprolide 7.5 mg group there was an initial surge in FSH levels similar to that observed for LH levels which peaked at 22.5 IU/L on day 1 (146% increase from baseline) before decreasing exponentially to 2.0 IU/L by day 14. Median FSH subsequently increased around day 56 to a plateau of approximately 4.40 IU/L and stayed there until day 364 (see FIG. 5).

Figure 6:
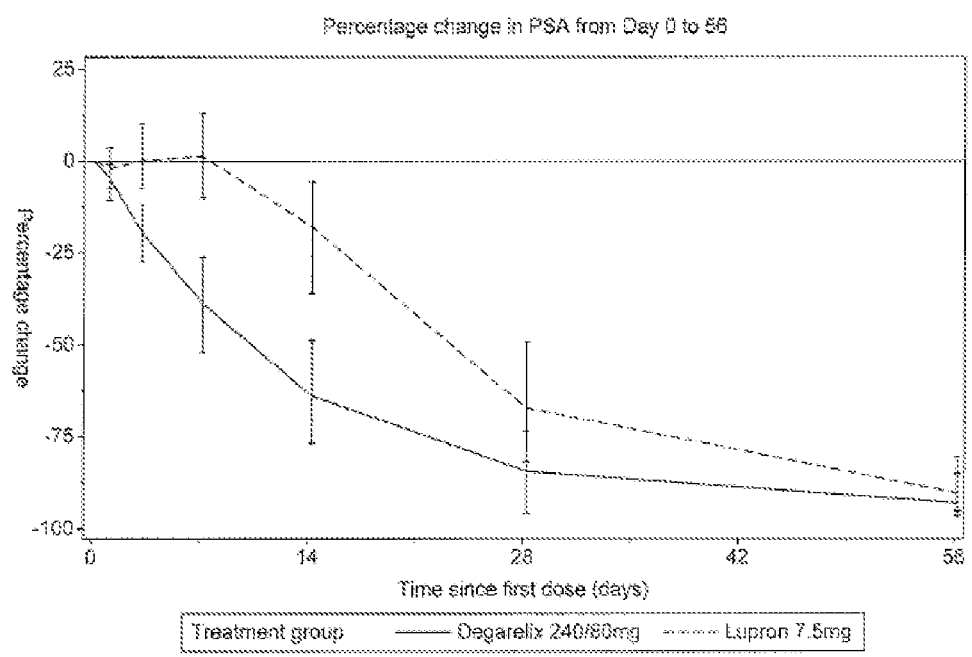
FIG. 6 is a graphical representation comparing the effect of degarelix 240 mg/80 mg dosing with the effect of Lupron 7.5 mg dosing on prostate specific antigen (PSA) levels from day 0 to day 56 of treatment.

As shown in FIG. 6, the degarelix 240/80 mg dosing regimen also produced a more rapid and efficient reduction in PSA levels than did treatment with Lupron 7.5 mg. A rapid reduction in PSA levels was observed for patients treated with degarelix. In contrast, PSA levels in the leuprolide 7.5 mg group reached a plateau during the first week of treatment before decreasing exponentially to suppressed levels. There was a significantly greater reduction in median PSA levels from baseline that was observed on day 14 and day 28 for degarelix patients compared with leuprolide 7.5 mg patients (p<0.0001, Wilcoxon test). The probability of a PSA observation from the pooled degarelix groups being less than one from the leuprolide 7.5 mg group was slightly higher on day 14 (0.82) than on day 28 (0.70). The probability of completing the study without experiencing PSA failure was highest in the degarelix 240/80 group (91.2%) and slightly lower (~85.8%) for both the degarelix 240/160 mg and leuprolide 7.5 mg groups, although this difference was not statistically significant.

Anti-androgen therapy, as per protocol, was given to 22 patients in the leuprolide 7.5 mg group at the start of treatment for flare protection. PSA data for these patients showed a greater median percentage change from baseline at day 14 (61.7% reduction) and day 28 (89.1%) compared to those patients in the leuprolide 7.5 mg group who did not receive anti-androgen therapy where the percentage reduction was 15.3% and 61.7% at days 14 and 28, respectively. It should be noted that the median percentage change in PSA levels in the leuprolide plus antiandrogen patients was similar to those patients treated with degarelix, thereby confirming that degarelix is more effective than conventional GnRH agonist therapy at suppressing PSA at the start of treatment. Degarelix does not require additional concomitant medication as prophylaxis for flare, yet a starting dose of 240 mg has a similar effect on PSA levels as the combination of GnRH agonist plus anti-androgen.

The pharmacodynamic profile for degarelix was characteristic of a GnRH antagonist with serum levels of testosterone, LH and FSH suppressed rapidly. In contrast, for patients in the leuprolide 7.5 mg group, serum levels of testosterone, LH and FSH increased rapidly within the first week of treatment before falling to suppress levels.

Safety Results

Safety and tolerability were evaluated by observed and reported treatment-emergent AEs, including injection site reactions, haematological, clinical chemistry and urinalysis laboratory parameters, vital signs/clinical observations, and body weight measurements and physical examination, ECGs and concomitant medication.

Safety parameters were evaluated for all patients included in the ITT analysis set, comprising all 610 randomized patients who received at least one dose of study medication. All safety tables include four columns: the three treatment groups described separately, and the pooled degarelix group.

Brief Summary of Adverse Events

Adverse events were regarded as 'treatment-emergent' if they occurred in the time interval from initial dosing to end-of-study. Adverse events were considered 'pre-treatment' if they occurred between screening and the initial injections of IMP. As described above, all AEs were classified according to MedDRA (version 10.0) system organ class (SOC), sorted alphabetically, and by preferred term (PT), in decreasing frequency of occurrence. Treatment-emergent AEs were expressed in terms of intensity (using NCI CTCAE) and relationship to study drug. An overall summary of treatment-emergent AEs is presented in Table 5.

TABLE 5

Overall Summary of Treatment-Emergent Adverse Events
Treatment Group

| Adverse events category | Degarelix 240/160 mg N (%) E | 240/80 mg N (%) E | Total N (%) E | Leuprolide 7.5 mg N (%) E |
|---|---|---|---|---|
| ITT analysis set | 202 (100%) | 207 (100%) | 409 (100%) | 201 (100%) |
| All AEs | 167 (83%) 941 | 163 (79%) 937 | 330 (81%) 1878 | 156 (78%) 777 |
| Deaths (Grade 5) | 5 ( 2%) 6 | 5 ( 2%) 5 | 10 ( 2%) 11 | 9 ( 4%) 10 |
| Serious AEs | 24 (12%) 41 | 21 (10%) 26 | 45 (11%) 67 | 28 (14%) 54 |
| AEs leading to discontinuation | 19 ( 9%) 19 | 15 ( 7%) 15 | 34 ( 8%) 34 | 12 ( 6%) 12 |
| ADRs | 120 (59%) 463 | 118 (57%) 459 | 238 (58%) 922 | 84 (42%) 146 |

N = number of patients with adverse events
% = percentage of patients with adverse events
E = number of adverse events
ADR = AE assessed by investigator as possibly/probably related to investigational product
Common Toxicity Criteria for Adverse Events used for intensity grading The overall percentages of patients experiencing treatment-emergent AEs were comparable across all three treatment groups. 167 (83%) patients in the degarelix 240/160 mg group reported treatment-emergent AEs, compared with 163 (79%) patients in the degarelix 240/80 mg group, and 156 (78%) patients in the leuprolide 7.5 mg group. In total, there were reports of ADRs in 238 (58%) pooled degarelix patients, with 120 (59%) patients in the degarelix 240/160 mg group, 118 (57%) patients in the degarelix 240/80 mg group. For the leuprolide 7.5 mg group, 42% patients reported ADRs. This difference was expected and could be accounted for entirely by injection-related AEs, which exhibited higher rates in the degarelix pooled arms. Excluding injection-site ADRs, the incidences of the remaining ADRs were similar in the three treatment groups:

88 (44%) patients reported ADRs, excluding injections site reactions, in the degarelix 240/160 mg group 90 (43%) patients reported ADRs, excluding injections site reactions, in the degarelix 240/80 mg group 84 (42%) patients reported ADRs, excluding injections site reactions, in the leuprolide 7.5 mg group.

Such results suggest that both the degarelix maintenance doses (80@20 mg/mL or 160@40 mg/mL) resulted in a similar incidence of ADRs.

A total of 45 (11%) pooled degarelix patients reported 67 serious AEs, including ten deaths. Overall, 24 (12%) patients in the degarelix 240/160 mg group reported serious AEs, compared with 21 (10%) patients in the degarelix 240/80 mg group, and 28 (14%) patients, including 9 deaths, in the leuprolide 7.5 mg group. All deaths were assessed to be unrelated or unlikely to be related to study treatment. Such results should also be interpreted in the knowledge that this is an elderly patient population (mean age 72 years) with both prostate cancer and other underlying health issues.

Thirty-four (8%) pooled degarelix patients were reported as being withdrawn due to AEs (including both fatal and non-fatal AEs); 19 (9%) patients in the degarelix 240/160 mg group and 15 (7%) patients in the degarelix 240/80 mg group, and there were 12 (6%) patients withdrawn in the leuprolide 7.5 mg group. Of the pooled degarelix patients, there were reports for 17 patients of SAEs that led to withdrawal.

Detailed Analysis of Adverse Events

While the overall occurrence of adverse events was similar in the two degarelix treatment groups and the leuprolide control group, a large majority of such events for the degarelix treatment groups were mere injection site reactions related to the subcutaneous/depot delivery system employed for degarelix. In comparison, leuprolide intramuscular injection was not associated with such a high rate of injection site reactions even though the overall rate of adverse occurrence was similar. Accordingly, a detailed analysis of the precise type of adverse events occurring in each study group was undertaken to characterize the types of adverse events, other than injection site reactions, that must be occurring in the leuprolide treatment group to account for the overall similar adverse event occurrence rates.

Table 6 shows a summary of the number of patients reporting treatment-emergent AEs, presented by SOC. All treatment-emergent AEs are presented by system organ class and Med-DRA preferred term.

TABLE 6

Treatment-Emergent Adverse Events by System Organ Class

| | Treatment Group | | | |
|---|---|---|---|---|
| | Degarelix | | | Leuprolide |
| MedDRA System Organ Class | 240/160 mg N (%) | 240/80 mg N (%) | Total N (%) | 7.5 mg N (%) |
| ITT analysis set | 202 (100%) | 207 (100%) | 409 (100%) | 201 (100%) |
| Treatment-emergent adverse events | 167 (83%) | 163 (79%) | 330 (81%) | 156 (78%) |
| BLOOD & LYMPHATIC SYSTEM DISORDERS | 11 ( 5%) | 5 ( 2%) | 16 ( 4%) | 12 ( 6%) |
| CARDIAC DISORDERS | 19 ( 9%) | 17 ( 8%) | 36 ( 9%) | 27 (13%) |
| CONGENITAL, FAMILIAL & GENETIC DISORDERS | | | | 1 (<1%) |
| EAR & LABYRINTH DISORDERS | 3 ( 1%) | 6 ( 3%) | 9 ( 2%) | 3 ( 1%) |
| ENDOCRINE DISORDERS | 2 (<1%) | 2 (<1%) | 3 ( 1%) | |

TABLE 6-continued

Treatment-Emergent Adverse Events by System Organ Class

|  | Treatment Group | | | |
|---|---|---|---|---|
|  | Degarelix | | | Leuprolide |
| MedDRA System Organ Class | 240/160 mg N (%) | 240/80 mg N (%) | Total N (%) | 7.5 mg N (%) |
| EYE DISORDERS | 4 (2%) | 6 (3%) | 10 (2%) | 5 (2%) |
| GASTROINTESTINAL DISORDERS | 33 (16%) | 38 (18%) | 71 (17%) | 39 (19%) |
| GENERAL DISORDERS & ADMINISTRATION SITE CONDITIONS | 102 (50%) | 92 (44%) | 194 (47%) | 36 (18%) |
| HEPATOBILIARY DISORDERS | 2 (<1%) | 2 (<1%) | 4 (<1%) | 3 (1%) |
| IMMUNE SYSTEM DISORDERS | 1 (<1%) | 1 (<1%) | 2 (<1%) |  |
| INFECTIONS & INFESTATIONS | 38 (19%) | 45 (22%) | 83 (20%) | 49 (24%) |
| INJURY, POISONING & PROCEDURAL COMPLICATIONS | 11 (5%) | 10 (5%) | 21 (5%) | 17 (8%) |
| INVESTIGATIONS | 58 (29%) | 54 (26%) | 112 (27%) | 62 (31%) |
| METABOLISM & NUTRITION DISORDERS | 26 (13%) | 14 (7%) | 40 (10%) | 15 (7%) |
| MUSCULOSKELETAL & CONNECTIVE TISSUE DISORDERS | 37 (18%) | 31 (15%) | 68 (17%) | 53 (26%) |
| NEOPLASMS BENIGN, MALIGNANT & UNSPECIFIED (INCL CYSTS AND POLYPS) | 12 (6%) | 10 (5%) | 22 (5%) | 16 (8%) |
| NERVOUS SYSTEM DISORDERS | 27 (13%) | 24 (12%) | 51 (12%) | 23 (11%) |
| PSYCHIATRIC DISORDERS | 16 (8%) | 16 (8%) | 32 (8%) | 21 (10%) |
| RENAL & URINARY DISORDERS | 26 (13%) | 28 (14%) | 54 (13%) | 39 (19%) |
| REPRODUCTIVE SYSTEM & BREAST DISORDERS | 13 (6%) | 9 (4%) | 22 (5%) | 21 (10%) |
| RESPIRATORY, THORACIC & MEDIASTINAL DISORDERS | 17 (8%) | 25 (12%) | 42 (10%) | 18 (9%) |
| SKIN & SUBCUTANEOUS TISSUE DISORDERS | 21 (10%) | 18 (9%) | 39 (10%) | 10 (5%) |
| SURGICAL & MEDICAL PROCEDURES | 2 (<1%) |  | 2 (<1%) |  |
| VASCULAR DISORDERS | 65 (32%) | 71 (34%) | 136 (33%) | 60 (30%) |

N = number of patients with adverse events
% = percentage of patients with adverse events Treatment-emergent AEs were reported for a comparable percentage of patients across all three treatment groups: 83%, 79% and 78% of patients in the degarelix 240/160 mg, degarelix 240/80 mg and leuprolide 7.5 mg groups, respectively. As shown in Table B above, there were no marked differences between the SOCs affected for the two degarelix treatment groups. The predominant system-organ class affected for degarelix patients in both treatment groups was 'General Disorders and Administration Site Conditions', reported for 47% pooled degarelix patients, and 18% leuprolide 7.5 mg patients. The majority of these AEs were injection site pain, which occurred in 29% of pooled degarelix patients. In addition, 'vascular disorders' were reported for 33% degarelix patients, and 30% leuprolide 7.5 mg patients, primarily hot flushes. Other SOCs affected in ≥15% patients were: 'investigations' in 27% degarelix patients and 31% leuprolide 7.5 mg patients, 'infections and infestations' in 20% and 24% patients, respectively, 'musculoskeletal and connective tissue disorders' in 17% and 26% patients, respectively, and 'gastrointestinal disorders' in 17% and 19% patients, respectively. The most frequent musculoskeletal and connective tissue disorders were back pain, reported by 6% of degarelix patients and 8% of leuprolide 7.5 mg patients, and arthralgia reported for 4% of degarelix patients and 9% of leuprolide 7.5 mg patients.

In examining the SOCs of AEs associated with degarelix treatment as compared to leuprolide, several areas of increased risk for leuprolide as compared to degarelix emerged. For example, 'musculoskeletal and connective tissue disorders' occurred in 26% of leuprolide patients, as compared to only 17% of degarelix patients overall (and even lower, 15% in the degarelix 240/80 mg treatment group). Furthermore, 'renal and urinary disorders' occurred in 19% of leuprolide patients, but only 13% of degarelix patients, while 'reproductive system and breast disorders' occurred in 10% of leuprolide patients, but only 5% of degarelix patients. Furthermore, 'cardiac disorders' occurred at a slightly increased overall frequency for leuprolide treatment (13%) than for degarelix (9% overall between the two treatment groups). This may be of particular interest, since, as addressed above, there is some concern in the art that certain androgen deprivation therapies adversely affect cardiovascular health (see Yannucci et al. (2006) J. Urology 176:520-525; and Etzioni et al. (1999) J. Natl. Canc. Inst. 91:1033). Accordingly, androgen deprivation therapies that minimize the risk of cardiovascular side effects are particularly desirable.

The increased risk for cardiac disorders, musculoskeletal and connective tissue disorders, renal and urinary disorders, and reproductive system disorders for leuprolide as compared to degarelix likely account for the overall similarity in adverse events between leuprolide and degarelix, despite the fact that most of the adverse events seen with degarelix were mere injection site reactions related to the mode of subcutaneous delivery and not to adverse systemic effects on other organ systems.

As shown in Table 7, the most frequently reported treatment-emergent AEs for patients treated with degarelix were injections site reactions (particularly injection site pain and erythema). The most frequently reported AE for both degarelix and leuprolide patients during the study were flushing events: overall, 52 (26%) patients in the degarelix 240/160 mg group reported hot flushes, compared to 53 (26%) patients in the degarelix 240/80 mg group, and 43 (21%) patients in the leuprolide 7.5 mg group.

TABLE 7

Adverse Events by System Organ Class and Preferred Term Occurring in ≥5% of any Treatment Group

| | Treatment Group | | | |
|---|---|---|---|---|
| | Degarelix | | | Leuprolide |
| MedDRA System Organ Class/ | 240/160 mg | 240/80 mg | Total | 7.5 mg |
| Preferred Term | N (%) | N (%) | N (%) | N (%) |
| ITT analysis set | 202 (100%) | 207 (100%) | 409 (100%) | 201 (100%) |
| Treatment-emergent adverse events | 167 (83%) | 163 (79%) | 330 (81%) | 156 (78%) |
| GASTROINTESTINAL DISORDERS | 33 (16%) | 38 (18%) | 71 (17%) | 39 (19%) |
| Nausea | 11 (5%) | 9 (4%) | 20 (5%) | 8 (4%) |
| Constipation | 6 (3%) | 11 (5%) | 17 (4%) | 10 (5%) |
| GENERAL DISORDERS AND ADMINISTRATION SITE CONDITIONS | 102 (50%) | 92 (44%) | 194 (47%) | 36 (18%) |
| Injection site pain | 61 (30%) | 58 (28%) | 119 (29%) | 1 (<1%) |
| Injection site erythema | 48 (24%) | 36 (17%) | 84 (21%) | |
| Injection site swelling | 14 (7%) | 13 (6%) | 27 (7%) | |
| Fatigue | 13 (6%) | 7 (3%) | 20 (5%) | 13 (6%) |
| Injection site induration | 11 (5%) | 8 (4%) | 19 (5%) | |
| Injection site nodule | 13 (6%) | 6 (3%) | 19 (5%) | |
| Chills | 7 (3%) | 11 (5%) | 18 (4%) | |
| INFECTIONS AND INFESTATIONS | 38 (19%) | 45 (22%) | 83 (20%) | 49 (24%) |
| Urinary tract infection | 3 (1%) | 10 (5%) | 13 (3%) | 18 (9%) |
| INVESTIGATIONS | 58 (29%) | 54 (26%) | 112 (27%) | 62 (31%) |
| Weight increased | 22 (11%) | 18 (9%) | 40 (10%) | 24 (12%) |
| Alanine aminotransferase increased | 17 (8%) | 20 (10%) | 37 (9%) | 11 (5%) |
| Aspartate aminotransferase increased | 10 (5%) | 11 (5%) | 21 (5%) | 6 (3%) |
| METABOLISM AND NUTRITION DISORDERS | 26 (13%) | 14 (7%) | 40 (10%) | 15 (7%) |
| Hypercholesterolaemia | 12 (6%) | 7 (3%) | 19 (5%) | 5 (2%) |
| MUSCULOSKELETAL AND CONNECTIVE TISSUE DISORDERS | 37 (18%) | 31 (15%) | 68 (17%) | 53 (26%) |
| Back pain | 12 (6%) | 12 (6%) | 24 (6%) | 17 (8%) |
| Arthralgia | 6 (3%) | 11 (5%) | 17 (4%) | 18 (9%) |
| VASCULAR DISORDERS | 65 (32%) | 71 (34%) | 136 (33%) | 60 (30%) |
| Hot flush | 52 (26%) | 53 (26%) | 105 (26%) | 43 (21%) |
| Hypertension | 14 (7%) | 12 (6%) | 26 (6%) | 8 (4%) |

N = number of patients with adverse events
% = percentage of patients with adverse events Long-term treatment with degarelix and leuprolide 7.5 mg was anticipated to result in adverse reactions associated with testosterone suppression such as hot flushes, loss of libido, impotence and infertility, and increased sweating. It was therefore to be expected that flushing events would be relatively common and largely considered possibly or probably related to treatment. However, very few AEs related to sexual dysfunction or sweating were reported. In total, there were reports for 22 (5%) pooled degarelix patients and 21 (10%) leuprolide patients with reproductive system/breast disorders and approximately 1% patients treated with degarelix with sweating disorders (skin and subcutaneous tissues SOC): six (1%) of patients reported erectile dysfunction, six (1%) of patients reported night sweats, four (<1%) of patients experienced testicular pain, three (<1%) of patients reported pelvic pain, three (<1%) of patients reported hyperhidrosis, two (2%) of patients each experienced gynaecomastia, prostatitis or testicular atrophy, and all other reproductive system/breast disorders were reported by one (<1%) of patients, and no other sweating disorders were reported.

An analysis of these SOC/preferred term data further support the finding discussed above for diminished musculoskeletal disorders, and renal and urinary disorders for degarelix as compared to leuprolide treatments. For example, 9% of leuprolide patients experienced urinary tract infections during the course of treatment as compared to only 3% of all degarelix-treated patients. Similarly, 9% of leuprolide patients experienced arthralgia (joint pain) during the course of treatment while only 4% of all degarelix-treated patients experienced arthralgia.

To summarize, the incidence of treatment-emergent AEs was similar for patients treated with degarelix and leuprolide 7.5 mg. Treatment-emergent AEs were reported by 330 (81%) patients in the pooled degarelix treatment groups and by 156 (78%) patients in the leuprolide 7.5 mg group. The majority of AEs were of mild or moderate intensity.

There were 58% of patients treated with degarelix with reported AEs considered to be possibly/probably related to IMP by the Investigator (ADR) and those treated with leuprolide 7.5 mg had 42% ADRs, however the majority of treatment-emergent ADRs were general disorders and administration site conditions including injection-site reactions which occurred in 173 (42%) patients in the pooled degarelix group. For patients treated with degarelix, the overall incidence of treatment-emergent injection site reactions was 4.4 per 100 injections. Most injection site reactions occurred after the first dose of degarelix where two injections were administered and injection site reactions were decreased over time. Among MedDRA preferred terms, the highest incidences were injection site pain (2.9 per 100 injections) and injection site erythema (1.9 per 100 injections) for the pooled degarelix group. All other preferred terms had an incidence rate of 0.5 per 100 injections or less. None of the injection-related ADRs were considered to be serious, and there were no immediate onset hypersensitivity reactions. Five (1.2%) patients reported degarelix-related injection site reactions, which led to withdrawal. Other commonly reported ADRs were hot flushes which were an expected adverse reaction associated with testosterone suppression. In total, hot flushes were reported by 104 (25%) patients treated with degarelix and 42 (21%) treated with leuprolide 7.5 mg. One patient treated with degarelix reported a hot flush ADR, which led to withdrawal. Notably, although AEs related to sexual dysfunction would be anticipated to result from testosterone suppression, very few were actually reported.

There were 121 serious adverse events SAEs reported by 73 (12%) patients, with relatively equal incidence across the treatment groups. The most common SAEs were cardiac disorders, which occurred in ten (2%) patients in the pooled degarelix group and ten (5%) patients in the leuprolide 7.5 mg group; and renal and urinary disorders, which occurred in 10 (2%) patients in the pooled degarelix group and six (3%) patients in the leuprolide 7.5 mg group.

Weight increase is a known effect of androgen deprivation and markedly abnormal increases in weight of ≥7% from baseline were observed in 10% patients treated with degarelix and 13% patients treated with leuprolide 7.5 mg. The incidence of other markedly abnormal changes in vital signs was consistent with a group of elderly patients many of whom had a medical history of cardiac disease or hypertension.

Therefore, while degarelix treatment resulted in a significant number of subjects experiencing minor injection site reactions, these adverse effects were remarkably less serious than many of those associated with the GnRH agonist leuprolide. Notably, these minor injection site reactions were also much less serious than the potentially life-threatening effects associated with another GnRH antagonist, Abarelix (Plenaxis in the U.S.) (see www.fda.gov/cder/drug/infopage/plenaxis). Indeed Abarelix/Plenaxis has been associated with serious allergic reactions (e.g., swelling of the tongue/throat, asthma, wheezing and serious breathing problems), and therefore is only available through a special "user safety program" to ensure that it is safely used by doctors with the right skills to administer and monitor the drug.

Further Statistical Analyses of Subgroup Populations

Further statistical analysis of the CS21 clinical study results was undertaken in order to determine whether any of the advantages in superior efficacy and/or diminished side effects of degarelix over leuprolide treatment were particularly pronounced in certain patient subgroups. Particular attention was paid to whether particular patient subgroups were responsible for any of the diminished cardiac, arthralgic and/or urinary tract infection side effects seen with degarelix treatment as compared to leuprolide treatment.

Using the results from the summary of clinical efficacy (SCE) and summary of clinical safety (SCS) findings, different patient subgroups were analyzed. Subgroup distinguishers included race (white, black, and other), age (<65 years, ≥65 years to <70 years, and >75 years), weight (<70 kg, ≥70–<90 kg, and ≥90 kg), body mass index (BMI) (≤20, >20 to 30, and >30 kg/m$^2$)), region (North-America, Western Europe, Central and Eastern Europe and Other), and stage of prostate cancer (e.g., localized, locally advanced, and metastatic).

The SCS summarizes both crude incidences (n/N) as well as incidence rates of adverse events (number of patients with at least one adverse event investigated per 1,000 person years) including exact 95% CI based on the Poisson model and presented per MedDRA Preferred term (and grouped by SOC) for all study-groups, including the CS21 trial (the trial comprising the controlled phase 3 study group) and for all sub-groups. Briefly, the Poisson model provides exact 1-α lower (LL) and upper (UL) confidence limits are LL=$\chi_{2x;\ \alpha/2}^2/(2T)$ and UL=$\chi_{2(x+1);\ 1-\alpha/2}^2/(2T)$, respectively, where T is the number of 1,000 person years and x=number of subjects at least once having reported the adverse event under investigation (see Gerlinger et al. (2003) *Eur. J. Contracept. Reprod. Health Care* 8:87-92).

For the phase 3 controlled study (CS21), crude incidences in the degarelix arms were compared to those in the leuprolide 7.5 mg arm using two-sided Fisher exact test and corresponding P-value as a flagging device. These P values were presented as *(0.01<P≤0.05),  (0.001<P≤0.01), and * (P≤0.001). Similarly, incidence rates were compared using P values associated with the Poisson model-based UMPU test. Briefly, assuming $x_i$~Poisson($\lambda_i T_i$), where xi=the number of subjects with the event, $T_i$=total number of 1,000 person years in arm i and $\lambda_i$=incidence rate in arm i (i=1,2), then the P value=2 min (P(S≥1), P(S≤$x_1$), 0.5), where S~Binomial ($x_1+x_2$, $T_1/(T_1+T_2)$) (see, e.g. Lehmann (1986) *Testing Statistical Hypotheses*, 2$^{nd}$ edition, Springer-Verlag, New York).

Based on these results all adverse events (on SOC or PT level) that demonstrated a statistically significantly (P<=0.05) or borderline significantly (0.05<P<0.2) lower incidence or incidence rate in the degarelix arm as compared to leuprolide 7.5 mg were identified.

In the SCS, cardiovascular events were more specifically investigated on more aggregated MedDRA levels, i.e. the incidence, and incidence rates of subject with AEs in the following High Level Group Terms were tabulated by study group and treatment:

HLGT=Central nervous system vascular disorders

HLGT=Cardiac arrhythmias

HLGT=Coronary artery disorders

HLGT=Heart failures

To further substantiate apparent, but potentially isolated evidence on a detailed Preferred Term level that degarelix shows lower incidence rates than leuprolide with regard to specific cardiac disorders, the incidence rates with regard to the above-mentioned HLGTs, as well as the SOC=Cardiac Disorders these HLGTs belong to, were tested with regard to subgroups based on possible risk-factor (cholesterol, BMI, body weight, systolic/diastolic blood pressure, medical history of cardiac disorder, age, pulse). These subgroup analyses were not pre-planned as part of the SCS. By testing statistical significance of risk-factor by treatment (degarelix/leuprolide 7.5 mg) interaction in a time to event analyses (Cox Proportional hazard model) these covariates were screened for potential subgroup effects. Body mass index and to a lesser extent cholesterol were identified accordingly. Next, BMI subgroups (<25, 25 to <30, and 30 kg/m2) and low/normal cholesterol subgroups (4 mmol/L and >4 mmol/L, respectively) were used to test and quantify differences in incidence rates between degarelix and leuprolide, along using the Poisson model mentioned above. Statistically significant lower incidence rate as compared to leuprolide were noted in patients with BMI <25 kg/m2 with regard to SOC=Cardiac Disorders (P=0.0045), HLGT=Coronary artery disorders (P=0.005), and HLGT=Cardiac Arrhythmias (borderline, P=0.056), with Relative risks of respectively 0.242 (95% CI: 0.08-0.67), 0.0 (95% CI: 0.0-0.47), and 0.312 (95% CI: 0.09-1.03]). Statistically significantly lower incidence rate as compared to leuprolide were noted in patients with Cholesterol greater than or equal to 4 mmol/L with regard to HLGT=Cardiac Arrhythmias (P=0.035), with relative risks of respectively 0.41 (95% CI: 0.18-0.94).

See Tables 8-10 for efficacy findings in subgroups from the SCE, Tables 11-19 for subgroup findings from the SCS, and Tables 20-23 for the explorative substantiating subgroup findings on cardiovascular risk. In summary, notable findings include:

Time to testosterone escape during Days 28, 56, . . . , 364 in the age <65 subgroup is significantly superior to LUPRON DEPOT® 7.5 mg for both degarelix dosing regimens (see Table 8 below).

TABLE 8

One year efficacy results for the testosterone endpoints for Controlled Study CS21-in the age <65 subgroup

| Dosing regimen | Probability of testosterone ≤0.5 ng/mL from Day 28 through Day 364 | | | Probability of testosterone ≤0.5 ng/mL from Day 56 through Day 364 | | | Probability of sufficient testosterone response* | | |
|---|---|---|---|---|---|---|---|---|---|
| | (%) | 95% Cl | N | (%) | 95% Cl | N | (%) | 95% Cl | N |
| Degarelix 240@40/80@20 | 97.4% | 82.8;99.6% | 43 | 97.4% | 82.8;99.6% | 43 | 97.4% | 82.8;99.6% | 43 |
| Degarelix 240/160@40 | 96.7% | 78.6;99.5% | 37 | 96.7% | 78.6;99.5% | 37 | 96.7% | 78.6;99.5% | 37 |
| LUPRON DEPOT ® 7.5 mg | 89.5% | 74.3;95.9% | 38 | 89.5% | 74.3;95.9% | 38 | 92.1% | 77.5;97.4% | 38 |
| Log-rank test: | | | | | | | | | |
| Degarelix 240@40/80@20 vs. LUPRON DEPOT ® 7.5 mg | p = 0.1318 | | | p = 0.1318 | | | p = 0.2588 | | |
| Degarelix 240/160@40 vs. LUPRON DEPOT ® 7.5 mg | p = 0.1851 | | | p = 0.1851 | | | p = 0.3373 | | |

Note:
P values as flagging device used only in the Phase 3 study (head to head comparison to LUPRON DEPOT 7.5 mg),
* = 0.01 < P ≤ 0.05,
** = 0.001 < P ≤ 0.01,
*** = P ≤ 0.001 (Fisher exact, two-sided).

Time to PSA failure is significantly (P=0.03) superior in the degarelix 240/80 mg group as compared to LUPRON DEPOT® 7.5 mg in the age >75 year group, and also (P=0.06) significantly better in the <65 age group (see Table 9 below).

TABLE 9

One year efficacy results for the PSA endpoints for Controlled Study CS21—by age subgroups

| Dosing regimen | Probability of no PSA failure* | | |
|---|---|---|---|
| | (%) | 95% CI | N |
| Age (years) = <65 | | | |
| Degarelix 240@40/80@20 | 85.2% | 70.0; 93.1% | 43 |
| Degarelix 240/160@40 | 71.6% | 53.6; 83.6% | 37 |
| LUPRON DEPOT ® 7.5 mg | 68.2% | 50.9; 80.6% | 38 |
| Log-rank test: | | | |
| Degarelix 240@40/80@20 vs. LUPRON DEPOT ® 7.5 mg | p = 0.0679 | | |
| Degarelix 240/160@40 vs. LUPRON DEPOT ® 7.5 mg | p = 0.7273 | | |
| Age (years) = >=75 | | | |
| Degarelix 240@40/80@20 | 96.6% | 87.0; 99.1% | 78 |
| Degarelix 240/160@40 | 94.5% | 85.9; 97.9% | 82 |
| LUPRON DEPOT ® 7.5 mg | 86.8% | 77.4; 92.5% | 92 |
| Log-rank test: | | | |
| Degarelix 240@40/80@20 vs. LUPRON DEPOT ® 7.5 mg | p = 0.0376. | | |
| Degarelix 240/160@40 vs. LUPRON DEPOT ® 7.5 mg | p = 0.1125 | | |

Note:
P values as flagging device used only in the Phase 3 study (head to head comparison to LUPRON DEPOT 7.5 mg),
* = 0.01 < P ≤ 0.05,
** = 0.001 < P ≤ 0.01,
*** = P ≤ 0.001 (Fisher exact, two-sided).

PSA percent change from baseline is more pronounced in the patients with metastatic stage prostate cancer (See Table 10 below). All subgroups are statistically significantly better than LUPRON DEPOT® 7.5 mg.

TABLE 10

Effect of starting dose on PSA during first month of treatment for Controlled Study CS21-by stage of prostate cancer subgroups

| Day 0 dose | Day 14 percentage change in PSA | | | Day 28 percentage change in PSA | | |
|---|---|---|---|---|---|---|
| | Median % | InterQuartile Range | N | Median % | InterQuartile Range | N |
| PCA = Localized | | | | | | |
| Degarelix 240@40 | −50.6% | −65.0;−30.4% | 128 | −75.0% | −85.2;−60.5% | 128 |
| LUPRON DEPOT ® 7.5 mg | −13.2% | −29.3;−0.518% | 63 | −55.7% | −66.7;−33.8% | 63 |
| Wilcoxon rank sum test: | | | | | | |
| Degarelix 240@40 vs. LUPRON DEPOT ® 7.5 mg | p = <.0001 | | | p = <.0001 | | |
| PCA-Locally advanced | | | | | | |
| Degarelix 240@40 | −66.6% | −75.9;−49.6% | 126 | −84.1% | −91.8;−75.0% | 126 |
| LUPRON DEPOT ® 7.5 mg | −21.3% | −36.2;−9.20% | 52 | −73.2% | −84.0;−50.0% | 52 |

TABLE 10-continued

Effect of starting dose on PSA during first month of treatment for Controlled Study CS21-by stage of prostate cancer subgroups

| Day 0 dose | Day 14 percentage change in PSA | | | Day 28 percentage change in PSA | | |
|---|---|---|---|---|---|---|
| | Median % | InterQuartile Range | N | Median % | InterQuartile Range | N |
| Wilcoxon rank sum test: | | | | | | |
| Degarelix 240@40 vs. LUPRON DEPOT® 7.5 mg | p = .0001 | | | p = <.0001 | | |
| PCA = Metastatic | | | | | | |
| Degarelix 240@40 | −77.9% | −85.3;−62.3% | 78 | −89.9% | −95.6;−83.1% | 78 |
| LUPRON DEPOT® 7.5 mg | −25.3% | −53.2;−0.943% | 47 | −79.7% | −90.6;−70.7% | 47 |
| Wilcoxon rank sum test: | | | | | | |
| Degarelix 240@40 vs. LUPRON DEPOT® 7.5 mg | p = <.0001 | | | p = 0.0003 | | |

Note:
P values as flagging device used only in the Phase 3 study (head to head comparison to LUPRON DEPOT 7.5 mg),
* = 0.01 < P ≤ 0.05,
** = 0.001 < P ≤ 0.01,
*** = P ≤ 0.001(Fisher exact, two-sided).

Notable statistically significant findings in the total trial population are (See Table 11):

Myocardial Infarction (PT): 0.5% (2/409, degarelix combined) versus 2.5% (5/201, LUPRON DEPOT® 7.5 mg), Oedema peripheral (PT) 2% (8/409, degarelix combined) versus 5% (10/201, LUPRON DEPOT® 7.5 mg), Chest pain: 0.5% (2/409, degarelix combined) versus 3% (6/201, LUPRON DEPOT® 7.5 mg), Urinary Tract infection (PT) 3% (13/409, degarelix combined) versus 9% (18/201, LUPRON DEPOT® 7.5 mg), Cardiac murmur (PT): 0% (0/409, degarelix combined) versus 1.5% (3/201, LUPRON DEPOT®7.5 mg), Musculoskeletal and connective tissue disorders (SOC): 17% (68/409, degarelix combined) versus 26% (53/201, LUPRON DEPOT® 7.5 mg), Arthralgia (PT within Musculoskeletal and CTD SOC): 4.2% (17/409, degarelix combined) versus 9% (18/201, LUPRON DEPOT® 7.5 mg), Musculoskeletal stiffness (PT within Musculoskeletal and CTD SOC): 0% (0/409, degarelix combined) versus 1% (3/201, LUPRON DEPOT® 7.5 mg), Libido decreased: 0% (0/409, degarelix combined) versus 1.5% (3/201, LUPRON DEPOT®7.5 mg), Urinary retention: 1.2% (5/409, degarelix combined) versus 4.5% (9/201, LUPRON DEPOT®7.5 mg), Cystitis noninfective: 0% (0/409, degarelix combined) versus 2% (4/201, LUPRON DEPOT®7.5 mg), Erectile dysfunction: 1.5% (6/409, degarelix combined) versus 4.5% (9/201, LUPRON DEPOT®7.5 mg), DVT: 0% (0/409, degarelix combined) versus 1.5% (3/201, LUPRON DEPOT® 7.5 mg).

Particularly notable statistically significant findings in and across subgroups are indicated.

TABLE 11

Crude Incidence of Treatment-Emergent Adverse Events by MedDRA System Organ Class and Preferred Term

| | One-Month Controlled | |
|---|---|---|
| MedDRA System Organ Class/Preferred Term | Degarelix N (%) | LUPRON DEPOT® 7.5 mg N (%) |
| Exposed Subjects | 409 (100%) | 201 (100%) |
| Total No. of Subjects with Adverse Events | 330 (81%) | 156 (78%) |
| BLOOD AND LYMPHATIC SYSTEM DISORDERS | 16 (4%) | 12 (6%) |
| Myocardial ischaemia | 2 (<1%)* | 5 (2%)* |
| GENERAL DISORDERS AND ADMINISTRATION SITE CONDITIONS | | |
| Oedema peripheral | 8 (2%)* | 10 (5%)* |
| Chest pain | 2 (<1%)* | 6 (3%)* |
| INFECTIONS AND INFESTATIONS | | |
| Urinary tract infection | 13 (3%)** | 18 (9%)** |
| INVESTIGATIONS | 113 (28%) | 62 (31%) |
| Cardiac murmur | | 3 (1%)* |
| MUSCULOSKELETAL AND CONNECTIVE TISSUE DISORDERS | 68 (17%)** | 53 (26%)** |
| Arthralgia | 17 (4%)* | 18 (9%)* |
| Musculoskeletal stiffness | | 3 (1%)* |
| PSYCHIATRIC DISORDERS | | |
| Libido decreased | 0 | 3 (1%)* |
| RENAL AND URINARY DISORDERS | | |
| Urinary retention | 5 (1%)* | 9 (4%)* |
| Cystitis noninfective | | 4 (2%)* |
| REPRODUCTIVE SYSTEM AND BREAST DISORDERS | 22 (5%)* | 21 (10%)* |
| Erectile dysfunction | 6 (1%)* | 9 (4%)* |
| VASCULAR DISORDERS | | |
| Deep vein thrombosis | 0 | 3 (1%)* |

Note:
P values as flagging device used only in the Phase 3 study (head to head comparison to LUPRON DEPOT 7.5 mg),
* = 0.01 < P ≤ 0.05,
** = 0.001 < P ≤ 0.01,
*** = P ≤ 0.001(Fisher exact, two-sided).

Musculoskeletal and connective tissue disorders (SOC) and Arthralgia superiority is not just confined to the metastatic, but in all disease stage subgroup (see Table H=Table 2.2). Arthralgia is statistically significant in locally advanced patients.

TABLE 12

Crude Incidence of Treatment-Emergent Adverse Events by MedDRA System Organ Class and Preferred Term—by Stage of Prostate Cancer

| | One-Month Controlled | |
|---|---|---|
| MedDRA System Organ Class/Preferred Term | Degarelix N (%) | LUPRON DEPOT® 7.5 mg N (%) |
| PCA = Localised | | |
| Exposed Subjects | 128 (100%) | 63 (100%) |
| Total No. of Subjects with Adverse Events | 104 (81%) | 48 (76%) |

TABLE 12-continued

Crude Incidence of Treatment-Emergent Adverse Events by MedDRA System Organ Class and Preferred Term—by Stage of Prostate Cancer

|  | One-Month Controlled | |
|---|---|---|
| MedDRA System Organ Class/Preferred Term | Degarelix N (%) | LUPRON DEPOT® 7.5 mg N (%) |
| GENERAL DISORDERS AND ADMINISTRATION SITE CONDITIONS | | |
| Oedema peripheral | 2 (2%)* | 6 (10%)* |
| INFECTIONS AND INFESTATIONS | 22 (17%) | 14 (22%) |
| Urinary tract infection | 2 (2%)* | 5 (8%)* |
| Upper respiratory tract infection | 4 (3%) | 6 (10%) |
| MUSCULOSKELETAL AND CONNECTIVE TISSUE DISORDERS | 20 (16%) | 16 (25%) |
| NEOPLASMS BENIGN, MALIGNANT AND UNSPECIFIED (INCL CYSTS AND POLYPS) | 4 (3%) | 6 (10%) |
| PSYCHIATRIC DISORDERS | 11 (9%) | 9 (14%) |
| Depression | 1 (<1%)* | 4 (6%)* |
| Libido decreased |  | 2 (3%) |
| REPRODUCTIVE SYSTEM AND BREAST DISORDERS | 5 (4%) | 7 (11%) |
| Gynaecomastia | 1 (<1%) | 2 (3%) |
| Erectile dysfunction | 1 (<1%)* | 4 (6%)* |
| PCA = Locally advanced | | |
| Exposed Subjects | 126 (100%) | 52 (100%) |
| Total No. of Subjects with Adverse Events | 93 (74%) | 37 (71%) |
| CARDIAC DISORDERS | 4 (3%) | 5 (10%) |
| Atrioventricular block first degree |  | 3 (6%)* |
| GASTROINTESTINAL DISORDERS | 16 (13%) | 11 (21%) |
| Diarrhoea | 1 (<1%)* | 4 (8%)* |
| INFECTIONS AND INFESTATIONS | 16 (13%) | 11 (21%) |
| Urinary tract infection | 1 (<1%)** | 5 (10%)** |
| INJURY, POISONING AND PROCEDURAL COMPLICATIONS | 2 (2%)** | 6 (12%)** |
| Fall | 1 (<1%) | 1 (2%) |
| Excoriation |  | 2 (4%) |
| Muscle strain | 1 (<1%) |  |
| MUSCULOSKELETAL AND CONNECTIVE TISSUE DISORDERS | 13 (10%) | 10 (19%) |
| Back pain | 6 (5%) | 4 (8%) |
| Arthralgia | 2 (2%)** | 7 (13%)** |
| RESPIRATORY, THORACIC AND MEDIASTINAL DISORDERS | 9 (7%) | 5 (10%) |
| Dyspnoea | 0 | 3 (6%)* |
| PCA = Metastatic | | |
| Exposed Subjects | 78 (100%) | 47 (100%) |
| Total No. of Subjects with Adverse Events | 63 (81%) | 39 (83%) |
| GASTROINTESTINAL DISORDERS | 12 (15%) | 12 (26%) |
| MUSCULOSKELETAL AND CONNECTIVE TISSUE DISORDERS | 16 (21%) | 17 (36%) |
| Back pain | 4 (5%) | 6 (13%) |
| Arthralgia | 4 (5%) | 6 (13%) |
| Pain in extremity | 1 (1%) | 4 (9%) |

Note:
P values as flagging device used only in the Phase 3 study (head to head comparison to LUPRON DEPOT 7.5 mg),
* = 0.01 < P ≤ 0.05,
** = 0.001 < P ≤ 0.01,
*** = P ≤ 0.001 (Fisher exact, two-sided).

Renal And Urinary Disorders and Musculoskeletal and Connective Tissue disorders in Age <65 group (see Table 13)

TABLE 13

Crude Incidence of Treatment-Emergent Adverse Events by MedDRA System Organ Class and Preferred Term—in the age <65 subgroup
Age (years) = <65

|  | One-Month Controlled | |
|---|---|---|
| MedDRA System Organ Class/Preferred Term | Degarelix N (%) | LUPRON DEPOT® 7.5 mg N (%) |
| Exposed Subjects | 80 (100%) | 38 (100%) |
| Total No. of Subjects with Adverse Events | 60 (75%) | 31 (82%) |
| GASTROINTESTINAL DISORDERS | 7 (9%)* | 9 (24%)* |
| INFECTIONS AND INFESTATIONS | 13 (16%) | 10 (26%) |
| MUSCULOSKELETAL AND CONNECTIVE TISSUE DISORDERS | 7 (9%)** | 13 (34%)** |
| Arthralgia |  | 5 (13%)** |
| RENAL AND URINARY DISORDERS | 8 (10%)* | 11 (29%)* |
| Urinary retention | 1 (1%)* | 5 (13%)* |

Note:
No findings in the other age-categories

Note:
P values as flagging device used only in the Phase 3 study (head to head comparison to LUPRON DEPOT 7.5 mg),
* = 0.01 < P ≤ 0.05,
** = 0.001 < P ≤ 0.01,
*** = P ≤ 0.001 (Fisher exact, two-sided).

See Table 14 and Table 15 for further subgroup findings.

TABLE 14

Crude Incidence of Treatment-Emergent Adverse Events by MedDRA System Organ Class and Preferred Term—by Body Weight categories

|  | One-Month Controlled | |
|---|---|---|
| MedDRA System Organ Class/Preferred Term | Degarelix N (%) | LUPRON DEPOT® 7.5 mg N (%) |
| Weight (kg) = <70 | | |
| Exposed Subjects | 102 (100%) | 39 (100%) |
| Total No. of Subjects with Adverse Events | 80 (78%) | 30 (77%) |
| MUSCULOSKELETAL AND CONNECTIVE TISSUE DISORDERS | 17 (17%)* | 14 (36%)* |
| Arthralgia | 3 (3%)** | 7 (18%)** |
| REPRODUCTIVE SYSTEM AND BREAST DISORDERS | 4 (4%)* | 7 (18%)* |
| Pelvic pain | 0 | 3 (8%)* |
| Weight (kg) = 70-<90 | | |
| Exposed Subjects | 227 (100%) | 125 (100%) |
| Total No. of Subjects with Adverse Events | 183 (81%) | 95 (76%) |
| CARDIAC DISORDERS | 12 (5%)* | 16 (13%)* |
| NERVOUS SYSTEM DISORDERS | 27 (12%) | 13 (10%) |
| Syncope |  | 3 (2%)* |
| REPRODUCTIVE SYSTEM AND BREAST DISORDERS | 11 (5%) | 10 (8%) |
| Erectile dysfunction | 2 (<1%)* | 7 (6%)* |
| Weight (kg) = >=90 | | |
| Exposed Subjects | 80 (100%) | 37 (100%) |
| Total No. of Subjects with Adverse Events | 67 (84%) | 31 (84%) |
| INFECTIONS AND INFESTATIONS | 21 (26%) | 12 (32%) |
| Urinary tract infection | 2 (3%)* | 5 (14%)* |
| Bronchitis |  | 3 (8%)* |
| MUSCULOSKELETAL AND CONNECTIVE TISSUE DISORDERS | 12 (15%)* | 12 (32%)* |

TABLE 14-continued

Crude Incidence of Treatment-Emergent Adverse Events by MedDRA System Organ Class and Preferred Term—by Body Weight categories

| | One-Month Controlled | |
|---|---|---|
| MedDRA System Organ Class/Preferred Term | Degarelix N (%) | LUPRON DEPOT ® 7.5 mg N (%) |
| Arthralgia | 4 (5%) | 4 (11%) |
| Back pain | 4 (5%)* | 7 (19%)* |
| NEOPLASMS BENIGN, MALIGNANT AND UNSPECIFIED (INCL CYSTS AND POLYPS) | 1 (1%)* | 4 (11%)* |

Note:
P values as flagging device used only in the Phase 3 study (head to head comparison to LUPRON DEPOT 7.5 mg),
* = $0.01 < P \leq 0.05$,
** = $0.001 < P \leq 0.01$,
*** = $P \leq 0.001$ (Fisher exact, two-sided).

TABLE 15

Crude Incidence of Treatment-Emergent Adverse Events by MedDRA System Organ Class and Preferred Term—by Race

| | One-Month Controlled | |
|---|---|---|
| MedDRA System Organ Class/Preferred Term | Degarelix N (%) | LUPRON DEPOT ® 7.5 mg N (%) |
| Race = White | | |
| Exposed Subjects | 339 (100%) | 172 (100%) |
| Total No. of Subjects with Adverse Events | 267 (79%) | 131 (76%) |
| CARDIAC DISORDERS | 33 (10%) | 25 (15%) |
| Myocardial ischaemia | 2 (<1%)* | 5 (3%)* |
| GENERAL DISORDERS AND ADMINISTRATION SITE CONDITIONS | | |
| Oedema peripheral | 5 (1%)* | 10 (6%)* |
| Chest pain | 2 (<1%)* | 5 (3%)* |
| INFECTIONS AND INFESTATIONS | 64 (19%) | 39 (23%) |
| Upper respiratory tract infection | 3 (<1%)* | 7 (4%)* |
| INVESTIGATIONS | 88 (26%) | 52 (30%) |
| Cardiac murmur | | 3 (2%)* |
| MUSCULOSKELETAL AND CONNECTIVE TISSUE DISORDERS | 52 (15%)** | 44 (26%)** |
| Musculoskeletal stiffness | 0 | 3 (2%)* |
| RENAL AND URINARY DISORDERS | 46 (14%) | 34 (20%) |
| Urinary retention | 4 (1%)* | 7 (4%)* |
| RENAL AND URINARY DISORDERS (cont.) | | |
| Cystitis noninfective | 0 | 4 (2%)* |
| VASCULAR DISORDERS | 106 (31%) | 52 (30%) |
| Orthostatic hypotension | 0 | 3 (2%)* |
| Deep vein thrombosis | 0 | 3 (2%)* |
| Race = Other | | |
| Exposed Subjects | 42 (100%) | 19 (100%) |
| Total No. of Subjects with Adverse Events | 40 (95%) | 16 (84%) |
| INFECTIONS AND INFESTATIONS | 14 (33%) | 7 (37%) |
| Urinary tract infection | 2 (5%)* | 5 (26%)* |
| REPRODUCTIVE SYSTEM AND BREAST DISORDERS | 4 (10%) | 5 (26%) |
| Erectile dysfunction | 1 (2%)* | 4 (21%)* |

Note:
no findings in Blacks

Note:
P values as flagging device used only in the Phase 3 study (head to head comparison to LUPRON DEPOT 7.5 mg),
* = $0.01 < P \leq 0.05$,
** = $0.001 < P \leq 0.01$,
*** = $P \leq 0.001$ (Fisher exact, two-sided).

These results shown in Tables 16 and 17 below demonstrate that treated subjects had a significantly reduced risk of developing coronary artery disease, heart failure, myocardial infarction, cardiac arrhythmia, coronary artery disease or heart failure when receiving androgen depletion therapy with degarelix as compared to Lupron.

TABLE 16

Incidence Rate (in 1,000 py) of Cardiovascular Events compared to Background Incidence Rates

| | Degarelix | | | | LUPRON DEPOT ® 7.5 mg | | | | |
|---|---|---|---|---|---|---|---|---|---|
| CV Event type | N (%) | PY | Incidence Rate | 95% CI | N (%) | PY | Incidence Rate | 95% CI | |
| Stroke | 3 (<1%) | 0.354 | 8.49 | [1.75; 24.8] | 1 (<1%) | 0.178 | 5.63 | [0.142; 31.4] | P = 1.0 |
| Coronary artery disease | 12 (3%) | 0.351 | 34.2 | [17.7; 59.7] | 11 (5%) | 0.174 | 63.4 | [31.6; 113] | P = 0.2 |
| Heart failure | 5 (1%) | 0.354 | 14.1 | [4.59; 33.0] | 5 (2%) | 0.176 | 28.4 | [9.21; 66.2] | P = 0.42 |

TABLE 16-continued

Incidence Rate (in 1,000 py) of Cardiovascular Events compared to Background Incidence Rates

| | Degarelix | | | | LUPRON DEPOT ® 7.5 mg | | | | |
|---|---|---|---|---|---|---|---|---|---|
| | N (%) | PY | Incidence Rate | 95% CI | N (%) | PY | Incidence Rate | 95% CI | |
| MI | 2 (<1%) | 0.354 | 5.64 | [0.683; 20.4] | 4 (2%) | 0.177 | 22.6 | [6.15; 57.8] | P = 0.2 |

Note:
P values as flagging device used only in the Phase 3 study (head to head comparison to LUPRON DEPOT 7.5 mg),
* = 0.01 < P ≤ 0.05,
** = 0.001 < P ≤ 0.01,
*** = P ≤ 0.001 (Fisher exact, two-sided).

TABLE 17

Incidence Rate of Cardiovascular Events defined by High Level Group Terms

| | Degarelix | | | | LUPRON DEPOT ® 7.5 mg | | | | |
|---|---|---|---|---|---|---|---|---|---|
| | N (%) | PY | Incidence Rate | 95% CI | N (%) | PY | Incidence Rate | 95% CI | |
| MedDRA HLGT | | | | | | | | | |
| Central nervous system vascular disorders | 5 (<1%) | 0.353 | 14.2 | [4.60; 33.1] | 1 (<1%) | 0.178 | 5.63 | [0.142; 31.4] | P = 0.69 |
| Cardiac arrhythmias | 20 (5%) | 0.347 | 57.7 | [35.3; 89.1] | 17 (8%) | 0.170 | 100 | [58.2; 160] | P = 0.13 |
| Coronary artery disorders | 12 (3%) | 0.351 | 34.2 | [17.7; 59.7] | 11 (5%) | 0.174 | 63.4 | [31.6; 113] | P = 0.21 |
| Heart failures | 5 (<1%) | 0.354 | 14.1 | [4.59; 33.0] | 5 (2%) | 0.176 | 28.4 | [9.21; 66.2] | P = 0.42 |

Note:
P values as flagging device used only in he Phase 3 study (head to head comparison to LUPRON DEPOT 7.5 mg),
* = 0.01 < P ≤ 0.05,
** = 0.001 < P ≤ 0.01,
*** = P 0.001 ≤ (Fisher exact, two-sided).

Mortality Subgroups with Statistically (Pre-Planned as Part of the ISS) Significant Findings

TABLE 18

Mortality by Treatment group
Age (years) = >=65-<75

| Treatment Group | N | No. of Deaths | Crude Mortality | PY of Exposure | Mortality per 1,000 PY Estimate | 95% CI |
|---|---|---|---|---|---|---|
| Degarelix | 169 | 3 | (2%) | 0.148 | 20.2 | [4.17; 59.1] |
| LUPRON DEPOT ® 7.5 mg | 71 | 6 | (8%) | 0.061 | 99.0 | [36.3; 216] |
| Test for homogeneity of mortality rates: | P = 0.0426 | | | | | |

TABLE 19

Mortality by Treatment group
PCA = Localized

| Treatment Group | N | No. of Deaths | Crude Mortality | PY of Exposure | Mortality per 1,000 PY Estimate | 95% CI |
|---|---|---|---|---|---|---|
| Degarelix | 128 | 0 | (0%) | 0.113 | 0 | [0, 32.6] |
| LUPRON DEPOT ® 7.5 mg | 63 | 4 | (6%) | 0.057 | 70.3 | [19.2; 180] |
| Test for homogeneity of mortality rates: | P = 0.025 | | | | | |

TABLE 20

Incidence rates ratios by BMI of Cardiac
Arrhythmias in CS21-Degarelix vs Luprolide

| Body Mass Index Category | Degarelix | | Lupron | | Relative Risk | | |
|---|---|---|---|---|---|---|---|
| | Incidence Rate | 95% CI | Incidence Rate | 95% CI | RR | 95% CI | P value (a) |
| 1: <25 kg/m2 | 46.58 | (17.1-101) | 149.3 | (64.4-294) | 0.312 | (0.09-1.03) | .0556 |
| 2: 25-<30 kg/m2 | 52.66 | (24.1-100) | 93.09 | (40.2-183) | 0.566 | (0.19-1.68) | .3495 |
| 3: >= 30 kg/m2 | 84.50 | (27.4-197) | 26.73 | (0.68-149) | 3.161 | (0.35-150) | .5069 |

(a) P value for for homogeneity of incidence rates
PY in 1,000 person years

These results show that treated subjects with BMIs of less than 30 kg/m² (e.g., less than 25 kg/m², e.g., 20-25 kg/m²) had a significantly reduced risk of developing a cardiac arrhythmia when receiving androgen depletion therapy with degarelix as compared to Lupron.

TABLE 21

Incidence rates ratios by BMI of Coronary
Artery Disorders in CS21-Degarelix vs Luprolide

| Body Mass Index Category | Degarelix | | Lupron | | Relative Risk | | |
|---|---|---|---|---|---|---|---|
| | Incidence Rate | 95% CI | Incidence Rate | 95% CI | RR | 95% CI | P value (a) |
| 1: <25 kg/m2 | 0.00 | (0.00-28.0) | 87.96 | (28.6-205) | 0.000 | (0.00-0.47) | 0.0050 |
| 2: 25-<30 kg/m2 | 46.88 | (20.2-92.4) | 46.27 | (12.6-118) | 1.013 | (0.27-4.60) | 1.000 |
| 3: >=30 kg/m2 | 65.16 | (17.8-167) | 53.53 | (6.48-193) | 1.217 | (0.17-13.5) | 1.000 |

(a) P value for homogeneity of incidence rates
PY in 1,000 person years

These results show that treated subjects with BMIs of less than 25 kg/m² (e.g., 20-25 kg/m²) had a significantly reduced risk of developing a coronary artery disorder when receiving androgen depletion therapy with degarelix as compared to Lupron.

TABLE 22

Incidence rates ratios by BMI of Cardiac
Disorders (SOC) in CS21-Degarelix vs Luprolide

| Body Mass Index Category | Degarelix | | Lupron | | Relative Risk | | |
|---|---|---|---|---|---|---|---|
| | Incidence Rate | 95% CI | Incidence Rate | 95% CI | RR | 95% CI | P value (a) |
| 1: <25 kg/m2 | 54.32 | (21.8-112) | 224.9 | (116-393) | 0.242 | (0.08-0.67) | .0045 |
| 2: 25-<30 kg/m2 | 101.5 | (59.1-162) | 132.6 | (66.2-237) | 0.765 | (0.34-1.81) | .6106 |
| 3: >= 30 kg/m2 | 209.6 | (108-366) | 107.7 | (29.4-276) | 1.946 | (0.59-8.28) | .3606 |

(a) P value for for homogeneity of incidence rates
PY in 1,000 person years

These results show that treated subjects with BMIs of less than 30 kg/m² (e.g., less than 25 kg/m², e.g. 20-25 kg/m²) had a significantly reduced risk of developing a cardiac disorder when receiving androgen depletion therapy with degarelix as compared to Lupron.

TABLE 23

Incidence rates ratios by Cholesterol of Cardiac
Arrhythmias in CS21-Degarelix vs Luprolide

| Cholesterol Category | Degarelix | | Lupron | | Relative Risk | | |
|---|---|---|---|---|---|---|---|
| | Incidence Rate | 95% CI | Incidence Rate | 95% CI | RR | 95% CI | P value (a) |
| 1: <4 mmol/L | 156.1 | (62.8-322) | 79.12 | (16.3-231) | 1.973 | (0.45-11.8) | .4981 |
| 2: >= 4 mmol/L | 41.39 | (22.0-70.8) | 100.7 | (55.1-169) | 0.411 | (0.18-0.94) | .0350 |

(a) P value for homogeneity of incidence rates
PY in 1,000 person years

These results show that treated subjects with cholesterol levels of greater than or equal to 4 mmol/L had a significantly reduced risk of developing a cardiac arrhythmia when receiving androgen depletion therapy with degarelix as compared to GnRH antagonist therapy with Lupron.

EQUIVALENTS

Those skilled in the art will recognize, or be able to ascertain, using no more than routine experimentation, numerous equivalents to the specific embodiments described herein. Such equivalents are intended to be encompassed in the scope of the following claims.

Example 2: Clinical Study Comparing Cardiovascular Event Rates Using GnRH Antagonist Versus Agonist In this example, a study was conducted to investigate the risk of cardiovascular events when ADT is utilized by a GnRH antagonist versus agonist in patients with or without a history of cardiovascular events.

Specifically, this study utilized available data yielding a safety database of 2328 PCa (prostate cancer) patients who participated in randomized clinical trials and received treatment with either degarelix or a GnRH agonist for up to 12 months (13 treatment months). Justification for performing the comparison over this relatively short treatment period comes from numerous observations indicating that the increased risk of cardiovascular (CV) morbidities associated with the use of GnRH agonists was detectable during the first 12 months of treatment (Saigal et al. (2007) Cancer 110:1493-500) and as early as after 1-4-month (Keating et al. (2006) J. Clin. Oncol. 24:4448-56) or 6-month (D'Amico et al. (2007) J. Clin. Oncol. 25:2420-2425) exposure.

Study Design

Figure 7:
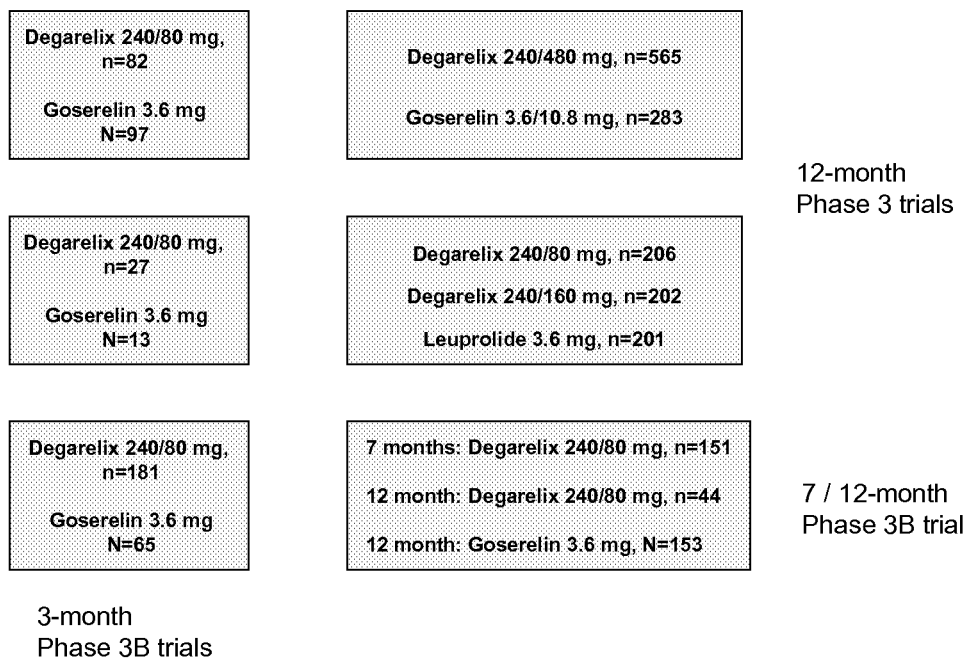
FIG. 7 is a graphical representation of the six randomized clinical trials included in Example 2, which illustrate the number of patients and doses of the drugs utilized for androgen deprivation therapy and time periods of these trials.

The study is based on data from two completed Phase 3 and 4 Phase 3b trials, all of which used an active comparator in form of a GnRH agonist. In each study, the primary inclusion criteria were male subjects ≥8 years of age with histologically confirmed adenocarcinoma of the prostate in whom ADT was indicated and a life expectancy of minimum 12 months could be anticipated. All subjects had serum testosterone levels that were either within the age-specified normal range or above the lower limit of the normal range of the central laboratory and ECOG score ≤2. Exclusion criterion ensured that none of the subjects had received long-term ADT (>6 months) before study entry. The number of patients and drug doses utilized for each trial are summarized in FIG. 7.

The clinical trials were performed in accordance with the Declaration of Helsinki and Good Clinical Practice guidelines. The respective study protocols were approved by independent Ethics Committees and Institutional Review Boards.

Baseline evaluation included thorough collection of the main demographic characteristics (age, weight, height), lifestyle factors (smoking and drinking habits), and major CV risk factors (treated type 2 diabetes, treated hyperlipidemia, treated hypertension, and systolic and diastolic blood pressure). Patients also underwent physical examination and ECG assessment for potential cardiac morbidities. Medical history of CV events was captured by the following Standardized MedDRA Queries (myocardial infarction, ischemic heart diseases, ischemic stroke, hemorrhagic stroke, other arterial thrombotic/embolic events).

Serum testosterone was typically measured at baseline and then monthly in all cases. Serum testosterone was measured at a central laboratory using a validated liquid chromatography system with a tandem mass spectrometry assay with a lower limit of quantitation of 3 ng/dl.

Cardiovascular events of interest were collected prospectively, typically at monthly visits, as adverse events or serious adverse events with date of occurrence. These events were coded using standard MedDRA terms and grouped into one of the same categories as those used to collect medical history.

Statistical Methods

The CV event rates in agonist and antagonist-treated patients were analyzed by 1-Kaplan-Meier plots of time to first-reported CV events and compared with log-rank test. The analysis was performed separately for strata of patients with or without history of CV events. To identify independent predictors of CV events we applied multivariate Cox proportional hazards models. All analyses were done at the 5% nominal significance level using SAS®, version 9.2.

Results

Baseline characteristics of the population stratified according to treatment received are outlined in Table 24. Reflecting the fact that the data come from randomized clinical trials, patient characteristics were balanced throughout the parameters listed. History of CV events was reported by approximately one third of the patients in both treatment arms.

TABLE 24

Baseline characteristics of prostate cancer patients stratified according to received treatment.

|  | DEGARELIX N = 1491 | AGONIST N = 837 |
|---|---|---|
| Age, years (SD) | 71.7 (8.1) | 71.6 (8.1) |
| BMI, kg/m² (SD) | 27.2 (4.4) | 27.5 (4.4) |
| BMI kg/m² | 22.4% | 23.9% |
| Serum testosterone (ng/ml) | 4.32 (1.84) | 4.36 (1.78) |
| Regular alcohol consumption, yes % | 56.3% | 54% |
| Ever smoking, yes % | 48.6% | 52.2% |
| Heart rate, beat per minute (SD) | 71 (11) | 71 (11) |
| Systolic blood pressure, mmHg (SD) | 137 (17) | 137 (16) |
| Diastolic blood pressure, mmHg (SD) | 79 (10) | 79 (10) |
| Systolic blood pressure >140 mmHg or Diastolic blood pressure >90 mmHg | 33% | 33% |
| Treated hypertension, yes % | 27.9% | 28.4% |
| Treated hyperlipidemia, yes % | 26.8% | 27.8% |
| Treated type 2 diabetes, yes % | 11.9% | 11.2% |
| History of CV event *, yes % * | 31.1% | 33.7% |
| Prostata cancer stage |  |  |
| Localized | 34.4% | 34.3% |
| Locally advanced | 25.8% | 22.2% |
| Metastatic | 18.9% | 18.4% |
| Non-classifiable | 20.9% | 25.1% |

Median exposure to the antagonist or the agonists was 11.96 treatment months. Short-term exposure <7 months was received by one third of the patients (agonist 242 [28.9%]; degarelix: 417 [28.0%]), whereas >7 months exposure was received by two third (agonist: 595 [71.1%], degarelix: 1074 [72.0%]).

Figure 8:
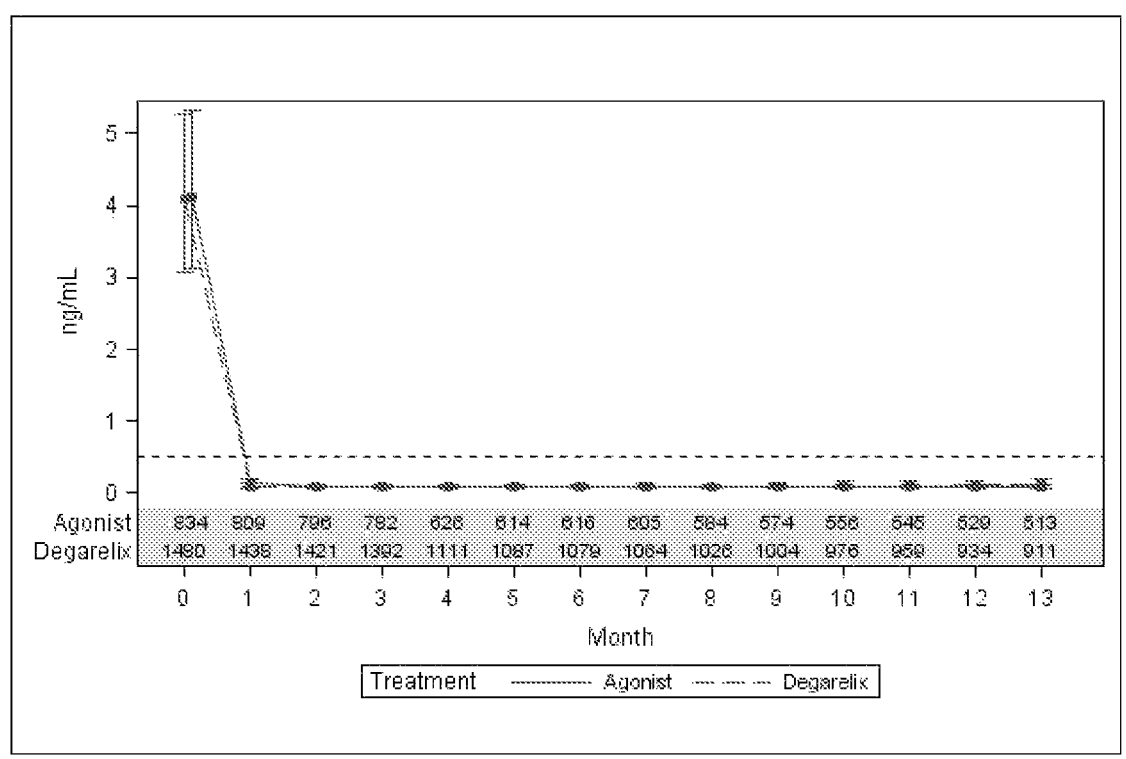
FIG. 8 is a graphical representation showing the median (±interquartile range) of serum testosterone level during androgen deprivation therapy with either degarelix or a standard GnRH agonist of Example 2.

Median testosterone levels monitored on a monthly basis throughout the respective treatment periods are outlined in FIG. 8. From Day 28 (Month 1), testosterone was suppressed to comparable levels (below castration level <0.5 ng/ml) in all clinical trials by both the agonist and degarelix.

During the treatment period, 81 patients reported at least one CV event. For 39 patients, this was already a secondary event (i.e., an additional cardiovascular event), whereas for 42 patients it was a primary event. By these 81 patients, a total of 153 CV events were reported reflecting that one patient could report several events at a time and/or during the course of the treatment. Details on the type of CV events and their distribution between treatment arms are listed in Table 25.

TABLE 25

Frequency of various cardiovascular events per treatment arm

|  | DEGARELIX N = 1491 | | | | AGONIST N = 837 | | | |
|---|---|---|---|---|---|---|---|---|
|  | N | % | E | % | N | % | E | % |
| Any CV adverse event | 44 | 2.9% | 90 | 6.0% | 37 | 4.4% | 63 | 7.5% |
| Myocardial infarction | 13 | 0.8% | 15 | 1.0% | 11 | 1.3% | 11 | 1.3% |
| Ischemic heart disease | 25 | 1.7% | 27 | 1.8% | 17 | 2.0% | 18 | 2.2% |
| Ischemic stroke | 14 | 0.9% | 16 | 1.1% | 10 | 1.2% | 10 | 1.2% |
| Hemorrhagic stroke | 3 | 0.2% | 3 | 0.2% | 5 | 0.6% | 5 | 0.6% |
| Other embolic or thrombotic events, arterial | 23 | 1.5% | 29 | 1.9% | 17 | 2.0% | 19 | 2.3% |

N = Number of patients with adverse events
E = Number of adverse events

Event Rates in Patients with or without History of CV Events

Figure 9A:
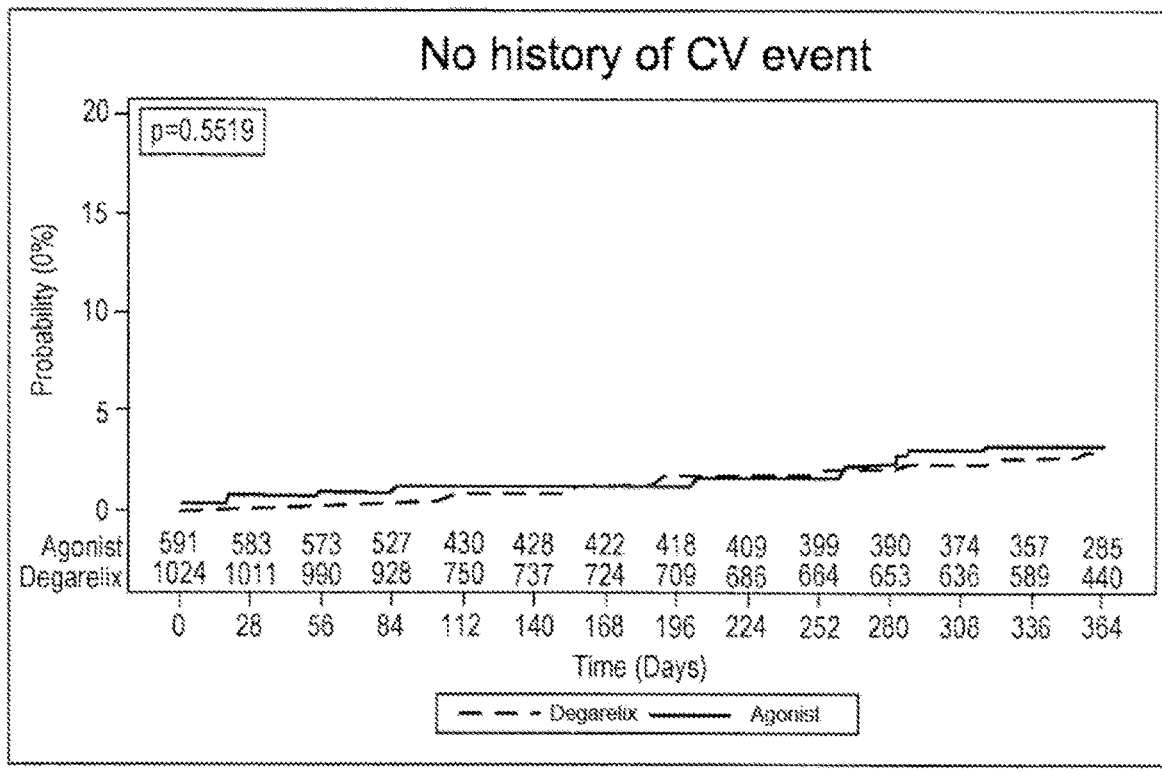
FIGS. 9 A-D are 1-Kaplan-Meier plots of time to first-reported cardiovascular event in prostate cancer patients with and without a history of cardiovascular events in patients receiving treatment with degarelix versus agonist of Example 2.
Figure 9B:
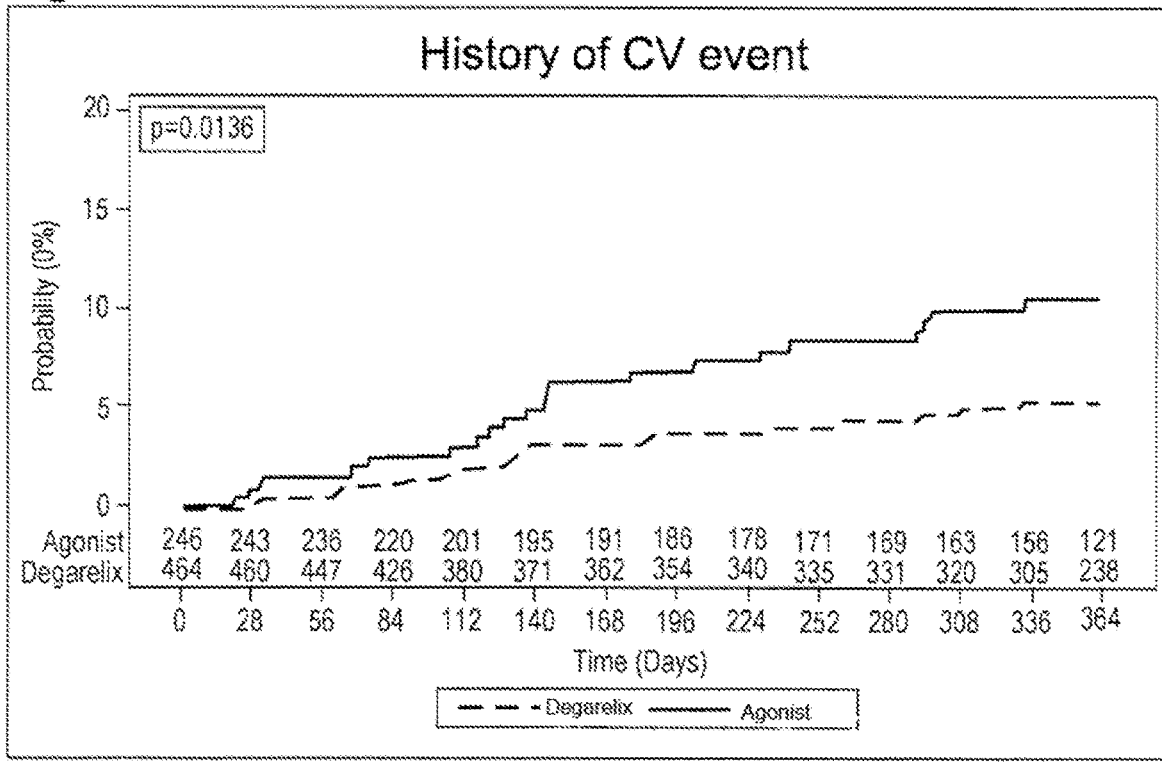
Figure 9C:
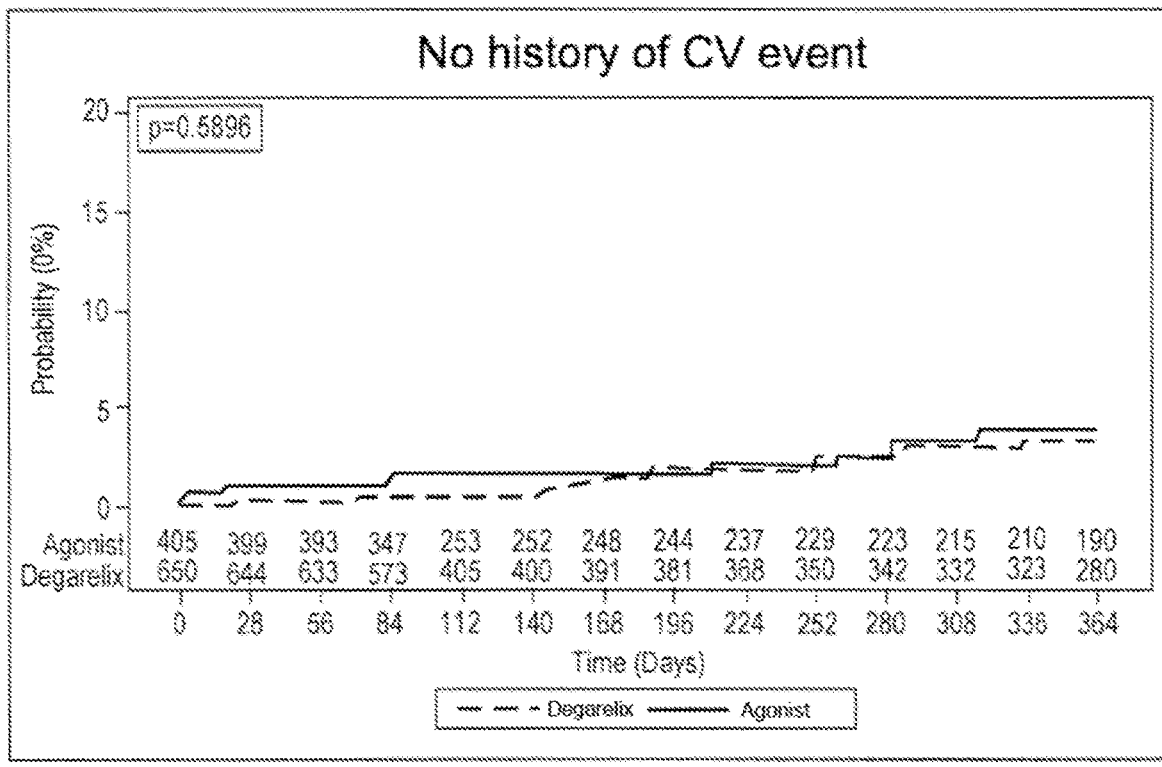
Figure 9D:
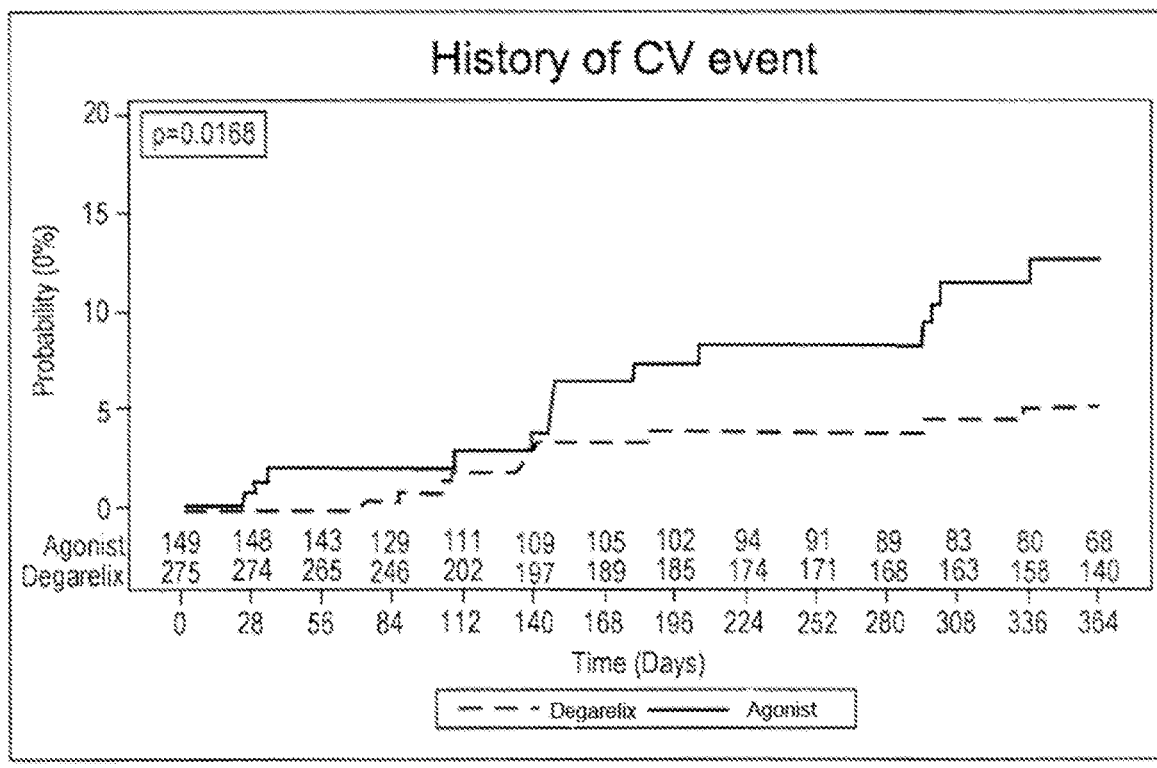

When comparing 1-Kaplan-Meier plots of time to first-reported CV event in degarelix versus agonist treated patients with no history of CV events, the plots were very similar throughout the observation period (FIG. 9A). Corresponding event rates were 6.4 and 4.1 events per 100 Person-year (p=0.11). In contrast, when comparing the plots obtained from patients with a history of CV events (i.e., at least one CV event), there was a significantly higher rate of CV events in agonist (22.4 event per 100 Person-year) versus degarelix-treated patients (11.3 event per 100 Person-year, p=0.0015) (FIG. 9B). Similar trends were observed when focusing on monthly treatment regimes only (FIGS. 9C and 9D).

Adjustment for age and PCa stage (metastatic vs. others) did not change the separation of the curve (HR=0.49, 95% CI 0.32-0.74, p=0.0009).

Independent Predictors of CV Events

To further explore the apparent independent role of treatment choice and identify independent modifiable risk factors, this study established Cox proportional hazard models including CV events occurring during treatment as dependent variable and age, history of CV event, drinking (i.e., high alcohol consumption or abstinence) and smoking habits, hypertension, serum testosterone level and PCa disease stage as independent variables.

As expected, the highest risk was posed by history of a CV event marking advanced vascular disease (2.23-fold).

Other risk factors included age, abstinence to alcohol, high blood pressure (regardless of treatment), and low baseline serum testosterone. Although smoking and metastatic disease stage was associated with increased hazard rates (HRs), these factors did not reach statistical significance.

When taking into consideration all of these characteristics and CV risk factors, the risk of an event was 38% lower if taking degarelix versus the agonist (HR=0.62, 95% CI 0.39-0.97, p=0.037).

Analysis

One finding from this study was the ~2-fold higher CV event rate in agonist versus antagonist-treated patients with a history of CV events (i.e., at least one cardiovascular event) in face of comparable event rates in patients with no CV history. The observation that advanced vascular disease is a prerequisite of the apparent harm of agonists implicates destabilization of existing atherosclerotic plaques as the plausible mechanism, which is affected reciprocally by the two drug classes.

The finding that the relative increase in the risk of CV events posed by agonists regards patients with advanced CV disease finds link to numerous epidemiological studies documenting the association of GnRH agonists to CV harm in older patients, i.e. ≥66 years old (Keating et al. (2006) *J. Clin. Oncol.* 24:4448-56; and Saigal et al. (2007) *Cancer* 110:1493-500). It was the study by Tsai et al ((2007) *Natl. Cancer Inst.* 99:1516-24) that highlighted by stratified analysis that the excess in CV risk posed by GnRH agonists is higher in patients >65 years than in their younger counterparts. Since the prevalence and severity of atherosclerosis is increasing with advancing age (Wong et al. (2011) *Atherosclerosis* 214:436-41), it is reasonable to assume that populations of elderly are likely enriched for patients with advanced atherosclerosis, which in turn can increase susceptibility to complications. This line of thinking was directly supported by observations highlighting increased all-cause mortality in patients with a history of a major CV event (Hayes et al. (2010) 106:979-85; and D'Amico et al. (2008) *JAMA* 299:289-95).

Randomized clinical trials can be particularly useful to dissect the independent contribution of medications to CV risk. These trials yield balanced treatment arms, collect detailed data on medical history and baseline risk factors, and monitor patients closely for safety data in a prospective manner. A recent meta-analysis of 8 randomized trials collectively involving 4141 patients found no differences in the incidence of CV deaths between treatment arms with or without GnRH agonist treatment over a 10-year follow-up period (Nguyen et al. (2011) *JAMA* 306:2359-66). While this finding seemingly contradicts the epidemiological studies, there are numerous issues accompanying this approach.

For example, the very long follow-up time (7 to 13 years) introduces significant contribution by aging and related metabolic alterations, which is among the strongest drivers of CV events. These factors may on the long run overshadow drug-related risks, especially if they arise in the early phase of the treatment, as suggested by numerous observations, and only in certain subpopulations. Furthermore, the meta-analysis did not allow conducting time-to-event analysis and stratification according to underlying CV disease, hence leaving uncertainties to their conclusions. These limitations were carefully highlighted by the authors and they called upon further data from randomized clinical trials to investigate these pending issues.

The present analysis took these recommendations into account and added an additional angle to it by using a unique control setting. By contrasting the GnRH agonists to a parallel group of patients treated with an antagonist it was also possible to address the direct role of GnRH receptors independent of androgen deprivation that was comparable between treatment arms. The combined consideration of these conditions revealed clear differences between agonists and antagonists in terms of their CV harm. In the lack of a parallel untreated group of patients with history of CV events, there is no direct evidence that CV event rate in the degarelix treatment arm is comparable with what can be expected from patients with a history of CV disease. However, it is unlikely that the GnRH antagonist—having no possibility by molecular design to evoke signal transduction—can trigger events via GnRH receptors (Beckers et al. (1997) *Anal. Biochem.* 251:17-23). Moreover, the herein argued scenarios could also help to explain the inconsistencies between previous studies by emphasizing the relative importance of patients with history of major CV events in the study population. Low percentage of patients with a history of CV event could drive negative, whereas high percentage of patients with CV history could drive positive overall conclusions.

There is no definitive understanding as to how differences in the modulation of GnRH receptors by the two drug classes could differentiate CV safety profiles. The differences in the action of these drugs are to be found outside the pituitary gland that merely drives the suppression of testicular testosterone production, an effect that is comparable between agonists and antagonists beyond 14-28 days (Klotz et al. (2008) *BJU Int.* 102:1531-8). Demonstration of the presence of functionally active GnRH receptors in lymphocytes (Chen et al. (1999) *J. Clin. Endocrinol Metab.* 84:743-50; Tanriverdi et al. (2004) *Exp. Clin. Endocrinol Diabetes* 112:587-94; and Tanriverdi et al. (2005) *Clin. Exp. Immunol.* 142:103-10), a player in the immuno-inflammatory system has opened new avenues for the exploration of differences in the systemic pharmacodynamic effects of agonists and antagonists. Since these cells are present in late-stage atherosclerotic plaques and play a key role in the regulation of collagen turnover and thereby the stability of the plaque (Businario et al. (2005) *Ital. J. Anat. Embroyl* 110(2 Suppl 1):109-15; Abbate et al. (2008) *Heart* 94:737-42; and de Boer et al. (1999) *J. Pathol.* 188:174-9), due consideration and targeted investigations in future studies seem warranted.

The multivariate analyses highlighted numerous independent risk factors for CV events during ADT and thereby a constellation of characteristics that predispose to an event relatively shortly after treatment initiation. Patients with advanced age, history of CV event who are having low baseline testosterone (possibly reflecting central adiposity and concomitant risk of accelerated atherosclerosis), hypertension or poorly controlled hypertension, and are abstinent to alcohol are seemingly at the highest risk for CV complications during ADT. Even in these patients, choosing an antagonist versus an agonist could reduce the relative risk by ~40%, which could theoretically be further improved by targeted lifestyle modifications (blood pressure control, weight loss, and moderate alcohol consumption).

What is claimed is:

1. A method of treating prostate cancer in a subject, comprising:
   selecting a subject that has prostate cancer and a history of at least one cardiovascular event; and
   administering degarelix to the subject, wherein administering degarelix to the subject comprises administering to the patient an initial dose of degarelix of 240 mg given as two injections of 120 mg each, and administering to the patient a maintenance dose of degarelix of 80 mg given as one injection, wherein the maintenance dose is administered approximately every 28 days after the previous dose of degarelix for a duration treatment, wherein administering degarelix to the subject decreases the likelihood of developing or experiencing an additional cardiovascular event compared to treatment with a gonadotrophin releasing hormone (GnRH) agonist.

2. The method of claim 1, wherein the at least one cardiovascular event is chosen from myocardial infarction, ischemic heart disease, ischemic stroke, hemorrhagic stroke, and other arterial thrombotic/embolic events.

3. The method of claim 1, wherein the subject has at least one risk factor chosen from greater than 65 years of age, high alcohol consumption, abstinence from alcohol, high blood pressure, low baseline serum testosterone, and prostate cancer disease state.

4. The method of claim 3, wherein the high blood pressure is greater than or equal to 130 over 85 mm Hg.

5. The method of claim 1, wherein the prostate cancer is chosen from localized prostate cancer, locally advanced prostate cancer, metastatic prostate cancer, and non-classifiable prostate cancer.

6. The method of claim 1, wherein the decreased likelihood of developing or experiencing an additional cardiovascular event is chosen from myocardial infarction or stroke.

7. The method of claim 1, wherein the initial dose of degarelix is given as two subcutaneous injections of 120 mg each at a concentration of 40 mg/mL.

8. The method of claim 1, wherein the maintenance dose of degarelix of 80 mg is given as one subcutaneous injection at a concentration of 20 mg/mL.

9. The method of claim 1, wherein the treatment with a GnRH agonist is treatment with monthly intramuscular injections of 7.5 mg leuprolide.

10. The method of claim 1, wherein the subject's risk of experiencing an increase in body weight is diminished compared to a risk of experiencing an increase in body weight upon treatment with a GnRH agonist.

11. The method of claim 10, wherein the treatment with a GnRH agonist is treatment with monthly intramuscular injections of 7.5 mg leuprolide.

* * * * *